US010011833B2

(12) United States Patent
Vagle

(10) Patent No.: US 10,011,833 B2
(45) Date of Patent: Jul. 3, 2018

(54) BRIDGED BICYCLIC NUCLEOSIDES

(71) Applicant: MIRAGEN THERAPEUTICS, INC., Boulder, CO (US)

(72) Inventor: Kurt Vagle, Boulder, CO (US)

(73) Assignee: MIRAGEN THERAPEUTICS, INC., Boulder, CO (US)

( * ) Notice: Subject to any disclaimer, the term of this patent is extended or adjusted under 35 U.S.C. 154(b) by 165 days.

(21) Appl. No.: 14/771,966

(22) PCT Filed: Mar. 16, 2014

(86) PCT No.: PCT/US2014/030100
§ 371 (c)(1),
(2) Date: Sep. 1, 2015

(87) PCT Pub. No.: WO2014/145356
PCT Pub. Date: Sep. 18, 2014

(65) Prior Publication Data
US 2016/0010090 A1 Jan. 14, 2016

Related U.S. Application Data

(60) Provisional application No. 61/791,704, filed on Mar. 15, 2013.

(51) Int. Cl.
*C12N 15/113* (2010.01)
*C07H 19/10* (2006.01)
*C07H 21/04* (2006.01)
*C12N 15/11* (2006.01)

(52) U.S. Cl.
CPC ........... *C12N 15/113* (2013.01); *C07H 19/10* (2013.01); *C07H 21/04* (2013.01); *C12N 15/111* (2013.01); *C12N 2310/113* (2013.01); *C12N 2310/315* (2013.01); *C12N 2310/3231* (2013.01); *C12N 2310/346* (2013.01); *C12N 2320/50* (2013.01); *C12N 2330/30* (2013.01)

(58) Field of Classification Search
None
See application file for complete search history.

(56) References Cited

U.S. PATENT DOCUMENTS

| | | | |
|---|---|---|---|
| 5,783,565 A | 7/1998 | Lee et al. | |
| 5,837,533 A | 11/1998 | Boutin | |
| 5,981,505 A | 11/1999 | Weiner et al. | |
| 6,127,170 A | 10/2000 | Boutin | |
| 6,217,900 B1 | 4/2001 | Ciccarelli et al. | |
| 6,268,490 B1 | 7/2001 | Imanishi et al. | |
| 6,316,198 B1 | 11/2001 | Skouv et al. | |
| 6,379,965 B1 | 4/2002 | Boutin | |
| 6,383,512 B1 | 5/2002 | Ciccarelli et al. | |
| 6,403,566 B1 | 6/2002 | Wang | |
| 6,416,510 B1 | 7/2002 | Altman et al. | |
| 6,670,461 B1 | 12/2003 | Wengel et al. | |
| 6,716,196 B2 | 4/2004 | Lesh et al. | |
| 6,747,014 B2 | 6/2004 | Teng et al. | |
| 6,770,748 B2 | 8/2004 | Imanishi et al. | |
| 6,833,361 B2 | 12/2004 | Hong et al. | |
| 6,953,466 B2 | 10/2005 | Palasis et al. | |
| 6,998,484 B2 | 2/2006 | Koch et al. | |
| 7,034,133 B2 | 4/2006 | Wengel et al. | |
| 7,044,969 B2 | 5/2006 | Errico et al. | |
| 7,202,227 B2 | 4/2007 | Boutin | |
| 8,642,751 B2 | 2/2014 | Dalby et al. | |
| 2003/0028013 A1 | 2/2003 | Wang et al. | |
| 2006/0148742 A1 | 7/2006 | Kaye et al. | |
| 2007/0060907 A1 | 3/2007 | Shapland et al. | |
| 2007/0203445 A1 | 8/2007 | Kaye et al. | |
| 2010/0324118 A1 | 12/2010 | Dimmeler et al. | |
| 2011/0281933 A1 | 11/2011 | Baldan et al. | |
| 2012/0238619 A1 | 9/2012 | Dimmeler et al. | |
| 2013/0041144 A1 | 2/2013 | Migawa et al. | |
| 2013/0345288 A1 | 12/2013 | Van Rooij et al. | |
| 2017/0073368 A1 | 3/2017 | Vagle | |

FOREIGN PATENT DOCUMENTS

| | | |
|---|---|---|
| EP | 2 612 914 A1 | 7/2013 |
| JP | 2009-532044 A | 9/2009 |
| JP | 2009-536222 A | 10/2009 |
| JP | 2017-512774 A | 5/2017 |
| WO | WO 99/60855 A1 | 12/1999 |
| WO | WO 2003/093449 A2 | 11/2003 |
| WO | WO 2005/082440 A1 | 9/2005 |
| WO | WO 2006/089340 A1 | 4/2006 |
| WO | WO 2007/070483 A3 | 6/2007 |
| WO | WO-2007/112753 A2 | 10/2007 |
| WO | WO-2007/112753 A3 | 10/2007 |

(Continued)

OTHER PUBLICATIONS

Wang et al., Bioorganic and Medicinal Chemistry Letters, vol. 9, 1999, pp. 1147-1150.*
Beaucage, et al., "Advances in the Synthesis of Oligonucleotides by the Phosphoramidite Approach", Tetrahedron (1992); 48(12): 2223-2311.
Borch and Hassid, "A New Method for the Methylation of Amines", J. Org. Chem. (1972); 37(10): 1673-1674.
Caruthers, et al., "New chemical methods for synthesizing polynucleotides", Nucleic Acids Symp Ser. (1980); 7: 215-223.
International Application No. PCT/US2014/030100, International Search Report and Written Opinion dated Aug. 21, 2014.
International Application No. PCT/US2014/030100, International Preliminary Report on Patentability dated Sep. 15, 2015.
McBride, et al., "An investigation of several deoxynucleoside phosphoramidites useful for synthesizing deoxyoligonucleotides", Tetrahedron Letters (1983); 24(3): 245-248.

(Continued)

*Primary Examiner* — Traviss C McIntosh, III
(74) *Attorney, Agent, or Firm* — Cooley LLP

(57) ABSTRACT

The present invention relates to 2'-C-Bridged Bicyclic Nucleosides and Nucleotides, and oligonucleotides comprising at least one 2'-C-Bridged Bicyclic Nucleotides. The present invention further provides pharmaceutical compositions comprising the nucleosides, nucleotides, and oligonucleotides, as well as their respective methods of use and synthesis.

48 Claims, 11 Drawing Sheets

(56) References Cited

FOREIGN PATENT DOCUMENTS

| WO | WO-2007/143315 A2 | 12/2007 |
|----|-------------------|---------|
| WO | WO-2007/143315 A3 | 12/2007 |
| WO | WO 2009/018493 A1 | 2/2009 |
| WO | WO 2009/062169 A3 | 5/2009 |
| WO | WO 2009/073809 A3 | 6/2009 |
| WO | WO 2009/105759 A2 | 8/2009 |
| WO | WO 2009/117418 A3 | 9/2009 |
| WO | WO 2010/019574 A1 | 2/2010 |
| WO | WO 2010/129672 A1 | 11/2010 |
| WO | WO 2011/085102 A1 | 7/2011 |
| WO | WO 2011/115818 A1 | 9/2011 |
| WO | WO 2011/153542 A3 | 12/2011 |
| WO | WO 2011/156202 A1 | 12/2011 |
| WO | WO 2012/029870 A1 | 3/2012 |
| WO | WO 2012/061810 A1 | 5/2012 |
| WO | WO 2012/083005 A3 | 6/2012 |
| WO | WO 2012/148373 A1 | 11/2012 |
| WO | WO 2012/153135 A1 | 11/2012 |
| WO | WO-2013/036868 A1 | 3/2013 |
| WO | WO 2013/036868 A1 | 3/2013 |
| WO | WO 2013/052965 A2 | 4/2013 |
| WO | WO 2014/145356 A1 | 9/2014 |
| WO | WO-2015/142735 A1 | 9/2015 |

OTHER PUBLICATIONS

Singh, et al., "LNA (locked nucleic acids): synthesis and high-affinity nucleic acid recognition", Chem. Commun. (1998); 455-456.

Singh, et al., "Synthesis of 2'-Amino-LNA: A Novel Conformationally Restricted High-Affinity Oligonucleotide Analogue with a Handle", J. Org. Chem. (1998); 63(26): 10035-10039.

Sinha, et al., "β-Cyanoethyl N,N-dialkylamino/N-morpholinomonochloro phosphoamidites, new phosphitylating agents facilitating ease of deprotection and work-up of synthesized oligonucleotides", Tetrahedron Letters (1983); 24(52): 5843-5846.

Wang, et al., "Conformationally locked nucleosides. Synthesis and stereochemical assignments of 2'- C,4'C-bridged bicyclonucleosides", Tetrahedron (1999); 5(25): 7707-7724.

Singh et al., "Synthesis of Novel Bicyclo[2.2.1] Ribonucleosides: 2'-Amino- and 2'-Thio-LNA Monomeric Nucleosides," J. Org. Chem. 63:6078-6079 (1998).

Supplementary European Search Report, EP appl. No. 14765516.1, 6 pages (dated Aug. 5, 2016).

Cumpstey, "Intramolecular aglycon delivery," Carbohydrate Res. 343:1553-1573 (2008).

Extended European Search Report, EP Appl. No. 15764239.8, 9 pages (dated Jul. 27, 2017).

International Search Report, PCT Appl. No. PCT/US2015/020761, 3 pages (dated Jun. 18, 2015).

Ioannidis et al., "Synthesis of Some 2',3'-Dideoxy 2'-C Methyl-Substituted Nucleosides," Nucleosides & Nucleotides, 11(6):1205-1218 (1992).

Li and Piccirilli, "Efficient synthesis of 2'-C-a-aminomethyl-2'-deoxynucleosides," Chem. Commun. 48:8754-8756 (2012).

Li and Piccirilli, "Synthesis of 2'-Deoxy 2'-C-a-methylpurine Nucleosides," Synthesis 17:2865-2870 (2005).

Li and Piccirilli, "Synthesis of the Phosphoramidite Derivatives of 2'-Deoxy-2'-C-a-methylcytidine and 2'-Deoxy-2'-C-a-hydroxymethylcytidine: Analogues for Chemical Dissection ofRNA's 2'-Hydroxyl Group," J. Org. Chem. 69:4751-4759 (2004).

Seth et al. (2010). "Synthesis and biophysical evaluation of 2',4'-constrained 2'O-methoxyethyl and 2',4'-constrained 2'O-ethyl nucleic acid analogues," J. Org. Chem. 75:1569-1581.

Written Opinion of the International Searching Authority, PCT Appl. No. PCT/US2015/020761, 5 pages (dated Jun. 18, 2015).

Japanese office action for Japanese patent application No. 2016-503331, 27 pages (with English translation).

\* cited by examiner

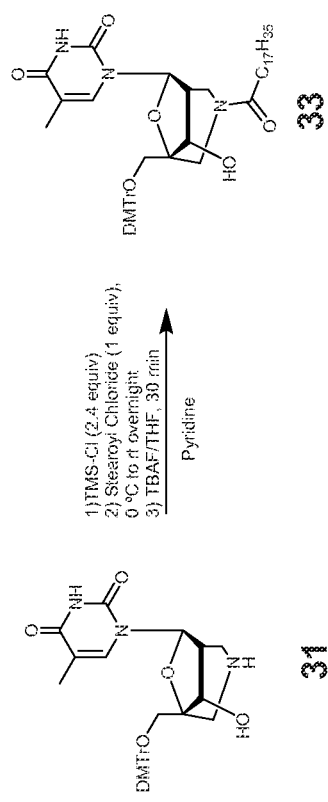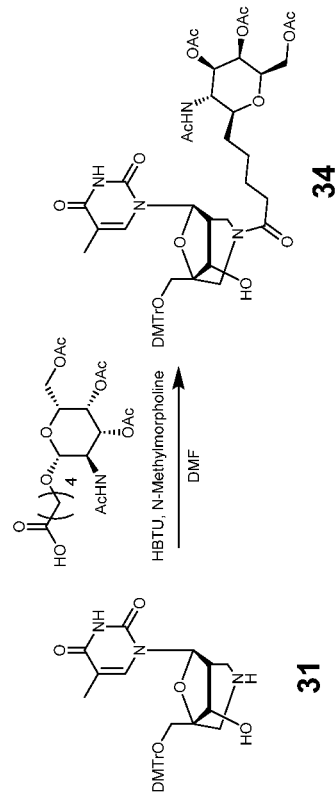

FIGURE 5A

| Modification | LNA | aminoLNA | oxoENA | aminoENA |
|---|---|---|---|---|
| Structure | | | | |
| $\Delta T_m$, PO BB, RNA Complement, vs. dT Single Mod | +9 °C/Mod* | +6.6 °C/Mod* | NA | +2.5-4.0 °C/Mod# |
| $\Delta T_m$, PO BB, RNA Complement, vs. dT Multiple Mods | +5-7 °C/Mod* | +6.3 °C/Mod* | +3.5-5.2 °C/Mod** | NA |

*Literature value, 9-mer
**Literature value, 12-mer

FIGURE 5B

| Modification | oxoCBBN | aminoCBBN |
|---|---|---|
| Structure | | |
| $\Delta T_m$, PO BB, RNA Complement, vs. dT Single Mod | +5.3 °C/Mod## | +8.9 °C/Mod## |
| $\Delta T_m$, PO BB, RNA Complement, vs. dT Multiple Mods | +2.8 °C/Mod## | +5.2 °C/Mod## |

Literature value, 15-mer
miRagen experimental value, 16-mer

```
                      SEQUENCE LISTING

<160> NUMBER OF SEQ ID NOS: 83

<210> SEQ ID NO 1
<211> LENGTH: 22
<212> TYPE: RNA
<213> ORGANISM: Homo sapiens

<400> SEQUENCE: 1
uggaauguaa agaaguaugu au                                              22

<210> SEQ ID NO 2
<211> LENGTH: 22
<212> TYPE: RNA
<213> ORGANISM: Homo sapiens

<400> SEQUENCE: 2
aacccguaga uccgaacuug ug                                              22

<210> SEQ ID NO 3
<211> LENGTH: 23
<212> TYPE: RNA
<213> ORGANISM: Homo sapiens

<400> SEQUENCE: 3
uacccuguag aaccgaauuu gug                                             23

<210> SEQ ID NO 4
<211> LENGTH: 22
<212> TYPE: RNA
<213> ORGANISM: Homo sapiens

<400> SEQUENCE: 4
ucccugagac ccuaacuugu ga                                              22

<210> SEQ ID NO 5
<211> LENGTH: 21
<212> TYPE: RNA
<213> ORGANISM: Homo sapiens

<400> SEQUENCE: 5
ucacagugaa ccggucucuu u                                               21

<210> SEQ ID NO 6
<211> LENGTH: 22
<212> TYPE: RNA
<213> ORGANISM: Homo sapiens
```

```
<400> SEQUENCE: 6
uuuggucccc uucaaccagc ug                                              22

<210> SEQ ID NO 7
<211> LENGTH: 22
<212> TYPE: RNA
<213> ORGANISM: Homo sapiens

<400> SEQUENCE: 7
uuuggucccc uucaaccagc ua                                              22

<210> SEQ ID NO 8
<211> LENGTH: 22
<212> TYPE: RNA
<213> ORGANISM: Homo sapiens

<400> SEQUENCE: 8
ucuacagugc acgugucucc ag                                              22

<210> SEQ ID NO 9
<211> LENGTH: 21
<212> TYPE: RNA
<213> ORGANISM: Homo sapiens

<400> SEQUENCE: 9
ugagaugaag cacuguagcu c                                               21

<210> SEQ ID NO 10
<211> LENGTH: 23
<212> TYPE: RNA
<213> ORGANISM: Homo sapiens

<400> SEQUENCE: 10
guccaguuuu cccaggaauc ccu                                             23

<210> SEQ ID NO 11
<211> LENGTH: 22
<212> TYPE: RNA
<213> ORGANISM: Homo sapiens

<400> SEQUENCE: 11
ucucccaacc cuuguaccag ug                                              22

<210> SEQ ID NO 12
<211> LENGTH: 22
<212> TYPE: RNA
<213> ORGANISM: Homo sapiens

<400> SEQUENCE: 12
uagcagcaca uaaugguuug ug                                              22

<210> SEQ ID NO 13
<211> LENGTH: 22
<212> TYPE: RNA
<213> ORGANISM: Homo sapiens

<400> SEQUENCE: 13
uagcagcaca ucaugguuua ca                                              22

<210> SEQ ID NO 14
<211> LENGTH: 22
<212> TYPE: RNA
```

<213> ORGANISM: Homo sapiens

<400> SEQUENCE: 14
uagcagcacg uaaauauugg cg    22

<210> SEQ ID NO 15
<211> LENGTH: 23
<212> TYPE: RNA
<213> ORGANISM: Homo sapiens

<400> SEQUENCE: 15
aacauucauu gcugucggug ggu    23

<210> SEQ ID NO 16
<211> LENGTH: 21
<212> TYPE: RNA
<213> ORGANISM: Homo sapiens

<400> SEQUENCE: 16
uagcagcaca gaaauauugg c    21

<210> SEQ ID NO 17
<211> LENGTH: 22
<212> TYPE: RNA
<213> ORGANISM: Homo sapiens

<400> SEQUENCE: 17
uucaccaccu ucuccaccca gc    22

<210> SEQ ID NO 18
<211> LENGTH: 23
<212> TYPE: RNA
<213> ORGANISM: Homo sapiens

<400> SEQUENCE: 18
cccaguguuc agacuaccug uuc    23

<210> SEQ ID NO 19
<211> LENGTH: 23
<212> TYPE: RNA
<213> ORGANISM: Homo sapiens

<400> SEQUENCE: 19
cccaguguuu agacuaucug uuc    23

<210> SEQ ID NO 20
<211> LENGTH: 22
<212> TYPE: RNA
<213> ORGANISM: Homo sapiens

<400> SEQUENCE: 20
acaguagucu gcacauuggu ua    22

<210> SEQ ID NO 21
<211> LENGTH: 22
<212> TYPE: RNA
<213> ORGANISM: Homo sapiens

<400> SEQUENCE: 21
uggaauguaa ggaagugugu gg    22

<210> SEQ ID NO 22
<211> LENGTH: 22

<212> TYPE: RNA
<213> ORGANISM: Homo sapiens

<400> SEQUENCE: 22
auaagacgag caaaaagcuu gu          22

<210> SEQ ID NO 23
<211> LENGTH: 22
<212> TYPE: RNA
<213> ORGANISM: Homo sapiens

<400> SEQUENCE: 23
auaagacgaa caaaagguuu gu          22

<210> SEQ ID NO 24
<211> LENGTH: 23
<212> TYPE: RNA
<213> ORGANISM: Homo sapiens

<400> SEQUENCE: 24
uaaagugcuu auagugcagg uag          23

<210> SEQ ID NO 25
<211> LENGTH: 22
<212> TYPE: RNA
<213> ORGANISM: Homo sapiens

<400> SEQUENCE: 25
uagcuuauca gacugauguu ga          22

<210> SEQ ID NO 26
<211> LENGTH: 22
<212> TYPE: RNA
<213> ORGANISM: Homo sapiens

<400> SEQUENCE: 26
acagcaggca cagacaggca gu          22

<210> SEQ ID NO 27
<211> LENGTH: 22
<212> TYPE: RNA
<213> ORGANISM: Homo sapiens

<400> SEQUENCE: 27
aagcugccag uugaagaacu gu          22

<210> SEQ ID NO 28
<211> LENGTH: 23
<212> TYPE: RNA
<213> ORGANISM: Homo sapiens

<400> SEQUENCE: 28
agcuacauug ucugcugggu uuc          23

<210> SEQ ID NO 29
<211> LENGTH: 21
<212> TYPE: RNA
<213> ORGANISM: Homo sapiens

<400> SEQUENCE: 29
agcuacaucu ggcuacuggg u          21

<210> SEQ ID NO 30

```
<211> LENGTH: 21
<212> TYPE: RNA
<213> ORGANISM: Homo sapiens

<400> SEQUENCE: 30
caagucacua gugguuccgu u                                              21

<210> SEQ ID NO 31
<211> LENGTH: 21
<212> TYPE: RNA
<213> ORGANISM: Homo sapiens

<400> SEQUENCE: 31
aucacauugc cagggauuuc c                                              21

<210> SEQ ID NO 32
<211> LENGTH: 22
<212> TYPE: RNA
<213> ORGANISM: Homo sapiens

<400> SEQUENCE: 32
uucaaguaau ccaggauagg cu                                             22

<210> SEQ ID NO 33
<211> LENGTH: 21
<212> TYPE: RNA
<213> ORGANISM: Homo sapiens

<400> SEQUENCE: 33
uucaaguaau ucaggauagg u                                              21

<210> SEQ ID NO 34
<211> LENGTH: 22
<212> TYPE: RNA
<213> ORGANISM: Homo sapiens

<400> SEQUENCE: 34
aaggagcuca cagucuauug ag                                             22

<210> SEQ ID NO 35
<211> LENGTH: 22
<212> TYPE: RNA
<213> ORGANISM: Homo sapiens

<400> SEQUENCE: 35
uagcaccauc ugaaaucggu ua                                             22

<210> SEQ ID NO 36
<211> LENGTH: 23
<212> TYPE: RNA
<213> ORGANISM: Homo sapiens

<400> SEQUENCE: 36
uagcaccauu ugaaaucagu guu                                            23

<210> SEQ ID NO 37
<211> LENGTH: 22
<212> TYPE: RNA
<213> ORGANISM: Homo sapiens

<400> SEQUENCE: 37
uagcaccauu ugaaaucggu ua                                             22
```

```
<210> SEQ ID NO 38
<211> LENGTH: 22
<212> TYPE: RNA
<213> ORGANISM: Homo sapiens

<400> SEQUENCE: 38
uguaaacauc cucgacugga ag                                          22

<210> SEQ ID NO 39
<211> LENGTH: 22
<212> TYPE: RNA
<213> ORGANISM: Homo sapiens

<400> SEQUENCE: 39
uguaaacauc cuacacucag cu                                          22

<210> SEQ ID NO 40
<211> LENGTH: 23
<212> TYPE: RNA
<213> ORGANISM: Homo sapiens

<400> SEQUENCE: 40
uguaaacauc cuacacucuc agc                                         23

<210> SEQ ID NO 41
<211> LENGTH: 22
<212> TYPE: RNA
<213> ORGANISM: Homo sapiens

<400> SEQUENCE: 41
uguaaacauc cccgacugga ag                                          22

<210> SEQ ID NO 42
<211> LENGTH: 22
<212> TYPE: RNA
<213> ORGANISM: Homo sapiens

<400> SEQUENCE: 42
uguaaacauc cuugacugga ag                                          22

<210> SEQ ID NO 43
<211> LENGTH: 23
<212> TYPE: RNA
<213> ORGANISM: Homo sapiens

<400> SEQUENCE: 43
ucucacacag aaaucgcacc cgu                                         23

<210> SEQ ID NO 44
<211> LENGTH: 22
<212> TYPE: RNA
<213> ORGANISM: Homo sapiens

<400> SEQUENCE: 44
gaaguuguuc gugguggauu cg                                          22

<210> SEQ ID NO 45
<211> LENGTH: 22
<212> TYPE: RNA
<213> ORGANISM: Homo sapiens

<400> SEQUENCE: 45
acuggacuua gggucagaag gc                                          22
```

```
<210> SEQ ID NO 46
<211> LENGTH: 21
<212> TYPE: RNA
<213> ORGANISM: Homo sapiens

<400> SEQUENCE: 46
acuggacuug gagucagaag g                                              21

<210> SEQ ID NO 47
<211> LENGTH: 22
<212> TYPE: RNA
<213> ORGANISM: Homo sapiens

<400> SEQUENCE: 47
cagcagcaau ucauguuuug aa                                             22

<210> SEQ ID NO 48
<211> LENGTH: 21
<212> TYPE: RNA
<213> ORGANISM: Homo sapiens

<400> SEQUENCE: 48
ucacuccucu ccucccgucu u                                              21

<210> SEQ ID NO 49
<211> LENGTH: 22
<212> TYPE: RNA
<213> ORGANISM: Homo sapiens

<400> SEQUENCE: 49
ucaggcucag uccccucccg au                                             22

<210> SEQ ID NO 50
<211> LENGTH: 22
<212> TYPE: RNA
<213> ORGANISM: Homo sapiens

<400> SEQUENCE: 50
uccuguacug agcugccccg ag                                             22

<210> SEQ ID NO 51
<211> LENGTH: 21
<212> TYPE: RNA
<213> ORGANISM: Homo sapiens

<400> SEQUENCE: 51
cagcagcaca cugugguuug u                                              21

<210> SEQ ID NO 52
<211> LENGTH: 21
<212> TYPE: RNA
<213> ORGANISM: Homo sapiens

<400> SEQUENCE: 52
uuaagacuug cagugauguu u                                              21

<210> SEQ ID NO 53
<211> LENGTH: 23
<212> TYPE: RNA
<213> ORGANISM: Homo sapiens

<400> SEQUENCE: 53
ucggggauca ucaugucacg aga                                            23
```

```
<210> SEQ ID NO 54
<211> LENGTH: 22
<212> TYPE: RNA
<213> ORGANISM: Homo sapiens

<400> SEQUENCE: 54
uauugcacuu gucccggccu gu                                              22

<210> SEQ ID NO 55
<211> LENGTH: 22
<212> TYPE: RNA
<213> ORGANISM: Homo sapiens

<400> SEQUENCE: 55
uauugcacuc gucccggccu cc                                              22

<210> SEQ ID NO 56
<211> LENGTH: 22
<212> TYPE: RNA
<213> ORGANISM: Homo sapiens

<400> SEQUENCE: 56
ugagguagua gguuguauag uu                                              22

<210> SEQ ID NO 57
<211> LENGTH: 22
<212> TYPE: RNA
<213> ORGANISM: Homo sapiens

<400> SEQUENCE: 57
ugagguagua gguugugugg uu                                              22

<210> SEQ ID NO 58
<211> LENGTH: 22
<212> TYPE: RNA
<213> ORGANISM: Homo sapiens

<400> SEQUENCE: 58
ugagguagua gguuguaugg uu                                              22

<210> SEQ ID NO 59
<211> LENGTH: 22
<212> TYPE: RNA
<213> ORGANISM: Homo sapiens

<400> SEQUENCE: 59
agagguagua gguugcauag uu                                              22

<210> SEQ ID NO 60
<211> LENGTH: 22
<212> TYPE: RNA
<213> ORGANISM: Homo sapiens

<400> SEQUENCE: 60
ugagguagga gguuguauag uu                                              22

<210> SEQ ID NO 61
<211> LENGTH: 22
<212> TYPE: RNA
<213> ORGANISM: Homo sapiens

<400> SEQUENCE: 61
```

-continued ugagguagua gauuguauag uu                                    22

<210> SEQ ID NO 62
<211> LENGTH: 22
<212> TYPE: RNA
<213> ORGANISM: Homo sapiens

<400> SEQUENCE: 62
ugagguagua guuuguacag uu                                    22

<210> SEQ ID NO 63
<211> LENGTH: 22
<212> TYPE: RNA
<213> ORGANISM: Homo sapiens

<400> SEQUENCE: 63
aaaccguuac cauuacugag uu                                    22

<210> SEQ ID NO 64
<211> LENGTH: 16
<212> TYPE: DNA
<213> ORGANISM: Artificial Sequence
<220> FEATURE:
<223> OTHER INFORMATION: oligonucleotide compound M-11915
<220> FEATURE:
<221> NAME/KEY: misc_feature
<222> LOCATION: (9)..(9)
<223> OTHER INFORMATION: n may be an amino-2'-C-bridged bicyclic
      thymidine

<400> SEQUENCE: 64 cttttttgcnc gtctta                                          16

<210> SEQ ID NO 65
<211> LENGTH: 16
<212> TYPE: DNA
<213> ORGANISM: Artificial Sequence
<220> FEATURE:
<223> OTHER INFORMATION: oligonucleotide compound M-11916
<220> FEATURE:
<221> NAME/KEY: misc_feature
<222> LOCATION: (6)..(6)
<223> OTHER INFORMATION: n may be an amino-2'-C-bridged bicyclic
      thymidine
<220> FEATURE:
<221> NAME/KEY: misc_feature
<222> LOCATION: (9)..(9)
<223> OTHER INFORMATION: n may be an amino-2'-C-bridged bicyclic
      thymidine

<400> SEQUENCE: 65
cttttngcnc gtctta                                           16

<210> SEQ ID NO 66
<211> LENGTH: 16
<212> TYPE: DNA
<213> ORGANISM: Artificial Sequence
<220> FEATURE:
<223> OTHER INFORMATION: oligonucleotide compound M-11917
<220> FEATURE:
<221> NAME/KEY: misc_feature
<222> LOCATION: (5)..(6)
<223> OTHER INFORMATION: n may be an amino-2'-C-bridged bicyclic
      thymidine
<220> FEATURE:
<221> NAME/KEY: misc_feature
<222> LOCATION: (9)..(9)
<223> OTHER INFORMATION: n may be an amino-2'-C-bridged bicyclic
      thymidine

```
<400> SEQUENCE: 66
ctttnngcnc gtctta                                              16

<210> SEQ ID NO 67
<211> LENGTH: 16
<212> TYPE: DNA
<213> ORGANISM: Artificial Sequence
<220> FEATURE:
<223> OTHER INFORMATION: oligonucleotide compound M-11918
<220> FEATURE:
<221> NAME/KEY: misc_feature
<222> LOCATION: (5)..(6)
<223> OTHER INFORMATION: n may be an amino-2'-C-bridged bicyclic
      thymidine

<400> SEQUENCE: 67
ctttnngctc gtctta                                              16

<210> SEQ ID NO 68
<211> LENGTH: 16
<212> TYPE: DNA
<213> ORGANISM: Artificial Sequence
<220> FEATURE:
<223> OTHER INFORMATION: oligonucleotide compound M-11919
<220> FEATURE:
<221> NAME/KEY: misc_feature
<222> LOCATION: (1)..(1)
<223> OTHER INFORMATION: n may be an locked nucleic acid
      phosphorothioate cytidine
<220> FEATURE:
<221> NAME/KEY: misc_feature
<222> LOCATION: (2)..(4)
<223> OTHER INFORMATION: n may be a phosphorothioate thymidine
<220> FEATURE:
<221> NAME/KEY: misc_feature
<222> LOCATION: (5)..(6)
<223> OTHER INFORMATION: n may be an amino-2'-C-bridged bicyclic
      phosphorothioate thymidine
<220> FEATURE:
<221> NAME/KEY: misc_feature
<222> LOCATION: (7)..(7)
<223> OTHER INFORMATION: n may be a phosphorothioate guanosine
<220> FEATURE:
<221> NAME/KEY: misc_feature
<222> LOCATION: (8)..(8)
<223> OTHER INFORMATION: n may be an locked nucleic acid
      phosphorothioate cytidine
<220> FEATURE:
<221> NAME/KEY: misc_feature
<222> LOCATION: (9)..(9)
<223> OTHER INFORMATION: n may be a phosphorothioate thymidine
<220> FEATURE:
<221> NAME/KEY: misc_feature
<222> LOCATION: (10)..(10)
<223> OTHER INFORMATION: n may be an locked nucleic acid
      phosphorothioate cytidine
<220> FEATURE:
<221> NAME/KEY: misc_feature
<222> LOCATION: (11)..(11)
<223> OTHER INFORMATION: n may be an locked nucleic acid
      phosphorothioate guanosine
<220> FEATURE:
<221> NAME/KEY: misc_feature
<222> LOCATION: (12)..(12)
<223> OTHER INFORMATION: n may be a phosphorothioate thymidine
<220> FEATURE:
<221> NAME/KEY: misc_feature
<222> LOCATION: (13)..(13)
<223> OTHER INFORMATION: n may be an locked nucleic acid
      phosphorothioate cytidine
<220> FEATURE:
<221> NAME/KEY: misc_feature
<222> LOCATION: (14)..(14)
<223> OTHER INFORMATION: n may be a phosphorothioate thymidine
<220> FEATURE:
```

<220> FEATURE:
<221> NAME/KEY: misc_feature
<222> LOCATION: (15)..(15)
<223> OTHER INFORMATION: n may be an locked nucleic acid
      phosphorothioate thymidine
<220> FEATURE:
<221> NAME/KEY: misc_feature
<222> LOCATION: (16)..(16)
<223> OTHER INFORMATION: n may be a locked nucleic acid adenosine

<400> SEQUENCE: 68 nnnnnnnnn nnnnnn                                                          16

<210> SEQ ID NO 69
<211> LENGTH: 16
<212> TYPE: DNA
<213> ORGANISM: Artificial Sequence
<220> FEATURE:
<223> OTHER INFORMATION: oligonucleotide compound M-11920
<220> FEATURE:
<221> NAME/KEY: misc_feature
<222> LOCATION: (1)..(1)
<223> OTHER INFORMATION: n may be an locked nucleic acid
      phosphorothioate cytidine
<220> FEATURE:
<221> NAME/KEY: misc_feature
<222> LOCATION: (2)..(4)
<223> OTHER INFORMATION: n may be a phosphorothioate thymidine
<220> FEATURE:
<221> NAME/KEY: misc_feature
<222> LOCATION: (5)..(6)
<223> OTHER INFORMATION: n may be an locked nucleic acid
      phosphorothioate thymidine
<220> FEATURE:
<221> NAME/KEY: misc_feature
<222> LOCATION: (7)..(7)
<223> OTHER INFORMATION: n may be a phosphorothioate guanosine
<220> FEATURE:
<221> NAME/KEY: misc_feature
<222> LOCATION: (8)..(8)
<223> OTHER INFORMATION: n may be an locked nucleic acid
      phosphorothioate cytidine
<220> FEATURE:
<221> NAME/KEY: misc_feature
<222> LOCATION: (9)..(9)
<223> OTHER INFORMATION: n may be a phosphorothioate thymidine
<220> FEATURE:
<221> NAME/KEY: misc_feature
<222> LOCATION: (10)..(10)
<223> OTHER INFORMATION: n may be an locked nucleic acid
      phosphorothioate cytidine
<220> FEATURE:
<221> NAME/KEY: misc_feature
<222> LOCATION: (11)..(11)
<223> OTHER INFORMATION: n may be an locked nucleic acid
      phosphorothioate guanosine
<220> FEATURE:
<221> NAME/KEY: misc_feature
<222> LOCATION: (12)..(12)
<223> OTHER INFORMATION: n may be a phosphorothioate thymidine
<220> FEATURE:
<221> NAME/KEY: misc_feature
<222> LOCATION: (13)..(13)
<223> OTHER INFORMATION: n may be an locked nucleic acid
      phosphorothioate cytidine
<220> FEATURE:
<221> NAME/KEY: misc_feature
<222> LOCATION: (14)..(14)
<223> OTHER INFORMATION: n may be a phosphorothioate thymidine
<220> FEATURE:
<221> NAME/KEY: misc_feature
<222> LOCATION: (15)..(15)
<223> OTHER INFORMATION: n may be an amino-2'-C-bridged bicyclic
      phosphorothioate thymidine
<220> FEATURE:
<221> NAME/KEY: misc_feature
<222> LOCATION: (16)..(16)
<223> OTHER INFORMATION: n may be a locked nucleic acid adenosine

```
<400> SEQUENCE: 69
nnnnnnnnnn nnnnnn                                                   16

<210> SEQ ID NO 70
<211> LENGTH: 16
<212> TYPE: DNA
<213> ORGANISM: Artificial Sequence
<220> FEATURE:
<223> OTHER INFORMATION: oligonucleotide compound M-10930
<220> FEATURE:
<221> NAME/KEY: misc_feature
<222> LOCATION: (9)..(9)
<223> OTHER INFORMATION: n may be an oxo-2'-C-bridged bicyclic
      thymidine

<400> SEQUENCE: 70 cttttttgcnc gtctta                                                  16

<210> SEQ ID NO 71
<211> LENGTH: 16
<212> TYPE: DNA
<213> ORGANISM: Artificial Sequence
<220> FEATURE:
<223> OTHER INFORMATION: oligonucleotide compound M-10924
<220> FEATURE:
<221> NAME/KEY: misc_feature
<222> LOCATION: (1)..(1)
<223> OTHER INFORMATION: n may be an oxo-2'-C-bridged bicyclic cytidine
<220> FEATURE:
<221> NAME/KEY: misc_feature
<222> LOCATION: (2)..(6)
<223> OTHER INFORMATION: n may be an oxo-2'-C-bridged bicyclic thymidine
<220> FEATURE:
<221> NAME/KEY: misc_feature
<222> LOCATION: (8)..(8)
<223> OTHER INFORMATION: n may be an oxo-2'-C-bridged bicyclic cytidine
<220> FEATURE:
<221> NAME/KEY: misc_feature
<222> LOCATION: (9)..(9)
<223> OTHER INFORMATION: n may be an oxo-2'-C-bridged bicyclic thymidine
<220> FEATURE:
<221> NAME/KEY: misc_feature
<222> LOCATION: (10)..(10)
<223> OTHER INFORMATION: n may be an oxo-2'-C-bridged bicyclic cytidine
<220> FEATURE:
<221> NAME/KEY: misc_feature
<222> LOCATION: (12)..(12)
<223> OTHER INFORMATION: n may be an oxo-2'-C-bridged bicyclic thymidine
<220> FEATURE:
<221> NAME/KEY: misc_feature
<222> LOCATION: (13)..(13)
<223> OTHER INFORMATION: n may be an oxo-2'-C-bridged bicyclic cytidine
<220> FEATURE:
<221> NAME/KEY: misc_feature
<222> LOCATION: (14)..(15)
<223> OTHER INFORMATION: n may be an oxo-2'-C-bridged bicyclic thymidine

<400> SEQUENCE: 71
nnnnnngnnn gnnnna                                                   16

<210> SEQ ID NO 72
<211> LENGTH: 16
<212> TYPE: DNA
<213> ORGANISM: Artificial Sequence
<220> FEATURE:
<223> OTHER INFORMATION: oligonucleotide 208a_DNA_PO

<400> SEQUENCE: 72 cttttttgctc gtctta                                                  16
```

```
<210> SEQ ID NO 73
<211> LENGTH: 16
<212> TYPE: DNA
<213> ORGANISM: Artificial Sequence
<220> FEATURE:
<223> OTHER INFORMATION: oligonucleotide 208a_CBBN C_T_DNA_16_3_PO
<220> FEATURE:
<221> NAME/KEY: misc_feature
<222> LOCATION: (1)..(1)
<223> OTHER INFORMATION: n may be an oxo-2'-C-bridged bicyclic cytidine
<220> FEATURE:
<221> NAME/KEY: misc_feature
<222> LOCATION: (2)..(6)
<223> OTHER INFORMATION: n may be an oxo-2'-C-bridged bicyclic thymidine
<220> FEATURE:
<221> NAME/KEY: misc_feature
<222> LOCATION: (8)..(8)
<223> OTHER INFORMATION: n may be an oxo-2'-C-bridged bicyclic cytidine
<220> FEATURE:
<221> NAME/KEY: misc_feature
<222> LOCATION: (9)..(9)
<223> OTHER INFORMATION: n may be an oxo-2'-C-bridged bicyclic thymidine
<220> FEATURE:
<221> NAME/KEY: misc_feature
<222> LOCATION: (10)..(10)
<223> OTHER INFORMATION: n may be an oxo-2'-C-bridged bicyclic cytidine
<220> FEATURE:
<221> NAME/KEY: misc_feature
<222> LOCATION: (12)..(12)
<223> OTHER INFORMATION: n may be an oxo-2'-C-bridged bicyclic thymidine
<220> FEATURE:
<221> NAME/KEY: misc_feature
<222> LOCATION: (13)..(13)
<223> OTHER INFORMATION: n may be an oxo-2'-C-bridged bicyclic cytidine
<220> FEATURE:
<221> NAME/KEY: misc_feature
<222> LOCATION: (14)..(15)
<223> OTHER INFORMATION: n may be an oxo-2'-C-bridged bicyclic thymidine

<400> SEQUENCE: 73
nnnnnngnnn gnnnna                                               16

<210> SEQ ID NO 74
<211> LENGTH: 16
<212> TYPE: DNA
<213> ORGANISM: Artificial Sequence
<220> FEATURE:
<223> OTHER INFORMATION: oligonucleotide 208a_1CBBN_DNA_PO
<220> FEATURE:
<221> NAME/KEY: misc_feature
<222> LOCATION: (9)..(9)
<223> OTHER INFORMATION: n may be an oxo-2'-C-bridged bicyclic thymidine

<400> SEQUENCE: 74 cttttttgcnc gtctta                                              16

<210> SEQ ID NO 75
<211> LENGTH: 16
<212> TYPE: DNA
<213> ORGANISM: Artificial Sequence
<220> FEATURE:
<223> OTHER INFORMATION: oligonucleotide 208a_1aminoCBBN_DNA_PO
<220> FEATURE:
<221> NAME/KEY: misc_feature
<222> LOCATION: (9)..(9)
<223> OTHER INFORMATION: n may be an amino-2'-C-bridged bicyclic
      thymidine

<400> SEQUENCE: 75 cttttttgcnc gtctta                                              16

<210> SEQ ID NO 76
<211> LENGTH: 16
```

```
<212> TYPE: DNA
<213> ORGANISM: Artificial Sequence
<220> FEATURE:
<223> OTHER INFORMATION: oligonucleotide 208a_2aminoCBBN_DNA_PO
<220> FEATURE:
<221> NAME/KEY: misc_feature
<222> LOCATION: (6)..(6)
<223> OTHER INFORMATION: n may be an amino-2'-C-bridged bicyclic
      thymidine
<220> FEATURE:
<221> NAME/KEY: misc_feature
<222> LOCATION: (9)..(9)
<223> OTHER INFORMATION: n may be an amino-2'-C-bridged bicyclic
      thymidine

<400> SEQUENCE: 76
cttttngcnc gtctta                                                    16

<210> SEQ ID NO 77
<211> LENGTH: 16
<212> TYPE: DNA
<213> ORGANISM: Artificial Sequence
<220> FEATURE:
<223> OTHER INFORMATION: oligonucleotide 208a_3aminoCBBN_DNA_PO
<220> FEATURE:
<221> NAME/KEY: misc_feature
<222> LOCATION: (5)..(6)
<223> OTHER INFORMATION: n may be an amino-2'-C-bridged bicyclic
      thymidine
<220> FEATURE:
<221> NAME/KEY: misc_feature
<222> LOCATION: (9)..(9)
<223> OTHER INFORMATION: may be an amino-2'-C-bridged bicyclic thymidine

<400> SEQUENCE: 77
ctttnngcnc gtctta                                                    16

<210> SEQ ID NO 78
<211> LENGTH: 16
<212> TYPE: DNA
<213> ORGANISM: Artificial Sequence
<220> FEATURE:
<223> OTHER INFORMATION: oligonucleotide 208a_2aminoCBBN_DNA_PO_isomer
<220> FEATURE:
<221> NAME/KEY: misc_feature
<222> LOCATION: (5)..(6)
<223> OTHER INFORMATION: n may be an amino-2'-C-bridged bicyclic
      thymidine

<400> SEQUENCE: 78
ctttnngctc gtctta                                                    16

<210> SEQ ID NO 79
<211> LENGTH: 16
<212> TYPE: DNA
<213> ORGANISM: Artificial Sequence
<220> FEATURE:
<223> OTHER INFORMATION: oligonucleotide 208a_10101
<220> FEATURE:
<221> NAME/KEY: misc_feature
<222> LOCATION: (1)..(1)
<223> OTHER INFORMATION: n may be an locked nucleic acid
      phosphorothioate cytidine
<220> FEATURE:
<221> NAME/KEY: misc_feature
<222> LOCATION: (2)..(4)
<223> OTHER INFORMATION: n may be a phosphorothioate thymidine
<220> FEATURE:
<221> NAME/KEY: misc_feature
<222> LOCATION: (5)..(6)
<223> OTHER INFORMATION: n may be an locked nucleic acid
      phosphorothioate thymidine
<220> FEATURE:
```

<221> NAME/KEY: misc_feature
<222> LOCATION: (7)..(7)
<223> OTHER INFORMATION: n may be a phosphorothioate guanosine
<220> FEATURE:
<221> NAME/KEY: misc_feature
<222> LOCATION: (8)..(8)
<223> OTHER INFORMATION: n may be an locked nucleic acid
    phosphorothioate cytidine
<220> FEATURE:
<221> NAME/KEY: misc_feature
<222> LOCATION: (9)..(9)
<223> OTHER INFORMATION: n may be a phosphorothioate thymidine
<220> FEATURE:
<221> NAME/KEY: misc_feature
<222> LOCATION: (10)..(10)
<223> OTHER INFORMATION: n may be an locked nucleic acid
    phosphorothioate cytidine
<220> FEATURE:
<221> NAME/KEY: misc_feature
<222> LOCATION: (11)..(11)
<223> OTHER INFORMATION: n may be an locked nucleic acid
    phosphorothioate guanosine
<220> FEATURE:
<221> NAME/KEY: misc_feature
<222> LOCATION: (12)..(12)
<223> OTHER INFORMATION: n may be a phosphorothioate thymidine
<220> FEATURE:
<221> NAME/KEY: misc_feature
<222> LOCATION: (13)..(13)
<223> OTHER INFORMATION: n may be an locked nucleic acid
    phosphorothioate cytidine
<220> FEATURE:
<221> NAME/KEY: misc_feature
<222> LOCATION: (14)..(14)
<223> OTHER INFORMATION: n may be a phosphorothioate thymidine
<220> FEATURE:
<221> NAME/KEY: misc_feature
<222> LOCATION: (15)..(15)
<223> OTHER INFORMATION: n may be an locked nucleic acid
    phosphorothioate thymidine
<220> FEATURE:
<221> NAME/KEY: misc_feature
<222> LOCATION: (16)..(16)
<223> OTHER INFORMATION: n may be a locked nucleic acid adenosine

<400> SEQUENCE: 79
nnnnnnnnnn nnnnnn                                                     16

<210> SEQ ID NO 80
<211> LENGTH: 16
<212> TYPE: DNA
<213> ORGANISM: Artificial Sequence
<220> FEATURE:
<223> OTHER INFORMATION: oligonucleotide 208a_10101_1aminoCBBN_PS
<220> FEATURE:
<221> NAME/KEY: misc_feature
<222> LOCATION: (1)..(1)
<223> OTHER INFORMATION: n may be an locked nucleic acid
    phosphorothioate cytidine
<220> FEATURE:
<221> NAME/KEY: misc_feature
<222> LOCATION: (2)..(4)
<223> OTHER INFORMATION: n may be a phosphorothioate thymidine
<220> FEATURE:
<221> NAME/KEY: misc_feature
<222> LOCATION: (5)..(6)
<223> OTHER INFORMATION: n may be an locked nucleic acid
    phosphorothioate thymidine
<220> FEATURE:
<221> NAME/KEY: misc_feature
<222> LOCATION: (7)..(7)
<223> OTHER INFORMATION: n may be a phosphorothioate guanosine
<220> FEATURE:
<221> NAME/KEY: misc_feature
<222> LOCATION: (8)..(8)
<223> OTHER INFORMATION: n may be an locked nucleic acid
    phosphorothioate cytidine

```
<220> FEATURE:
<221> NAME/KEY: misc_feature
<222> LOCATION: (9)..(9)
<223> OTHER INFORMATION: n may be a phosphorothioate thymidine
<220> FEATURE:
<221> NAME/KEY: misc_feature
<222> LOCATION: (10)..(10)
<223> OTHER INFORMATION: n may be an locked nucleic acid
     phosphorothioate cytidine
<220> FEATURE:
<221> NAME/KEY: misc_feature
<222> LOCATION: (11)..(11)
<223> OTHER INFORMATION: n may be an locked nucleic acid
     phosphorothioate guanosine
<220> FEATURE:
<221> NAME/KEY: misc_feature
<222> LOCATION: (12)..(12)
<223> OTHER INFORMATION: n may be a phosphorothioate thymidine
<220> FEATURE:
<221> NAME/KEY: misc_feature
<222> LOCATION: (13)..(13)
<223> OTHER INFORMATION: n may be an locked nucleic acid
     phosphorothioate cytidine
<220> FEATURE:
<221> NAME/KEY: misc_feature
<222> LOCATION: (14)..(14)
<223> OTHER INFORMATION: n may be a phosphorothioate thymidine
<220> FEATURE:
<221> NAME/KEY: misc_feature
<222> LOCATION: (15)..(15)
<223> OTHER INFORMATION: n may be an amino-2'-C-bridged bicyclic
     phosphorothioate thymidine
<220> FEATURE:
<221> NAME/KEY: misc_feature
<222> LOCATION: (16)..(16)
<223> OTHER INFORMATION: n may be a locked nucleic acid adenosine

<400> SEQUENCE: 80
nnnnnnnnnn nnnnnn                                                        16

<210> SEQ ID NO 81
<211> LENGTH: 16
<212> TYPE: DNA
<213> ORGANISM: Artificial Sequence
<220> FEATURE:
<223> OTHER INFORMATION: oligonucleotide 208a_10101_2minoCBBN_PS
<220> FEATURE:
<221> NAME/KEY: misc_feature
<222> LOCATION: (1)..(1)
<223> OTHER INFORMATION: n may be an locked nucleic acid
     phosphorothioate cytidine
<220> FEATURE:
<221> NAME/KEY: misc_feature
<222> LOCATION: (2)..(4)
<223> OTHER INFORMATION: n may be a phosphorothioate thymidine
<220> FEATURE:
<221> NAME/KEY: misc_feature
<222> LOCATION: (5)..(6)
<223> OTHER INFORMATION: n may be an amino-2'-C-bridged bicyclic
     phosphorothioate thymidine
<220> FEATURE:
<221> NAME/KEY: misc_feature
<222> LOCATION: (7)..(7)
<223> OTHER INFORMATION: n may be a phosphorothioate guanosine
<220> FEATURE:
<221> NAME/KEY: misc_feature
<222> LOCATION: (8)..(8)
<223> OTHER INFORMATION: n may be an locked nucleic acid
     phosphorothioate cytidine
<220> FEATURE:
<221> NAME/KEY: misc_feature
<222> LOCATION: (9)..(9)
<223> OTHER INFORMATION: n may be a phosphorothioate thymidine
<220> FEATURE:
<221> NAME/KEY: misc_feature
<222> LOCATION: (10)..(10)
<223> OTHER INFORMATION: n may be an locked nucleic acid
```

```
        phosphorothioate cytidine
<220> FEATURE:
<221> NAME/KEY: misc_feature
<222> LOCATION: (11)..(11)
<223> OTHER INFORMATION: n may be an locked nucleic acid
        phosphorothioate guanosine
<220> FEATURE:
<221> NAME/KEY: misc_feature
<222> LOCATION: (12)..(12)
<223> OTHER INFORMATION: n may be a phosphorothioate thymidine
<220> FEATURE:
<221> NAME/KEY: misc_feature
<222> LOCATION: (13)..(13)
<223> OTHER INFORMATION: n may be an locked nucleic acid
        phosphorothioate cytidine
<220> FEATURE:
<221> NAME/KEY: misc_feature
<222> LOCATION: (14)..(14)
<223> OTHER INFORMATION: n may be a phosphorothioate thymidine
<220> FEATURE:
<221> NAME/KEY: misc_feature
<222> LOCATION: (15)..(15)
<223> OTHER INFORMATION: n may be a locked nucleic acid thymidine
<220> FEATURE:
<221> NAME/KEY: misc_feature
<222> LOCATION: (16)..(16)
<223> OTHER INFORMATION: n may be a locked nucleic acid adenosine

<400> SEQUENCE: 81
nnnnnnnnnn nnnnnn                                                      16

<210> SEQ ID NO 82
<211> LENGTH: 16
<212> TYPE: DNA
<213> ORGANISM: Artificial Sequence
<220> FEATURE:
<223> OTHER INFORMATION: oligonucleotide 208a_1CBBN_DNA_PO
<220> FEATURE:
<221> NAME/KEY: misc_feature
<222> LOCATION: (9)..(9)
<223> OTHER INFORMATION: n may be an oxo-2'-C-bridged bicyclic thymidine

<400> SEQUENCE: 82 cttttttgcnc gtctta                                                     16

<210> SEQ ID NO 83
<211> LENGTH: 16
<212> TYPE: DNA
<213> ORGANISM: Artificial Sequence
<220> FEATURE:
<223> OTHER INFORMATION: oligonucleotide 208a_1aminoCBBN_DNA_PO
<220> FEATURE:
<221> NAME/KEY: misc_feature
<222> LOCATION: (9)..(9)
<223> OTHER INFORMATION: n may be an amino-2'-C-bridged bicyclic
        thymidine

<400> SEQUENCE: 83 cttttttgcnc gtctta                                                     16
```

BRIDGED BICYCLIC NUCLEOSIDES

RELATED APPLICATIONS

This Application is a National Stage application, filed pursuant to 35 U.S.C § 371, of International Application No. PCT/US2014/030100, filed on Mar. 16, 2014, which claims priority to and the benefit of U.S. Provisional Application No. 61/791,704, filed Mar. 15, 2013, which is hereby incorporated by reference in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: SeqListST25.txt, date recorded: Sep. 1, 2015, file size 24 kilobytes).

FIELD OF THE INVENTION

The present invention relates to modified nucleosides, nucleotides, and oligonucleotides having advantages in synthesis, potency, efficiency of delivery, target specificity, stability, and/or toxicity when administered to a patient.

BACKGROUND

Oligonucleotide chemistry patterns or motifs for antisense oligonucleotide inhibitors have the potential to improve the delivery, stability, potency, specificity, and/or toxicity profile of the inhibitors, and such are needed for effectively targeting RNA function in a therapeutic context.

SUMMARY OF THE INVENTION

The present invention relates to modified nucleosides, nucleotides, and oligonucleotides comprising at least one 2'-C-Bridged Bicyclic Nucleotide (CBBN), and pharmaceutical compositions comprising the modified oligonucleotides. The invention further provides methods of use and synthesis for these oligonucleotides, as well as synthetic intermediates. In various embodiments, the oligonucleotides are antisense inhibitors that provide advantages in potency, efficiency of delivery, target specificity, stability, and/or toxicity.

In one aspect, the present invention provides 2'-C-Bridged Bicyclic Nucleosides or Nucleotides (CBBN) having the structure of formula I:

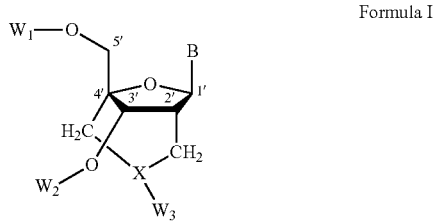

Formula I wherein X is N or S; $W_1$ and $W_2$ are independently H, an alcohol protecting group, phosphate ester, phosphorothioate ester, di- or tri-phosphate, or phosphoramidite; $W_3$ independently is null, H, O, an amine protecting group, phosphoramidite, phosphoramidate ester, phosphordiamidate ester, methyl, alkyl, cycloalkyl, carboxamide, a sugar, a fatty acid, or other conjugated molecules described herein, $—C_{1-4}(O)R$, or $—COOR$, wherein R is aryl, linear or cyclic alkyl or alkenyl, sugar, fatty acid, or other molecular conjugate such as a drug conjugate; B is a nucleobase. In some embodiments, the nucleobase is a pyrimidine base. In other embodiments, the nucleobase is a purine base.

In another aspect, the present invention provides oligonucleotides comprising at least one 2'-C-Bridged Bicyclic Nucleotide. The number of 2'-C-Bridged Bicyclic Nucleotides within the oligonucleotide may vary. For example, the number of 2'-C-Bridged Bicyclic Nucleotides may be at least about 10% of the nucleotides, at least about 25% of the nucleotides, at least about 50% of the nucleotides, or at least about 75% of the nucleotides. The length of the oligonucleotides may also vary. For example, the oligonucleotides of the present invention may be from about 5 to about 50 nucleotides in length or from about 10 to about 25 nucleotides in length. In other embodiments, the oligonucleotides may be less than about 10 nucleotides in length (e.g., from about 5 to about 10 nucleotides) or less than about 8 nucleotides in length (e.g., from about 5 to about 8 nucleotides).

The oligonucleotides may further include at least one nucleotide with a 2' modification selected from 2'-deoxy, 2'-O-methyl, 2'-fluoro, and a 2' to 4' bridge structure. In certain embodiments, the oligonucleotides further comprise backbone modifications such as phosphorothioate linkages and/or phosphorodiamidate linkages. In yet other embodiments, the oligonucleotides include at least one purine and/or pyrimidine base modifications. For example, the base modification may be at the C-5 position of a pyrimidine base and/or the C-8 position of a purine base. In some embodiments, the oligonucleotides include one or more morpholino nucleotides.

In various embodiments, the oligonucleotide comprises a nucleotide sequence that is at least substantially identical or complementary to a nucleotide sequence of a human microRNA. For example, the oligonucleotide may comprise a nucleotide sequence that is substantially complementary to a human miR-15a, miR-15b, miR-29, miR-92, miR-143, miR-145, miR-195, miR-206, miR-208a, miR-208b, miR-378, miR-451 and/or miR-499 sequence. In yet further embodiments, the oligonucleotide comprises a nucleotide sequence that is completely identical or complementary to a nucleotide sequence of a human microRNA. In various embodiments, the sequence of the oligonucleotide may be designed so as to mimic a miRNA or target a miRNA by antisense inhibition.

In another aspect, the present invention provides a pharmaceutical composition comprising an effective amount of the oligonucleotide described herein, or a pharmaceutically-acceptable salt thereof, and a pharmaceutically-acceptable carrier or diluent. The pharmaceutically-acceptable carrier may include a colloidal dispersion system, macromolecular complex, nanocapsule, microsphere, bead, oil-in-water emulsion, micelle, mixed micelle, or liposome. In an embodiment, the pharmaceutical composition is an aqueous formulation.

In yet another aspect, the present invention provides a method of reducing or inhibiting an RNA by antisense action, including reducing or inhibiting an mRNA target or microRNA target in a cell. The method comprises contacting a cell with the oligonucleotide disclosed herein. In various embodiments, the cell may be a mammalian cell. In one embodiment, the cell may be, for example, a heart cell. In another embodiment, the cell may be contacted with the oligonucleotide in vivo or er vivo.

In a further aspect, the present invention provides a method of preventing or treating a condition in a subject associated with or mediated by a microRNA, comprising administering to the subject a pharmaceutical composition comprising an oligonucleotide targeting a miRNA as described herein. In various embodiments, the pharmaceutical composition is administered by parenteral administration or by direct injection into target tissue. In other embodiments, the pharmaceutical composition is administered by oral, transdermal, sustained release, controlled release, delayed release, suppository, catheter, or sublingual administration.

In still another aspect, the present invention provides a method of synthesizing a 2'-C-Bridged Bicyclic Nucleoside, a 2'-C-Bridged Bicyclic Nucleotide or a corresponding phosphoramidite, or a 2'-C-Bridged Bicyclic Nucleotide-containing oligonucleotide. The method comprises using, for example, ribose as a starting material, converting to a methyl 4,4-bismesyloxymethyl-2-hydroxymethylfuranose derivative, followed by glycosylation of the derivative. The 2-hydroxymethyl group of the glycosylated material is then converted to a protected amine that is then cyclized on the alpha face of the nucleoside with the corresponding 4-mesyloxymethyl group to give a fully protected aza-bicyclic nucleoside that is readily converted to a nucleoside phosphoramidite via standard protecting group chemistry. Alternative methods for synthesis are described in a U.S. provisional patent application by Kurt Vagle, entitled "Synthesis of Bicyclic Nucleosides," filed Mar. 16, 2014, which is hereby incorporated by reference in its entirety.

Other aspects and embodiments of the invention will be apparent from the following detailed description and examples.

DESCRIPTION OF THE DRAWINGS

FIG. 4C illustrates the synthesis of an exemplary DMTr-protected fatty acid conjugated amine 2'-C-Bridged Bicyclic Nucleoside phosphoramidite. FIG. 4D illustrates the synthesis of an exemplary DMTr-protected sugar conjugated amine 2'-C-Bridged Bicyclic Nucleoside phosphoramidite.

FIG. 5A provides a comparison chart of the affinity increases ($\Delta T_{m, c}$/modification) for locked nucleoside (LNA), its aminoLNA counterpart, as well as 2'-O,4'-C-Ethylene-Bridged Nucleoside (oxoENA) and its aminoENA counterpart. FIG. 5B provides a comparison chart of the affinity increases ($\Delta T_{m, c}$/modification) for amine 2'-C-Bridged Bicyclic Nucleoside (aminoCBBN) with its oxoCBBN counterpart. As shown, amine 2'-C-Bridged Bicyclic Nucleoside imparts much more affinity per modification than its oxoCBBN counterpart. Additionally, single and multiple aminoCBBN modifications within an oligonucleotide impart affinities equal to or greater than those of LNA nucleosides.

DETAILED DESCRIPTION OF THE INVENTION

Figure 1:
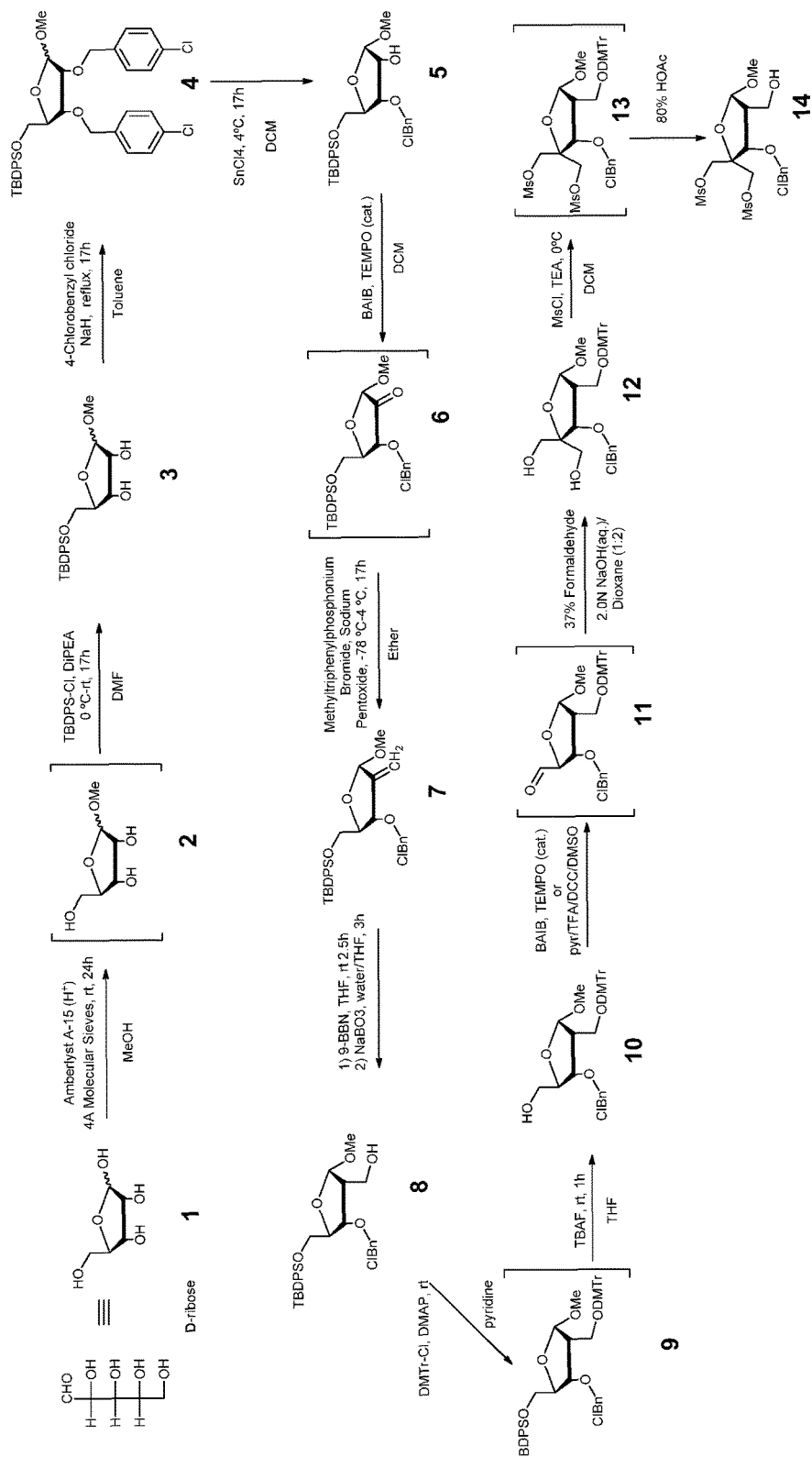
FIG. 1 illustrates the synthesis of an amine 2'-C-Bridged Bicyclic Nucleoside.
Figure 1:
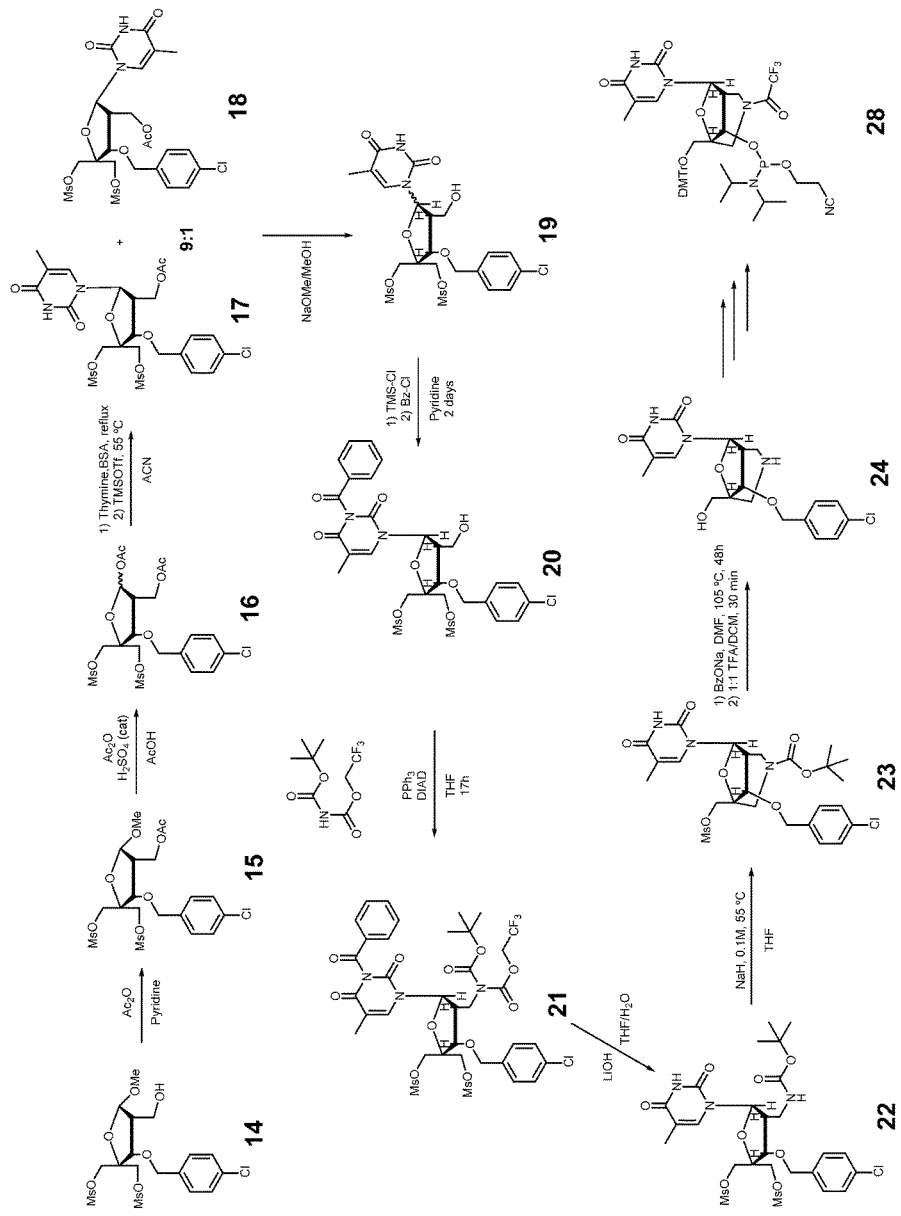
Figure 1:
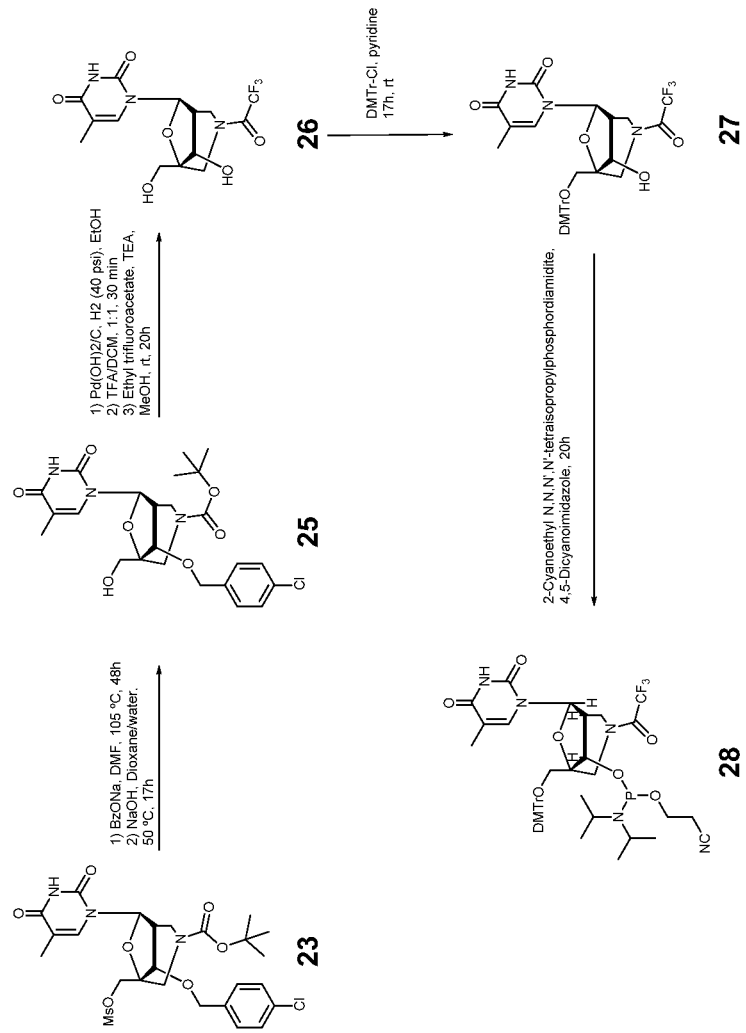

The present invention relates to 2'-C-Bridged Bicyclic Nucleosides and Nucleotides, and oligonucleotides comprising at least one 2'-C-Bridged Bicyclic Nucleotide. The invention further provides pharmaceutical compositions comprising the modified oligonucleotides, as well as methods of use and synthesis for these oligonucleotides.

The oligonucleotides of the present invention in various embodiments can provide advantages in synthesis, potency, efficiency of delivery, target specificity, stability, and/or toxicity. In an exemplary embodiment, the oligonucleotides of the invention provide novel conjugation strategies allowing for advantages in targeting cells or tissues by attaching a ligand and/or a drug compound, to the bridging moiety such as an amine. In another embodiment, the oligonucleotides of the invention provide therapeutic advantages in potency, stability, and/or toxicity.

In one aspect, the present invention provides 2'-C-Bridged Bicyclic Nucleosides or Nucleotides, or oligonucleotides having the structure of Formula I:

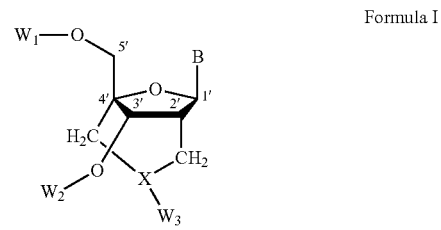

Formula I wherein X is N or S. In one embodiment, X is N. In another embodiment, X is S.

In various embodiments, $W_1$ and $W_2$ are independently H, an alcohol protecting group, phosphate ester, phosphorothioate ester, di- or tri-phosphate, or phosphoramidite. $W_3$ independently is null, H, O, an amine protecting group, phosphoramidite, phosphoramidate ester, phosphordiamidate ester, methyl, alkyl, cycloalkyl, carboxamide, a sugar, a fatty acid, or other conjugated molecules described herein, —$C_{1-4}$(O)R, or —COOR, wherein R is aryl, linear or cyclic alkyl or alkenyl, sugar, fatty acid, or other molecular conjugate such as a drug conjugate.

In various embodiments, the alcohol protecting group is selected from 4,4'-dimethoxytrityl, acetyl, silyl, or acid labile ether. In an embodiment. W and $W_2$ each is an alcohol protecting group independently selected from 4,4'-dimethoxytrityl, acetyl, silyl, or acid labile ether. In various embodiments, the amine protecting group is carbobenzyloxy (Cbz), p-methoxybenzyl carbonyl (Moz or MeOZ), tert-butyloxycarbonyl (BOC), 9-fluorenylmethyloxycarbonyl (FMOC), acetyl (Ac), benzoyl (Bz), benzyl (Bn), trifluoroacetyl (tfa). In an embodiment, $W_3$ is an amine protecting group selected from carboxybenzyl, tert-butoxycarbonyl, or trifluoroacetamidyl.

In various embodiments, 2'-C-Bridged Bicyclic Nucleoside is a 2'-deoxy-2'-C, 4'-C-Bridged Bicyclic Nucleoside (2'-CBBN).

In various embodiments, oxo-2'-C-Bridged Bicyclic Nucleoside is a 2'-deoxy-2'-C, 4'-C-Bridged Bicyclic Nucleoside, wherein 2'C and 4'C are connected through a oxygen resulting in a three atom linkage (—C—O—C—) (oxoCBBN).

In various embodiments, amino-2'-C-Bridged Bicyclic Nucleoside or aza-2'-Bridged Bicyclic Nucleoside is a 2'-deoxy-2'-C, 4'-C-Bridged Bicyclic Nucleoside, wherein 2'C and 4'C are connected through a nitrogen resulting in a three atom linkage (—C—N—C—) (aminoCBBN).

In various embodiments, thio-2'-C-Bridged Bicyclic Nucleoside is a 2'-deoxy-2'-C, 4'-C-Bridged Bicyclic Nucleoside, wherein 2'C and 4'C are connected through a sulfur resulting in a three atom linkage (—C—S—C—) (thioCBBN).

In various embodiments, amino-2'-C-Bridged Bicyclic Nucleotide and thio-2'-C-Bridged Bicyclic Nucleotide are phosphoesters of the amino-2'-C-Bridged Bicyclic Nucleosides and thio-2'-C-Bridged Bicyclic Nucleosides, respectively.

In various embodiments, locked nucleoside is a 2'-oxo-4'-C-Bridged Bicyclic Nucleoside (LNA) that has a 2 atom linkage between the 2' and 4' position of the nucleoside's ribose ring. The core sugar forms a 2,5-dioxabicyclo[2.2.1]heptane structure.

In various embodiments, ENA and oxoENA is a 2'-oxo-4'-C-Bridged Bicyclic Nucleoside that has a 3 atom linkage between the 2' and 4' position of the nucleoside's ribose ring. The core sugar forms a 2,6-dioxabicyclo[3.2.1]octane structure.

In various embodiments, aminoENA and azaENA is a 2'-aza-4'-C-Bridged Bicyclic Nucleoside that has a 3 atom linkage between the 2' and 4' position of the nucleoside's ribose ring. The core sugar forms 6-oxa-2-azabicyclo[3.2.1]octane structure.

In various embodiments, B is a nucleobase. The nucleobase or base can be a purine or a pyrimidine base, which may be modified. In one embodiment, the nucleobase is a purine base. In another embodiment, the nucleobase is a pyrimidine base. In various embodiments, the nucleobase can be selected from natural nucleosidic bases such as adenine, guanine, uracil, thymine, and cytosine, or derivatives and/or substitutes thereof. In addition, the present invention also contemplates the use of non-naturally occurring nucleobases. In certain embodiments, the non-naturally occurring nucleobase can be a base in which any of the ring atoms of the nucleobases is replaced by another atom. For example, CH may be replaced by N and vice versa. Such modifications can occur at more than one position. Another example of a non-naturally occurring base is a base in which the 2- and 4-substituents of a naturally occurring base are reversed. Additional purine and/or pyrimidine base modifications are described in WO 2012/061810, which is hereby incorporated by reference in its entirety. In some embodiments, the base modification is an amino carbonyl, such as a carboxamino, carbamoyl, or carbamide group. The modification in various embodiments is at the C-5 position of one or more pyrimidine bases, and/or at the C-8 position of one or more purine bases. Exemplary nucleobases include, but are not limited to, 9-N-adenine, 9-N-guanine, thymidine, cytidine, uridine, 5-methyl-cytosine, inosine, 5-substituted uridine, 5-substituted cytosine, 2-aminoadenosine or 5-methylcytosine.

In some embodiments, the 2'-C-Bridged Bicyclic Nucleotides may be positioned as locked nucleotides as described in WO 2012/083005 and U.S. Patent Publication No. 2013/0345288, which are incorporated by reference in their entireties. For example, the number and position of the 2'-C-Bridged Bicyclic Nucleotides may be such that the oligonucleotide reduces or inhibits miR-15a, miR-15b, miR-208a, miR-208b, and/or miR-499 activity at high potency. In certain embodiments, the oligonucleotide does not contain a stretch of nucleotides with more than four, or more than three, or more than two contiguous 2'-C-Bridged Bicyclic Nucleotides. In certain embodiments, the oligonucleotide does not contain a stretch of nucleotides with more than two contiguous non-2'-C-Bridged Bicyclic Nucleotides. For example, the oligonucleotide may have just one occurrence of contiguous non-2'-C-Bridged Bicyclic Nucleotides. In exemplary embodiments, the oligonucleotide has exactly 9 2'-C-Bridged Bicyclic Nucleotides and 7 non-2'-C-Bridged Bicyclic Nucleotides. For example, the pattern of 2'-C-Bridged Bicyclic Nucleotides may be such that at least positions 1, 6, 10, 13, and 15 are 2'-C-Bridged Bicyclic Nucleotides. In certain embodiments, at least positions 1, 5, 10, and 16 are 2'-C-Bridged Bicyclic Nucleotides. In certain embodiments, positions 1, 5, 6, 8, 10, 11, 13, 15, and 16 are 2'-C-Bridged Bicyclic Nucleotides, and the remaining positions are non-2'-C-Bridged Bicyclic Nucleotides. In other embodiments, positions 1, 3, 4, 5, 6, 8, 10, 13, 15, and 16 are 2'-C-Bridged Bicyclic Nucleotides, with the remaining positions being non-2'-C-Bridged Bicyclic Nucleotides. In still other embodiments, positions 1, 4, 5, 7, 9, 10, 12, 14, and 16 are 2'-C-Bridged Bicyclic Nucleotides, with remaining positions being non-2'-C-Bridged Bicyclic Nucleotides. The non-2'-C-Bridged Bicyclic Nucleotides may be non-locked nucleotides.

In some embodiments, the oligonucleotide is from about 5 to 50 nucleotides in length, from about 8 to 30 nucleotides in length, or from about 10 to 25 nucleotides in length, or from 12 to 16 nucleotides in length. In certain embodiments, the oligonucleotide is from about 5 to about 10 nucleotides in length, or about 5 to about 8 nucleotides in length. In certain embodiments, the oligonucleotide is about 8 nucleotides in length, about 9 nucleotides in length, about 10 nucleotides in length, about 11 nucleotides in length, about 12 nucleotides in length, about 13 nucleotides in length, about 14 nucleotides in length, about 15 nucleotides in length, or about 16 nucleotides in length. In certain embodiments, the oligonucleotide is about 16 nucleotides or less in length, about 12 nucleotides or less in length, about 10 nucleotides or less in length, or about 8 nucleotides or less in length. In some embodiments, the oligonucleotides of the present invention comprise at least 1, at least 3, at least 5, or at least 7 2'-C-Bridged Bicyclic Nucleotides. In some embodiments, the oligonucleotides of the present invention include only 1, 2, or 3 2'-C-Bridged Bicyclic Nucleotides. In certain embodiments, at least about 5%, at least about 10%, at least about 20%, at least about 25%, at least about 30%, at least about 40%, at least about 50%, at least about 60%, at least about 70%, at least about 75%, at least about 80%, at least about 90%, or 100% of the nucleotides are 2'-C-Bridged Bicyclic Nucleotides. In certain embodiments, the oligonucleotide is not fully comprised of 2'-C-Bridged Bicyclic Nucleotides. For example, embodiments described in this paragraph may be amino 2'-C-Bridged Bicyclic Nucleotides.

The oligonucleotides of the present invention may be DNA- or RNA-based, and/or may employ one or more nucleic acid modifications, for example, such as a modified oligonucleotide backbone or one or more modified nucleoside units. The oligonucleotide or derivative may have one or more single stranded and/or one or more double stranded regions. The oligonucleotide may be an antisense oligonucleotide, short interfering RNA (siRNA), double stranded RNA (dsRNA), single stranded RNA (ssRNA), microRNA (miRNA), short hairpin RNA (shRNA), or ribozyme.

In certain embodiments, the oligonucleotides of the present invention comprise at least one nucleotide having purine and/or pyrimidine base modifications as described in WO 2012/061810, which is hereby incorporated by reference in its entirety. In some embodiments, the base modification is generally an amino carbonyl, such as a carboxamino, carbamoyl, or carbamide group. The modification in various embodiments is at the C-5 position of one or more pyrimidine bases, and/or at the C-8 position of one or more purine bases.

In some embodiments, the oligonucleotide further comprises at least one nucleotide with a 2' modification. As used herein, the term "2' modification" includes any 2' group other than OH. In some embodiments the 2' modification may be independently selected from O-alkyl (which may be substituted), halo, deoxy (H), and a 2' to 4' methoxy bridged nucleotide. For example, the 2' modifications may each be independently selected from O-methyl and fluoro. In exemplary embodiments, purine nucleotides each have a 2' OMe and pyrimidine nucleotides each have a 2' F. In certain embodiments, from one to about five 2' positions, or from about one to about three 2' positions are left unmodified (e.g., as 2' hydroxyls).

The 2' modifications in accordance with the invention may be selected from small hydrocarbon substituents. The hydrocarbon substituents include alkyl, alkenyl, alkynyl, and alkoxyalkyl, where the alkyl (including the alkyl portion of alkoxy), alkenyl and alkynyl may be substituted or unsubstituted. The alkyl, alkenyl, and alkynyl may be C1 to C10 alkyl, alkenyl or alkynyl, such as C1, C2, or C3. The hydrocarbon substituents may include one or two or three non-carbon atoms, which may be independently selected from N, O, and/or S. The 2' modifications may further include the alkyl, alkenyl, and alkynyl as O-alkyl, O-alkenyl, and O-alkynyl.

Exemplary 2' modifications in accordance with the invention include 2'-O-alkyl (C1-3 alkyl, such as 2'OMe or 2'OEt), 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA) substitutions.

In certain embodiments, the oligonucleotide contains at least one 2'-halo modification (e.g., in place of a 2' hydroxyl), such as 2'-fluoro, 2'-chloro, 2'-bromo, and 2'-iodo. In some embodiments, the 2' halo modification is fluoro. The oligonucleotide may contain from one to about five 2'-halo modifications (e.g., fluoro), or from one to about three 2'-halo modifications (e.g., fluoro). In some embodiments, the oligonucleotide contains all 2'-fluoro nucleotides at non-2'-C-Bridged Bicyclic Nucleotides positions. In certain embodiments, the 2'-fluoro groups are independently di-, tri-, or un-methylated.

The oligonucleotide may have one or more 2'-deoxy modifications (e.g., H for 2' hydroxyl), and in some embodiments, contains from about one to about ten 2'-deoxy modifications.

The oligonucleotides of the invention may further include at least one locked nucleotide (LNA), as described, for example, in U.S. Pat. Nos. 6,268,490, 6,316,198, 6,403,566, 6,770,748, 6,998,484, 6,670,461, and U.S. Pat. No. 7,034,133, all of which are hereby incorporated by reference in their entireties. In one embodiment, the oligonucleotide contains one or more LNAs having the structure shown by structure A below. Alternatively or in addition, the oligonucleotide contains one or more LNAs having the structure shown by structure B below.

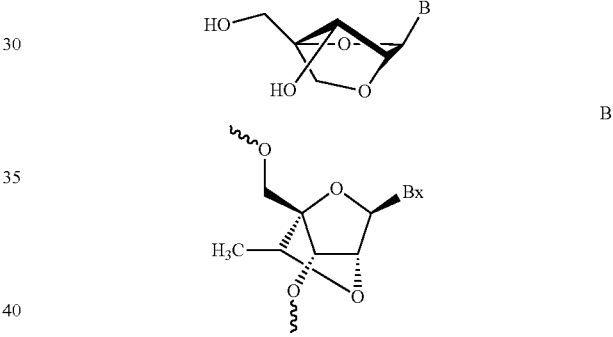

Other suitable locked nucleotides that can be incorporated in the oligonucleotides of the invention include those described in U.S. Pat. Nos. 6,403,566 and 6,833,361, both of which are hereby incorporated by reference in their entireties.

In certain embodiments, the oligonucleotide further comprises at least one terminal modification or "cap". The cap may be a 5' and/or a 3'-cap structure. The terms "cap" or "end-cap" include chemical modifications at either terminus of the oligonucleotide (with respect to terminal ribonucleotides), and including modifications at the linkage between the last two nucleotides on the 5' end and the last two nucleotides on the 3' end. The cap structure as described herein may increase resistance of the oligonucleotide to exonucleases without compromising molecular interactions with the RNA target or cellular machinery. Such modifications may be selected on the basis of their increased potency in vitro or in vivo. The cap can be present at the 5'-terminus (5'-cap) or at the 3'-terminus (3'-cap) or can be present on both ends. In certain embodiments, the 5'- and/or 3'-cap is independently selected from phosphorothioate monophosphate, abasic residue (moiety), phosphorothioate linkage, 4'-thio nucleotide, carbocyclic nucleotide, phosphorodithioate linkage, inverted nucleotide or inverted abasic moiety (2'-3' or 3'-3'), phosphorodithioate monophosphate, and methylphosphonate moiety. The phosphorothioate or phosphorodithioate linkage(s), when part of a cap structure, are generally positioned between the two terminal nucleotides on the 5' end and the two terminal nucleotides on the 3' end.

In certain embodiments, the oligonucleotides have at least one terminal phosphorothioate monophosphate. The phosphorothioate monophosphate may be at the 5' and/or 3' end of the oligonucleotide. A phosphorothioate monophosphate is defined by the following structures, where B is base, and R is a 2' modification as described above:

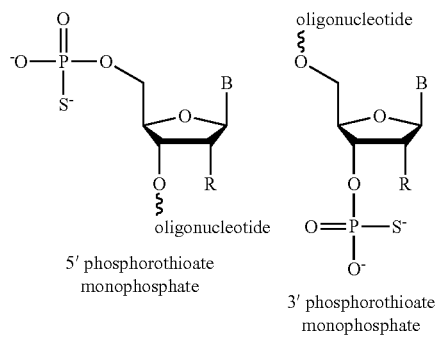

5' phosphorothioate monophosphate

3' phosphorothioate monophosphate

Phosphorothioate linkages may be present in some embodiments, such as between the last two nucleotides on the 5' and the 3' end (e.g., as part of a cap structure), or as alternating with phosphodiester bonds. In these or other embodiments, the oligonucleotide may contain at least one terminal abasic residue at either or both the 5' and 3' ends. An abasic moiety does not contain a commonly recognized purine or pyrimidine nucleotide base, such as adenosine, guanine, cytosine, uracil or thymine. Thus, such abasic moieties lack a nucleotide base or have other non-nucleotide base chemical groups at the 1' position. For example, the abasic nucleotide may be a reverse abasic nucleotide, e.g., where a reverse abasic phosphoramidite is coupled via a 5' amidite (instead of 3' amidite) resulting in a 5'-5' phosphate bond. The structure of a reverse abasic nucleoside for the 5' and the 3' end of a polynucleotide is shown below.

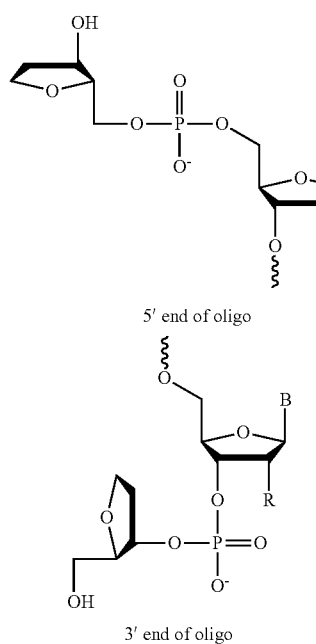

5' end of oligo

3' end of oligo

The oligonucleotide may contain one or more phosphorothioate linkages. Phosphorothioate linkages have been used to render oligonucleotides more resistant to nuclease cleavage. For example, the polynucleotide may be partially phosphorothioate-linked, for example, phosphorothioate linkages may alternate with phosphodiester linkages. In certain embodiments, however, the oligonucleotide is fully phosphorothioate-linked. In other embodiments, the oligonucleotide has from one to five or one to three phosphate linkages. In further embodiments, a 2'-C-Bridged Bicyclic Nucleotides are phosphorothioate linked.

In yet other embodiments, the oligonucleotides may include one or more modified phosphate linkages. Exemplary modified phosphate linkages are depicted below as Formulas II and III:

Formula II

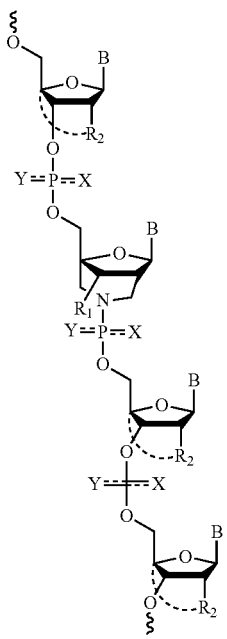

Formula III

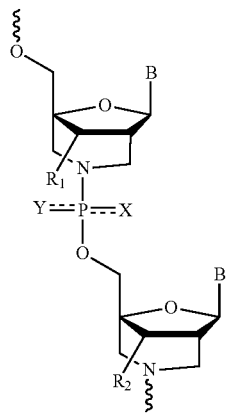

Figure 2:
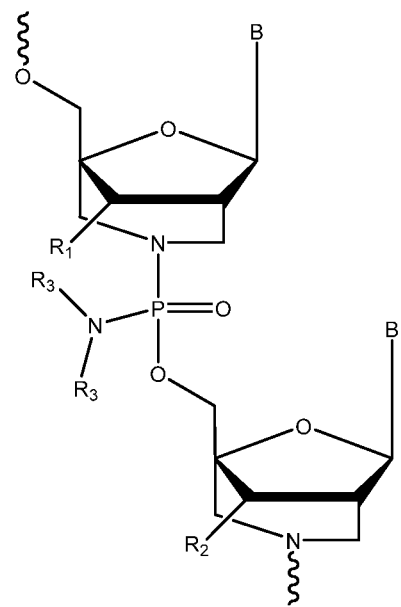
FIG. 2 illustrates 2'-C-Bridged Bicyclic Nucleosides linked by a phosphorodiamidate linkage.
Figure 3A:
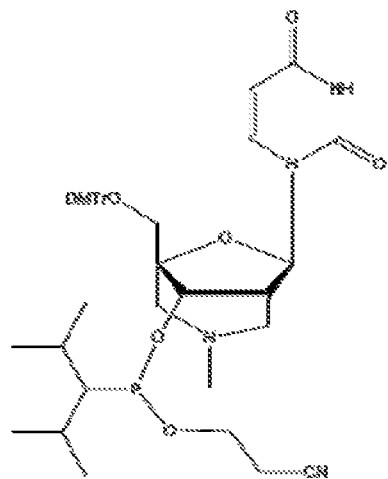
FIG. 3A illustrates an exemplary dimethoxytrityl (DMTr)-protected amine 2'-C-Bridged Bicyclic Nucleoside phosphoramidite.
Figure 3B:
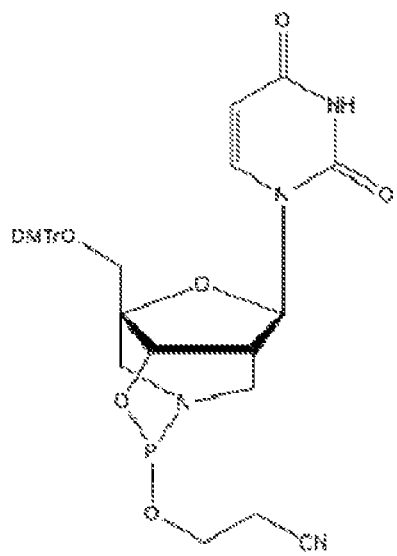
FIG. 3B illustrates an internal phosphoramidite derivative of a DMTr-protected amine 2'-C-Bridged Bicyclic Nucleoside.
Figure 3C:
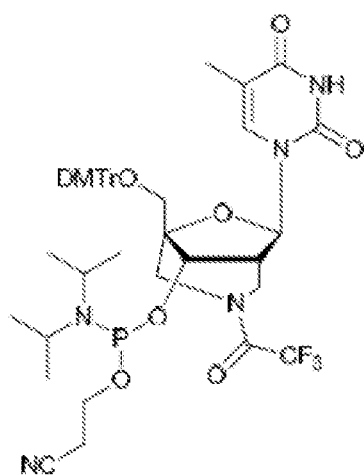
FIG. 3C illustrates an exemplary DMTr- and trifluoroacetate-protected amine 2'-C-Bridged Bicyclic Nucleoside phosphoramidite.
Figure 3D:
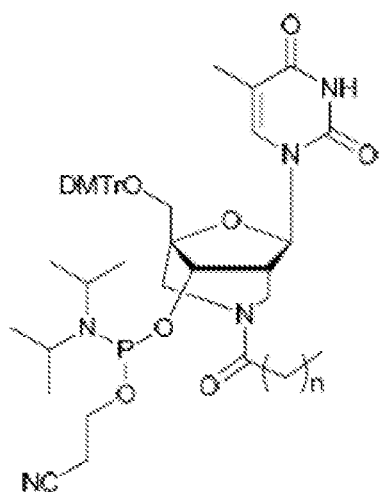
FIG. 3D illustrates an exemplary DMTr-protected fatty acid conjugated amine 2'-C-Bridged Bicyclic Nucleoside phosphoramidite.
Figure 3E:
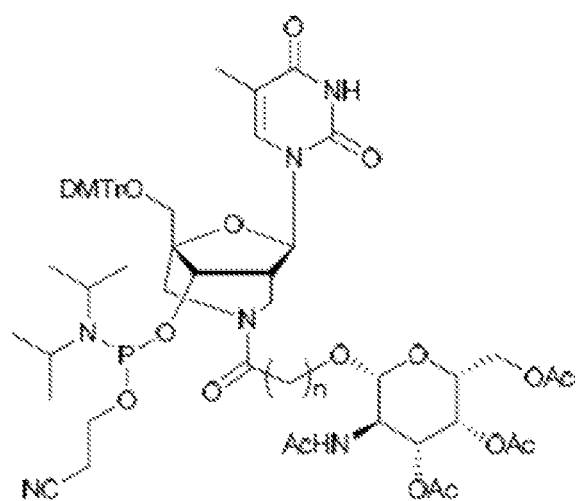
FIG. 3E illustrates an exemplary DMTr-protected sugar conjugated amine 2'-C-Bridged Bicyclic Nucleoside phosphoramidite.

As shown, $R_1$ and R2 are independently selected from H, alkyl, alkenyl, oxo, aryl, benzyl, halogen, —OH, —NH2, alkoxy, an alcohol protecting group, or an amine protecting group, and with respect to formula II, a bicyclic linkage such as LNA, or 2'-C-Bridged Bicyclic Nucleoside. X and Y are independently selected from H, O, S, —CO$_2$H, alkyl, alkenyl, aryl, benzyl carboxylate. —N(alkyl)$_2$, —N(alkenyl)$_2$, —N(aryl)$_2$, —N(benzyl)$_2$, —NH$_2$, —BH$_2$, or borate ester. B may be an independently selected nucleobase such as a purine or pyrimidine base, which may be modified. As shown, the polynucleotide may be partially phosphorodiamidate-linked (as shown in FIG. 2). In certain embodiments, however, the oligonucleotide is fully phosphorodiamidate linked. In other embodiments, the oligonucleotide has from one to five or one to three phosphate linkages. In further embodiments, 2'-C-Bridged Bicyclic Nucleotides are all linked by modified phosphate linkages (as shown in Formulas II and III).

In yet a further embodiment, the oligonucleotide may include one or more morpholino nucleotides. The morphlino nucleotides may be linked to 2'-C-Bridged Bicyclic Nucleosides as exemplified below in Formula IV:

Formula IV

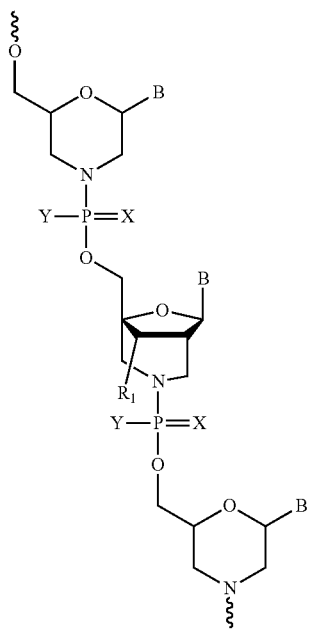

As shown in formula IV, $R_1$ is independently selected from H, alkyl, alkenyl, oxo, aryl, benzyl, halogen, OH, —NH2, alkoxy, an alcohol protecting group, or an amine protecting group. X and Y are independently selected from H, O, S, —CO$_2$H, alkyl, alkenyl, aryl, benzyl carboxylate, —N(alkyl)$_2$, —N(alkenyl)$_2$, —N(aryl)$_2$, —N(benzyl)$_2$, —NH$_2$, —BH$_2$, or Borate ester. B may be an independently selected nucleobase such as a purine or pyrimidine base, which may be modified.

The oligonucleotides disclosed herein may have a nucleotide sequence designed to inhibit an RNA molecule, including an mRNA or miRNA. In some embodiments, the oligonucleotide has a base sequence to mimic or target a mature miRNA, such as a mature miRNA listed in Table 1 below. The oligonucleotides may in these or other embodiments, be designed to target the pre- or pri-miRNA forms. In some embodiments, the oligonucleotides are substantially complementary to a nucleotide sequence of a human miRNA sequence. In further embodiments, the oligonucleotides are substantially identical to a nucleotide sequence of a human miRNA sequence. Exemplary oligonucleotides are at least partially complementary (i.e., at least about 60%, at least about 65%, at least about 70%, at least about 75%, at least about 80%, at least about 85%, at least about 95%, or 100% complementary) to a target miRNA sequence, such as a mature miRNA sequence listed in Table 1 below. Such antisense and sense sequences may be incorporated into shRNAs or other RNA structures containing stem and loop portions, for example. Such sequences are useful for, among other things, mimicking or targeting miRNA function for treatment or ameliorating cardiac hypertrophy, myocardial infarction, heart failure (e.g., congestive heart failure), vascular damage, and/or pathologic cardiac fibrosis, among others. Exemplary miRNA therapeutic utilities are disclosed in the US and PCT patent references listed in Table 2 below, each of which is hereby incorporated by reference in its entirety. The mature and pre-processed forms of miRNAs are disclosed in the patent references listed below, and such descriptions are also hereby incorporated by reference.

TABLE 1

| miRNA | miRNA Sequence | Reference |
|---|---|---|
| 1 | UGGAAUGUAAAGAAGUAUGUAU (SEQ ID No. 1) | WO 2009/012468 |
| 100 | AACCCGUAGAUCCGAACUUGUG (SEQ ID No. 2) | WO 2009/012468 |
| 10b | UACCCUGUAGAACCGAAUUUGUG (SEQ ID No. 3) | WO 2009/012468 |
| 125b | UCCCUGAGACCCUAACUUGUGA (SEQ ID No. 4) | WO 2009/012468 |
| 128 | UCACAGUGAACCGGUCUCUUU (SEQ ID No. 5) | WO 2007/070483 |
| 133a | UUUGGUCCCCUUCAACCAGCUG (SEQ ID No. 6) | WO 2009/012468 |
| 133b | UUUGGUCCCCUUCAACCAGCUA (SEQ ID No. 7) | WO 2009/012468 |
| 139 | UCUACAGUGCACGUGUCUCCAG (SEQ ID No. 8) | WO 2009/012468 |
| 143 | UGAGAUGAAGCACUGUAGCUC (SEQ ID No. 9) | WO 2007/070483 |
| 145 | GUCCAGUUUUCCCAGGAAUCCCU (SEQ ID No. 10) | WO 2007/070483 |
| 150 | UCUCCCAACCCUUGUACCAGUG (SEQ ID No. 11) | WO 2009/012468 |
| 15a | UAGCAGCACAUAAUGGUUUGUG (SEQ ID No. 12) | WO 2009/062169 |

TABLE 1-continued

| miRNA | miRNA Sequence | Reference |
|---|---|---|
| 15b | UAGCAGCACAUCAUGGUUUACA (SEQ ID No. 13) | WO 2009/062169 |
| 16 | UAGCAGCACGUAAAUAUUGGCG (SEQ ID No. 14) | WO 2009/062169 |
| 181b | AACAUUCAUUGCUGUCGGUGGGU (SEQ ID No. 15) | WO 2009/012468 |
| 195 | UAGCAGCACAGAAAUAUUGGC (SEQ ID No. 16) | WO 2009/012468 |
| 197 | UUCACCACCUUCUCCACCCAGC (SEQ ID No. 17) | WO 2009/012468 |
| 199a | CCCAGUGUUCAGACUACCUGUUC (SEQ ID No. 18) | WO 2009/012468 |
| 199b | miR-199b-5p CCCAGUGUUUAGACUAUCUGUUC (SEQ ID No. 19) miR-199b-3p ACAGUAGUCUGCACAUUGGUUA (SEQ ID No. 20) | WO 2010/135570 |
| 206 | UGGAAUGUAAGGAAGUGUGUGG (SEQ ID No. 21) | WO 2007/070483 |
| 208a | AUAAGACGAGCAAAAAGCUUGU (SEQ ID No. 22) | WO 2008/016924 |
| 208b | AUAAGACGAACAAAAGGUUUGU (SEQ ID No. 23) | WO 2009/018492 |
| 20a | UAAAGUGCUUAUAGUGCAGGUAG (SEQ ID No. 24) | US 60/950,565 |
| 21 | UAGCUUAUCAGACUGAUGUUGA (SEQ ID No. 25) | WO 2009/058818 |
| 214 | ACAGCAGGCACAGACAGGCAGU (SEQ ID No. 26) | US 61/047,005 |
| 22 | AAGCUGCCAGUUGAAGAACUGU (SEQ ID No. 27) | WO 2009/012468 |
| 221 | AGCUACAUUGUCUGCUGGGUUUC (SEQ ID No. 28) | WO 2009/012468 |
| 222 | AGCUACAUCUGGCUACUGGGU (SEQ ID No. 29) | WO 2009/012468 |
| 224 | CAAGUCACUAGUGGUUCCGUU (SEQ ID No. 30) | WO 2009/012468 |
| 23a | AUCACAUUGCCAGGGAUUUCC (SEQ ID No. 31) | WO 2009/012468 |
| 26a | UUCAAGUAAUCCAGGAUAGGCU (SEQ ID No. 32) | WO 2007/070483 |
| 26b | UUCAAGUAAUUCAGGAUAGGU (SEQ ID No. 33) | WO 2009/012468 |
| 28 | AAGGAGCUCACAGUCUAUUGAG (SEQ ID No. 34) | WO 2009/012468 |
| 29a | UAGCACCAUCUGAAAUCGGUUA (SEQ ID No. 35) | WO 2009/018493 |
| 29b | UAGCACCAUUUGAAAUCAGUGUU (SEQ ID No. 36) | WO 2009/018493 |
| 29c | UAGCACCAUUUGAAAUCGGUUA (SEQ ID No. 37) | WO 2009/018493 |
| 30a | UGUAAACAUCCUCGACUGGAAG (SEQ ID No. 38) | WO 2010/120969 |
| 30b | UGUAAACAUCCUACACUCAGCU (SEQ ID No. 39) | WO 2010/120969 |
| 30c | UGUAAACAUCCUACACUCUCAGC (SEQ ID No. 40) | WO 2009/012468 |
| 30d | UGUAAACAUCCCCGACUGGAAG (SEQ ID No. 41) | WO 2010/120969 |
| 30e | UGUAAACAUCCUUGACUGGAAG (SEQ ID No. 42) | WO 2010/120969 |
| 342-3p | UCUCACACAGAAAUCGCACCCGU (SEQ ID No. 43) | WO 2009/012468 |
| 382 | GAAGUUGUUCGUGGUGGAUUCG (SEC) ID No. 44) | WO 2009/012468 |
| 422a | ACUGGACUUAGGGUCAGAAGGC (SEQ ID No. 45) | US 2009/0226375 |
| 378 | ACUGGACUUGGAGUCAGAAGG (SEQ ID No. 46) | WO 2009/012468 |
| 424 | CAGCAGCAAUUCAUGUUUUGAA (SEQ ID No. 47) | WO 2009/062169 |
| 483-3p | UCACUCCUCUCCUCCCGUCUU (SEQ ID No. 48) | WO 2009/012468 |
| 484 | UCAGGCUCAGUCCCCUCCCGAU (SEQ ID No. 49) | WO 2009/012468 |
| 486-5p | UCCUGUACUGAGCUGCCCCGAG (SEQ ID No. 50) | WO 2009/012468 |

TABLE 1-continued

| miRNA | miRNA Sequence | Reference |
|---|---|---|
| 497 | CAGCAGCACACUGUGGUUUGU (SEQ ID No. 51) | WO 2009/062169 |
| 499 | UUAAGACUUGCAGUGAUGUUU (SEQ ID No. 52) | WO 2009/018492 |
| 542-5p | UCGGGGAUCAUCAUGUCACGAGA (SEQ ID No. 53) | WO 2009/012468 |
| 92a | UAUUGCACUUGUCCCGGCCUGU (SEQ ID No. 54) | WO 2009/012468 |
| 92b | UAUUGCACUCGUCCCGGCCUCC (SEQ ID No. 55) | WO 2009/012468 |
| let-7a | UGAGGUAGUAGGUUGUAUAGUU (SEQ ID No. 56) | WO 2009/012468 |
| let-7b | UGAGGUAGUAGGUUGUGUGGUU (SEQ ID No. 57) | WO 2009/012468 |
| let-7c | UGAGGUAGUAGGUUGUAUGGUU (SEQ ID No. 58) | WO 2009/012468 |
| let-7d | AGAGGUAGUAGGUUGCAUAGUU (SEQ ID No. 59) | WO 2009/012468 |
| let-7e | UGAGGUAGGAGGUUGUAUAGUU (SEQ ID No. 60) | WO 2009/012468 |
| let-7f | UGAGGUAGUAGAUUGUAUAGUU (SEQ ID No. 61) | WO 2009/012468 |
| let-7g | UGAGGUAGUAGUUUGUACAGUU (SEQ ID No. 62) | WO 2009/012468 |
| 451 | AAACCGUUACCAUUACUGAGUU (SEQ ID No. 63) | WO 2010/129950 |

TABLE 2

| miRNA | Direction of Modulation | Indications | Reference |
|---|---|---|---|
| miR-208a/miR-208b/miR-499 | Antagonist | Pathologic cardiac hypertrophy, myocardial infarction, heart failure | WO 2008/016924 (208a) WO 2009/018492 (208b/499) |
| miR-208a/miR-208b | Antagonist | Metabolic Disorders (obesity, hyperlipidemia, diabetes, metabolic syndrome, hypercholesterolemia; hepatic steatosis) | PCT/US2012/059349 |
| miR-15/miR-16/miR-195 | Antagonist | Pathologic cardiac hypertrophy, myocardial infarction, heart failure | WO 2009/062169 |
| miR-29 | Agonist | Tissue fibrosis (cardiac, pulmonary, hepatic, kidney) | WO 2009/018493 |
| miR-29 | Antagonist | profibrotic agents to convert soft plaques to fibrotic tissue | WO 2009/018493 |
| miR-126 | Agonist | promotes angiogenesis, vascular integrity, and vascular repair | WO 2010/019574 |
| miR-126 | Antagonist | pathologic vascularization | WO 2010/019574 |
| miR-206 | Agonist | Muscle injury | WO 2007/070483 |
| miR-206/miR-1 | Agonist | Denervating neuropathic states (ALS, spinal cord injury, myasthenia gravis) | WO 2009/117418 |
| miR-143 | Agonist | Restenosis/neointima formation | WO 2009/105759 |
| miR-1/miR-133 | Agonist/Antagonist | Muscle injury (antagonist/agonist of each miRNA applied in combination at different times) | WO 2007/070483 |
| miR-451 | Antagonist | Polycythemia | WO 2012/148373 |
| miR-451 | Agonist | Anemia | WO 2012/148373 |
| miR-378/miR-378* | Antagonist | Metabolic disorders (obesity, hyperlipidemia, diabetes, metabolic syndrome, hypercholesterolemia; hepatic steatosis); Pathologic cardiac hypertrophy, myocardial infarction, heart failure | WO 2011/153542 |

TABLE 2-continued

| miRNA | Direction of Modulation | Indications | Reference |
|---|---|---|---|
| miR-92 | Antagonist | Promotes angiogenesis and vessel repair | US 2010/0324118 A1 |
| miR-92 | Agonist | Inhibits tumor angiogenesis | US 2010/0324118 A1 |
| miR-34a | Antagonist | Myocardial infarction | US 2012/0238619 A1 |
| miR-145 | Antagonist | Pulmonary arterial hypertension | WO 2012/153135 |
| miR-33 | Antagonist | Statin-induced hepatotoxicity, cholestasis, increasing HDL cholesterol | US 20110281933 A1 |

In some embodiments, the oligonucleotides comprise a sequence that is substantially complementary to a nucleotide sequence of miR-15a or b, miR-29, miR-92, miR-143, miR-145, miR-195, miR-206, miR-208a, miR-208b, miR-378, miR-451 and/or miR-499. In exemplary embodiments, the oligonucleotides may comprise a sequence that is substantially complementary to a human miR-208a, miR-208b, miR-378, miR-451 and/or miR-499 sequence. In certain embodiments, the oligonucleotides may comprise a sequence that is substantially identical to a human miR-208a, miR-208b, miR-378, miR-451 and/or miR-499 sequence. As used herein, "substantially complementary" or "substantially identical" refers to a sequence that is at least about 70%, about 75%, about 80%, about 85%, about 90%, about 91%, about 92%, about 93%, about 94%, about 95%, about 96%, about 97%, about 98%, or about 99% complementary or identical to a target polynucleotide sequence.

The present invention further provides a method of synthesizing a 2'-C-Bridged Bicyclic Nucleoside, a 2'-C-Bridged Bicyclic Nucleotide or a corresponding phosphoramidite, or a 2'-C-Bridged Bicyclic Nucleotide-containing oligonucleotide. The method comprises using, for example, ribose as a starting material, converting to a methyl 4,4-bismesyloxymethyl-2-hydroxymethylfuranose derivative, followed by glycosylation of the derivative. The 2-hydroxymethyl group of the glycosylated material is then converted to a protected amine that is then cyclized on the alpha face of the nucleoside with the corresponding 4-mesyloxymethyl group to give a fully protected aza-bicyclic nucleoside that is readily converted to a nucleoside phosphoramidite via standard protecting group chemistry. Exemplary synthetic schemes for the 2'-C-Bridged Bicyclic Nucleoside are shown herein. Alternative methods for synthesis are described in a U.S. provisional patent application by Kurt Vagle, entitled "Synthesis of Bicyclic Nucleosides," filed Mar. 16, 2014, which is hereby incorporated by reference in its entirety.

The synthesis of oligonucleotides, including modified polynucleotides, by solid phase synthesis is well known and is reviewed by Caruthers et al., "New Chemical Methods for Synthesizing Polynucleotides," *Nucleic Acids Symp. Ser.*, (7):215-23 (1980) which is hereby incorporated by reference in its entirety. The synthesis of oligonucleotides will vary depending on the selected nucleotide monomer(s) utilized. In exemplary embodiments, the nucleotide monomers used for synthesis include, but are not limited to, dimethoxytrityl (DMTr)-protected amine 2'-C-Bridged Bicyclic Nucleoside phosphoramidite, an internal phosphoramidite derivative of a DMTr-protected amine 2'-C-Bridged Bicyclic Nucleoside, DMTr- and trifluoroacetate-protected amine 2'-C-Bridged Bicyclic Nucleoside phosphoramidite, DMTr-protected fatty acid conjugated amine 2'-C-Bridged Bicyclic Nucleoside phosphoramidite, and DMTr-protected sugar conjugated amine 2'-C-Bridged Bicyclic Nucleoside phosphoramidite (see FIGS. 3A-3E, respectively). In certain embodiments, extended coupling time may be required for oligonucleotide synthesis utilizing dimethoxytrityl (DMTr)-protected amine 2'-C-Bridged Bicyclic Nucleoside phosphoramidite, DMTr- and trifluoroacetate-protected amine 2'-C-Bridged Bicyclic Nucleoside phosphoramidite, DMTr-protected fatty acid conjugated amine 2'-C-Bridged Bicyclic Nucleoside phosphoramidite, and DMTr-protected sugar conjugated amine 2'-C-Bridged Bicyclic Nucleoside phosphoramidite. In certain embodiments, for oligonucleotide synthesis involving an internal phosphoramidite derivative of a DMTr-protected amine 2'-C-Bridged Bicyclic Nucleoside, the standard oligonucleotide synthesis cycle may be modified by replacing the normal capping reagent utilizing $Ac_2O$/base with a non-standard capping reagent. Alternatively, synthesis may be modified by treating the newly coupled oligonucleotide with an amine reactive conjugate or protecting group that is stable to the synthesis cycle (but if desired, can be removed later) immediately after the phosphoramidite coupling cycle, but before the standard capping step.

The oligonucleotide may be incorporated within a variety of macromolecular assemblies or compositions. Such complexes for delivery may include a variety of liposomes, nanoparticles, and micelles, formulated for delivery to a patient. The complexes may include one or more fusogenic or lipophilic molecules to initiate cellular membrane penetration. Such molecules are described, for example, in U.S. Pat. Nos. 7,404,969 and 7,202,227, which are hereby incorporated by reference in their entireties. Alternatively, the oligonucleotide may further comprise a pendant lipophilic group to aid cellular delivery, such as those described in WO 2010/129672, which is hereby incorporated by reference.

In another aspect, the present invention relates to a pharmaceutical composition which comprises an effective amount of the oligonucleotide of the present invention or a its pharmaceutically-acceptable salt thereof, and a pharmaceutically-acceptable carrier or diluent.

The composition or formulation may employ a plurality of therapeutic oligonucleotides, including at least one described herein. For example, the composition or formulation may employ at least about 2, about 3, about 4, or about 5 miRNA inhibitors described herein.

The oligonucleotides of the invention may be formulated as a variety of pharmaceutical compositions. Pharmaceutical compositions will be prepared in a form appropriate for the intended application. Generally, this entails preparing compositions that are essentially free of pyrogens, as well as other impurities that could be harmful to humans or animals. Exemplary delivery/formulation systems include colloidal dispersion systems, macromolecule complexes, nanocapsules, microspheres, beads, and lipid-based systems including oil-in-water emulsions, micelles, mixed micelles, and liposomes. Commercially available fat emulsions that are suitable for delivering the nucleic acids of the invention to cardiac and skeletal muscle tissues include Intralipid®, Liposyn®, Liposyn® II, Liposyn® III, Nutrilipid, and other similar lipid emulsions. A preferred colloidal system for use as a delivery vehicle in vivo is a liposome (i.e., an artificial membrane vesicle). The preparation and use of such systems is well known in the art. Exemplary formulations are also disclosed in U.S. Pat. Nos. 5,981,505; 6,217,900; 6,383,512; 5,783,565; 7,202,227; 6,379,965; 6,127,170; 5,837,533; 6,747,014; and WO 2003/093449, which are hereby incorporated by reference in their entireties.

The pharmaceutical compositions and formulations may employ appropriate salts and buffers to render delivery vehicles stable and allow for uptake by target cells. Aqueous compositions of the present invention comprise an effective amount of the delivery vehicle comprising the presently claimed oligonucleotide (e.g. liposomes or other complexes), dissolved or dispersed in a pharmaceutically acceptable carrier or aqueous medium. The phrases "pharmaceutically acceptable" or "pharmacologically acceptable" refers to molecular entities and compositions that do not produce adverse, allergic, or other untoward reactions when administered to an animal or a human. As used herein, "pharmaceutically acceptable carrier" may include one or more solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Supplementary active ingredients also can be incorporated into the compositions.

Administration or delivery of the pharmaceutical compositions according to the present invention may be via any route so long as the target tissue is available via that route. For example, administration may be by intradermal, subcutaneous, intramuscular, intraperitoneal or intravenous injection, or by direct injection into target tissue (e.g., cardiac tissue). The stability and/or potency of the oligonucleotides disclosed herein allows for convenient routes of administration, including subcutaneous, intradermal, and intramuscular. Pharmaceutical compositions comprising miRNA inhibitors may also be administered by catheter systems or systems that isolate coronary circulation for delivering therapeutic agents to the heart. Various catheter systems for delivering therapeutic agents to the heart and coronary vasculature are known in the art. Some non-limiting examples of catheter-based delivery methods or coronary isolation methods suitable for use in the present invention are disclosed in U.S. Pat. Nos. 6,416,510; 6,716,196; 6,953,466, WO 2005/082440, WO 2006/089340, U.S. Patent Publication No. 2007/0203445. U.S. Patent Publication No. 2006/0148742, and U.S. Patent Publication No. 2007/0060907, which are all hereby incorporated by reference in their entireties.

The compositions or formulations may also be administered parenterally or intraperitoneally. By way of illustration, solutions of the conjugates as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use or catheter delivery include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the conjugates in an appropriate amount into a solvent along with any other ingredients (for example as enumerated above) as desired. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion. (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by the FDA Office of Biologics standards.

In another aspect, the present invention provides a method of reducing or inhibiting RNA expression or activity in a cell. In such embodiments, the method comprises contacting the cell with an oligonucleotide disclosed herein (or pharmaceutical composition thereof), where the oligonucleotide hybridizes (e.g., is at least substantially complementary) to an RNA transcript expressed by the cell. In some embodiments, the RNA is an mRNA or a miRNA.

In another aspect, the present invention provides a method of preventing or treating a condition in a subject associated with or mediated by RNA or expression thereof. In some embodiments, the RNA is a mRNA or a miRNA. The method of prevention or treatment according to the present invention involves administering to the subject a pharmaceutical composition which comprises an effective amount of the oligonucleotide or its pharmaceutically-acceptable composition thereof.

The invention provides a method for delivering the oligonucleotides of the present invention to a mammalian cell (e.g., as part of a composition or formulation described herein), and methods for treating, ameliorating, or preventing the progression of a condition in a mammalian patient. The oligonucleotide or pharmaceutical composition may be contacted in vitro or in vivo with a target cell (e.g., a mammalian cell). The cell may be a heart cell.

The method generally comprises administering the oligonucleotide or composition comprising the same to a mammalian patient or population of target cells. The oligonucleotide, as already described, may be a miRNA inhibitor (e.g., having a nucleotide sequence designed to inhibit expression or activity of a miRNA). For example, where the miRNA inhibiter is an inhibitor of a miR-208 family miRNA, the patient may have a condition associated with, mediated by, or resulting from, miR-208 family expression. Such conditions include, for example, cardiac hypertrophy, myocardial infarction, heart failure (e.g., congestive heart failure), vascular damage, restenosis, or pathologic cardiac fibrosis, cancer, or other miRNA associated disorder, including those disorders described in the patent publication listed in Table 2. Thus, the invention provides a use of the modified oligonucleotides and compositions of the invention for treating such conditions, and for the preparation of medicaments for such treatments.

In certain embodiments, the patient (e.g., human patient) has one or more risk factors including, for example, long standing uncontrolled hypertension, uncorrected valvular disease, chronic angina, recent myocardial infarction, congestive heart failure, congenital predisposition to heart disease and pathological hypertrophy. Alternatively or in addition, the patient may have been diagnosed as having a genetic predisposition to, for example, cardiac hypertrophy, or may have a familial history of, for example, cardiac hypertrophy.

In this aspect, the present invention may provide for an improved exercise tolerance, reduced hospitalization, better quality of life, decreased morbidity, and/or decreased mortality in a patient with heart failure or cardiac hypertrophy.

In certain embodiments, the activity of microRNA in cardiac tissue, or as determined in patient serum, is reduced or inhibited.

In various embodiments, the pharmaceutical composition is administered by parenteral administration or by direct injection into heart tissue. The parenteral administration may be intravenous, subcutaneous, or intramuscular. In some embodiments, the composition is administered by oral, transdermal, sustained release, controlled release, delayed release, suppository, catheter, or sublingual administration. In certain embodiments, the oligonucleotide is administered at a dose of about 50 mg/kg or less, a dose of about 25 mg/kg or less, a dose of about 10 mg/kg or less, or a dose of about 5 mg/kg or less. In these embodiments, the oligonucleotide or composition may be administered by intramuscular or subcutaneous injection, or intravenously.

In some embodiments, the methods further comprise scavenging or clearing the miRNA inhibitors following treatment. For example, an oligonucleotide having a nucleotide sequence that is complementary to the inhibitor may be administered after therapy to attenuate or stop the function of the inhibitor.

All references cited herein, including those in Tables 1 and 2, are hereby incorporated by reference for all purposes.

EXAMPLES

Example 1

Production of 2'-C-Bridged Bicyclic Nucleotides

This example describes an exemplary synthesis of key intermediates for the production of amine 2'-C-Bridged Bicyclic Nucleotides (see FIG. 1).

Methyl-D-Ribose (2)

In three 500 mL Schott Bottles were D-ribose (1) (90 g, 599 mmol), Amberlyst 15 (H+) (90 g, 599 mmol), and Molecular Trap Pack (90 g, 599 mmol) divided equally (i.e. 30 g each in each Schott bottle). Each bottle was filled with an equal amount of methanol (Volume: 1350 ml, i.e. 450 mL/bottle) to give a colorless solution. All bottles were placed on an orbital shaker @250 rpm/25° C. for 17 hours. Reaction progress was monitored by TLC of the reaction mixture compared to co-spot with unprotected ribose in 15% MeOH/DCM as developing solvent. The sugars were visualized via Hannessian's Stain with charring.

The solutions were filtered through a glass sintered funnel. The catalyst and Molecular Trap Packs were washed with excess MeOH (~500 mL/Bottle that contained 30 g each of Amberlyst and Trap Packs). The methanol solution was made basic by addition of 15 mL of TEA (5 mL/reaction bottle). The mixtures were concentrated to dryness. The residue was co-evaporated with dichloromethane (3×200 mL) to azeotrope off residual MeOH. The residue was dried under high vacuum overnight to give 97.55 g (99%) of methyl-D-ribose (2) which was used without further purification.

Methyl 5-O-(TBDPS)-α,β-D-ribofuranoside(3)

In a 1 L round-bottomed flask was methyl-D-ribose (2, 60.12 g, 366 mmol) and DIEA (128 ml, 732 mmol) dissolved in DMF (Volume: 400 ml) to give a colorless solution. The flask was flushed with argon and cooled to 0° C. in an ice bath. TBDPS-Cl (99 ml, 385 mmol) was added dropwise over 10 minutes and the mixture was allowed to come to room temperature overnight.

The reaction mixture was poured into a solution of saturated NaHCO$_3$ (1 L). The aqueous phase was extracted with EtOAc (3×300 mL). The organic phases were combined and washed with water (1×400 mL) and brine (1×400 mL). The organic phase was dried over Na$_2$SO$_4$, filtered and concentrated to give a dark brown oil that was purified by dividing into 4 equal portions and purifying via silica chromatography running a standard 0-100% EtOAc/Hex gradient over 75 minutes at 100 mL/min followed by a 7 minute hold @100% EtOAc. Pure fractions were combined to give 121.59 g (82%) of methyl 5-O-(TBDPS)-α,β-D-ribofuranoside (3) as a colorless oil.

Methyl 5-O-(TBDPS)-2,3-O-bis(4-Chlorobenzyl)-α, β-D-ribofuranoside (4)

In a 2 L round-bottomed flask was weighed Methyl 5-O-(TBDPS)-α,β-D-ribofuranoside (3, 55.0 g, 137 mmol). The material was co-evaporated with toluene (2×100 mL) at 40° C. and high vacuum. The flask was fitted with a reflux condenser and the starting material was dissolved under argon in Toluene (Volume: 500 ml). Sodium hydride (21.86 g, 547 mmol) was added in ~5 g portions to give a gray suspension. The mixture was heated to 60° C. for 30 minutes and then cooled to room temperature with an ice bath, 1-chloro-4-(chloromethyl)benzene (66.0 g, 410 mmol) was added in ~15 g portions with vigorous stirring. The mixture was heated and stirred overnight at reflux.

The reaction mixture was cooled to 0° C. and diluted with 500 mL of EtOAc. The mixture was quenched by slow addition of EtOH (50 mL) to minimize bubbling. The mixture was further diluted to 1.5 L with EtOAc and Washed with 10% $Na_2CO_3$ (2×500 mL) and sat NaCl (1×500 mL). The organic was dried over $Na_2SO_4$, filtered and concentrated. The crude product was purified via silica gel chromatography. Product was eluted with a 0-30% EtOAc/Hexanes gradient. Pure collected fractions were combined to give methyl 5-O-(TBDPS)-2,3-O-bis(4-chlorobenzyl)-α,β-D-ribofuranoside (4, 62.15 g, 70%) as an amber oil.

Methyl 5-O-(TBDPS)-3-O-(4-Chlorobenzyl)-α-D-ribofuranoside (5)

In a 1 L round-bottomed flask was methyl 5-O-(TBDPS)-2,3-O-bis(4-chlorobenzyl)-α,β-D-ribofuranoside (4, 65 g, 100 mmol) dissolved in 600 mL DCM to give a yellow solution. The mixture was cooled to 0° C. under argon. Tin (IV) Chloride (150 ml, 150 mmol) was added slowly over 10 minutes while solution turns to a clear, dark brown solution. The reaction mixture was stored overnight at 4° C., under argon with stirring.

The reaction mixture was diluted with DCM (250 mL) and added to 500 mL of DI water in a 4 L sep funnel. The mixture was shaken vigorously and allowed to separate. All organic and emulsion/precipitate was retained and washed with a second aliquot of 500 mL water. All organic and emulsion/precipitate was retained and washed with 500 mL of 10% $Na_2CO_3$ in water. The emulsion was reduced via addition of MeOH and mechanical agitation. All organic and emulsion/precipitate was retained and finally washed with 500 mL brine. Again, the emulsion was reduced via addition of MeOH and mechanical agitation. The organic phase was removed and dried via $MgSO_4$ suspension. The remaining emulsion and aqueous phase was extracted with additional DCM (2×100 mL) which was combined with the $MgSO_4$ suspension. The organic phase was filtered and concentrated to a brown oil. The crude product was purified via silica gel column chromatography with a 0-30% EtOAc/Hexanes gradient. Pure collected fractions were combined to give methyl 5-O-(TBDPS)-3-O-(4-chlorobenzyl)-α-D-ribofuranoside (5, 41.20 g, 78%) as an amber oil.

Methyl 5-O-(TBDPS)-3-O-(4-Chlorobenzyl)-2-oxo-α-D-ribofuranoside (6)

In a 1 L round-bottomed flask was dissolved methyl 5-O-(TBDPS)-3-O-(4-chlorobenzyl)-α-D-ribofuranoside (5, 41.00 g, 78 mmol) and TEMPO (1.215 g, 7.78 mmol) in DCM (Volume: 250 ml) to give an orange solution. Iodobenzene diacetate (37.6 g, 117 mmol) was added and the mixture was allowed to stir overnight at room temperature.

Reaction mixture was diluted to 500 mL with DCM and washed with saturated sodium thiosulfate solution (2×300 mL), and brine (1×300 mL). The organic phase was dried over $MgSO_4$, filtered and concentrated. The orange residue was dried under high vacuum at 50° C. for 3 hours. The crude methyl 5-O-(TBDPS)-3-O-(4-chlorobenzyl)-2-oxo-α-D-ribofuranoside (6, 40.50, "99%") as an amber oil was used as is for subsequent reaction.

Methyl 5-O-(TBDPS)-3-O-(4-Chlorobenzyl)-2-deoxy-2-methylene-α-D-ribofuranoside (7)

In a 2000 mL round-bottomed flask was methyltriphenylphosphonium bromide (6, 26.6 g, 75 mmol) was suspended in ether (Ratio: 20.00, Volume: 1500 ml) to give a white suspension. The flask was flushed with argon and cooled to 0° C. in an ice bath. Sodium t-pentoxide (7.39 g, 67 mmol) was dissolved in Benzene (Ratio: 1.000, Volume: 75 ml) and added at once to the suspension. The flask was again flushed with argon and allowed to come to room temperature over 2 hours. The suspension was allowed to stir for an additional 4 hours. The suspension was then cooled to −72° C. in an Acetone/dry ice bath, methyl 5-O-(TBDPS)-3-O-(4-chlorobenzyl)-2-oxo-α-D-ribofuranoside (19.56 g, 37.25 mmol) was dissolved in additional Ether (Ratio: 1.067, Volume: 40 ml). The carbohydrate solution was added via syringe and the reaction mixture was allowed to stir at 4° C. for 17 hours.

TLC revealed that the reaction was complete (15% EtOAc/Hex). The reaction mixture was washed with sat $NH_4Cl$ (2×500 mL) and brine (1×250 mL). The aqueous phase was back-extracted with Ether (150 mL). The organic phases were combined and dried with a brine wash (1×250 mL) and addition of $Na_2SO_4$. The organic phase was filtered and concentrated. Purification was done via silica gel column chromatography using a 0-20% EtOAc in Hexanes gradient. Pure fractions were combined and concentrated to dryness to give methyl 5-O-(TBDPS)-3-O-(4-chlorobenzyl)-2-deoxy-2-methylene-α-D-ribofuranoside (7, 14.79 g, 28.3 mmol, 76% yield) as a colorless oil.

Methyl 5-O-(TBDPS)-3-O-(4-Chlorobenzyl)-2-deoxy-2-α-Hydroxymethyl-α-D-Ribofuranoside (8)

Under argon, 9-BBN (8.97 g, 73.5 mmol) was added to a solution of methyl 5-O-(TBDPS)-3-O-(4-chlorobenzyl)-2-deoxy-2-methylene-α-D-ribofuranoside (7, 28.50 g, 54.5 mmol) in THF (300 ml) at room temperature. After the reaction mixture was stirred at room temperature for 1.5 hours, TLC revealed that all starting material was consumed.

Sodium perborate tetrahydrate (33.9 g, 221 mmol) and water (80 mL) were added and the mixture was stirred at room temperature for an additional 2 hours. The organic layer was separated, and the aqueous was diluted to 400 mL then extracted with ethyl acetate (3×250 mL). The organic layers were combined and dried over $MgSO_4$. The solvent was removed, and the product was purified by silica gel chromatography eluting with ethyl acetate/hexanes gradient of 0-60%. The purified fractions were combined and concentrated to dryness to give methyl 5-O-(TBDPS)-3-O-(4-chlorobenzyl)-2-deoxy-2-α-hydroxymethyl-α-D-ribofuranoside (8, 26.39 g, 48.8 mmol, 90% yield) as a colorless oil.

Methyl 3-O-(4-Chlorobenzyl-2-deoxy-2-α-(4,4'-Dimethoxytrityloxymethyl)-α-D-Ribofuranoside (10)

In a 1 L round-bottomed flask was methyl 5-O-(TBDPS)-3-O-(4-chlorobenzyl)-2-deoxy-2-α-hydroxymethyl-α-D-ribofuranoside (8, 26.30 g, 48.6 mmol) in pyridine (200 ml) dissolved under Argon to give a colorless solution. DMTr-Cl (20.58 g, 60.8 mmol) was added, at once, to the stirring solution. The reaction mixture was allowed to stir overnight. The trytilation reaction was quenched by the addition of 50 mL of MeOH with stirring for 20 minutes followed by diluting the mixture to 750 mL with EtOAc. The Organic phase was washed with saturated NaHCO$_3$ solution (3×350 mL) and Brine (1×150 mL). The organic phase was dried over Na$_2$SO$_4$, filtered and concentrated to dryness.

The crude product (9) was dissolved in THF (Volume: 70 ml), 1.0 M TBAF in THF solution (72.9 ml, 72.9 mmol) was added to the mixture and it was allowed to stir at room temperature for 1.5 hours. Addition of the TBAF resulted in a dark, smoky colored solution. The mixture was concentrated to dryness and applied to a 330 g ISCO silica column pretreated with 3% TEA in hexanes. The product was eluted with a 0-60% EtOAc in Hexanes gradient over 50 minutes @100 mL/min. The pure fractions were combined and concentrated to give methyl 3-O-(4-chlorobenzyl)-2-deoxy-2-α-(4,4'-dimethoxytrityloxymethyl)-α-D-ribofuranoside (10, 27.17 g, 44.9 mmol, 92% yield) as a colorless oil.

Methyl 5-Oxo-3-O-(4-Chlorobenzyl)-2-deoxy-2-α-(4,4'-Dimethoxytrityloxymethyl)-α-D-Ribofuranoside (11)

In a 1 L round-bottomed flask was methyl 3-O-(4-chlorobenzyl)-2-deoxy-2-α-(4,4'-dimethoxytrityloxymethyl)-α-D-ribofuranoside (10, 27.15 g, 44.9 mmol) and DCC (27.8 g, 135 mmol) dissolved in DMSO (166 ml, 2333 mmol) to give a colorless solution. Pyridine (5.44 ml, 67.3 mmol) and TFA (1.728 ml, 22.43 mmol) were combined in 40 mL of DMSO and the resulting solution was added to the reaction mixture. The flask was covered and allowed to stir overnight at room temperature.

Water (25 mL) was added and the reaction was allowed to stir at room temperature for 3 hours. The reaction was diluted with 500 mL EtOAc and filtered. The precipitate was washed with an additional 200 mL of EtOAc. The combined organic was washed with Brine (5×400 mL), dried with Na$_2$SO$_4$, filtered and concentrated. The product was purified via silica gel column chromatography with a 0-100% EtOAc/Hex gradient. Pure fractions were combined and concentrated to give methyl 5-oxo-3-O-(4-chlorobenzyl)-2-deoxy-2-α-(4,4'-dimethoxytrityloxymethyl)-α-D-ribofuranoside (11, 25.22 g, 41.8 mmol, 93% yield) as a white foam.

Methyl 4-C-Hydroxymethyl-3-O-(4-Chlorobenzyl)-2-deoxy-2-α-(4,4'-Dimethoxytrityloxymethyl)-α-D-Ribofuranoside (12)

In a 2 L round-bottomed flask was methyl 5-oxo-3-O-(4-chlorobenzyl)-2-deoxy-2-α-(4,4'-dimethoxytrityloxymethyl)-α-D-ribofuranoside (11, 25.20 g, 41.8 mmol) dissolved in Dioxane (1000 ml) to give a colorless solution. Formaldehyde (249 ml, 3343 mmol) was added with stirring. The reaction mixture was cooled to 0° C. in an ice bath. The flask was fitted with a 750 mL pressure equalizing dropping funnel and 2.0 M sodium hydroxide (606 ml, 1212 mmol) was added over 30 minutes to give a cloudy white solution. The mixture was allowed to stir while coming to room temperature over 42 hours. The solution had turned clear. The solution was neutralized by addition of sodium phosphate, monobasic, monohydrate (86 g, 627 mmol). The solution was concentrated to about a third of its volume, diluted with 500 mL of water and extracted with DCM (3×300 mL). The organic layers were combined and washed with brine (1×300 mL) then dried over Na$_2$SO$_4$. The solvent was removed, and the product was purified by silica gel chromatography eluting with a MeOH/DCM gradient of 0-10%. The purified fractions were combined and concentrated to dryness to give methyl 4-C-hydroxymethyl-3-O-(4-chlorobenzyl)-2-deoxy-2-α-(4,4'-dimethoxytrityloxymethyl)-α-D-ribofuranoside (12, 22.50 g, 35.4 mmol, 85% yield) as a colorless oil.

Methyl 5-O-Mesyl-4-C-(Mesyloxymethyl-3-O-(4-Chlorobenzyl)-2-deoxy-2-α-(Hydroxymethyl)-α-D-Ribofuranoside (14)

In a 1 L round-bottomed flask was methyl 4-hydroxymethyl-3-O-(4-chlorobenzyl)-2-deoxy-2-α-(4,4'-dimethoxytrityloxymethyl)-α-D-ribofuranoside (12, 22.50 g, 35.4 mmol) dissolved in Pyridine (200 ml) under Ar to give a colorless solution. The mixture was cooled to 0° C. in an ice bath. Mesyl-Cl (8.28 ml, 106 mmol) was added, dropwise over 10 minutes, to the stirring solution. The reaction mixture was stirred for 45 minutes at room temperature. The mesylation reaction was quenched by cooling the reaction to 0° C. and adding 15 mL of Water with stirring for 20 minutes. The mixture was diluted to 750 mL with EtOAc and washed with brine (3×400 mL). The organic phase was dried over Na$_2$SO$_4$, filtered and concentrated to dryness.

The crude product (13) was dissolved in 800 mL of AcOH. Water (200 mL) was added to the stirring solution. The solution was allowed to stir at room temperature for 2.5 hours then diluted with 500 mL of water. The mixture was concentrated to about 400 mL and diluted with an additional 250 mL of water. The solution was then concentrated to dryness under high vacuum. The residue was applied to a 220 g ISCO silica column and the product was eluted with a 0-100% EtOAc/Hexanes gradient. The pure fractions were combined and concentrated to give methyl 5-O-mesyl-4-C-(mesyloxymethyl)-3-O-(4-chlorobenzyl)-2-deoxy-2-α-(Hydroxymethyl)-α-D-ribofuranoside (14, 10.01 g, 20.47 mmol, 57.8% yield) as a colorless oil.

((2S,3R,4S)-2-acetoxy-4-((4-chlorobenzyl)oxy)-5,5-bis(((methylsulfonyl)oxy)methyl)tetrahydrofuran-3-yl)methyl acetate (16)

((3S,4R,5S)-3-((4-chlorobenzyl)oxy)-4-(hydroxymethyl)-5-methoxytetrahydrofuran-2,2-diyl)bis(methylene) dimethanesulfonate (3.41 g, 6.97 mmol) was weighed into a 100 ml round-bottomed flask with a stir bar and septum sealed. The flask was cooled to 0° C. and charged with pyridine (Volume: 25 ml) and acetic anhydride (1.316 ml, 13.95 mmol). The mixture was allowed to come to room temperature over 6 hours. The mixture was cooled to 0° C. and MeOH (1 mL) was added and allowed to stir for 15 minutes. The mixture was concentrated to dryness and re-dissolved in EtOAc (100 mL). The organic phase was washed with aqueous 1% HCl (50 mL), saturated sodium bicarbonate (50 mL) and brine (50 mL). The organic phase was dried over Na$_2$SO$_4$, filtered and concentrated.

The resultant oil was re-dissolved with acetic acid (9.98 ml, 174 mmol) and acetic anhydride (2.63 ml, 27.9 mmol) in a 100 mL round-bottomed flask. H$_2$SO$_4$ (0.037 ml, 0.697 mmol) was added, the flask septum sealed and the mixture was allowed to stir overnight. The mixture was diluted with water (100 mL) and extracted with EtOAc (3×75 mL). The organic phases were combined and washed carefully with saturated sodium bicarbonate (2×100 mL) and brine (1×100 mL). The organic phase was dried over Na$_2$SO$_4$, filtered and concentrated to give 3.15 g of crude ((2S,3R,4S)-2-acetoxy-4-((4-chlorobenzyl)oxy)-5,5-bis(((methylsulfonyl)oxy)methyl)tetrahydrofuran-3-yl)methyl acetate (3.15 g, 5.64 mmol, 81% yield) as a pale yellow oil that was used without further purification.

ESI-MS: 617 (M+Acetate)$^-$ ((3R,4S)-4-((4-chlorobenzyl)oxy-2-(thymidin-yl)-5,5-bis(((methylsulfonyl)oxy)methyl)tetrahydrofuran-3-yl)methyl acetate (17)

N,O-Bis(trimethylsilyl)acetamide (4.07 ml, 16.64 mmol) was added to a mixture of ((3R,4S)-2-acetoxy-4-((4-chlorobenzyl)oxy)-5,5-bis(((methylsulfonyl)oxy)methyl)tetrahydrofuran-3-yl)methyl acetate (3.10 g, 5.55 mmol) and thymine (0.874 g, 6.93 mmol) in anhydrous acetonitrile (20 ml). The reaction mixture was refluxed for 1 hour to get a clear solution. The solution was cooled to 40° C. and TMS-OTf (1.303 ml, 7.21 mmol) was added. The mixture was heated at 60° C. for 4 hours. The solution was cooled to room temperature, diluted with CH$_2$Cl$_2$ (100 mL), and washed with saturated NaHCO$_3$ (2×100 mL) and brine (1×100 mL). The organic layer was dried (Na$_2$SO$_4$), concentrated under reduced pressure, and the residue was purified by silica gel column chromatography on a standard Biotage Isolera gradient (0-10% v/v MeOH/CH$_2$Cl$_2$) to give ((3R,4S)-4-((4-chlorobenzyl)oxy)-2-(thymidin-yl)-5,5-bis(((methylsulfonyl)oxy)methyl)tetrahydrofuran-3-yl)methyl acetate (2.84 g, 4.54 mmol, 82% yield) as a white solid material.

ESI-MS: 624 (M)$^-$ ((3S,4R)-3-((4-chlorobenzyl)oxy)-4-(hydroxymethyl)-5-(thymidin-yl)tetrahydrofuran-2,2-diyl)bis(methylene)dimethanesulfonate (19)

In a 100 mL round-bottomed flask fitted with a stir bar, ((3R,4S)-4-((4-chlorobenzyl)oxy)-2-(thymidin-yl)-5,5-bis(((methylsulfonyl)oxy)methyl)tetrahydrofuran-3-yl)methyl acetate (2.84 g, 4.54 mmol) was dissolved in Methanol (Volume: 20 ml). Sodium methoxide (0.123 g, 2.272 mmol) was added and the flask was covered and allowed to stir overnight at room temperature. TLC (100% EtOAc) revealed that the reaction was complete. The reaction mixture was evaporated to dryness in vacuo, and applied directly to a 3 g Biotage Samplet, which was fitted to a 25 g Biotage SNAP column. The product was eluted with a 40-100% EtOAc/Hex gradient to give ((3S,4R)-3-((4-chlorobenzyl)oxy)-4-(hydroxymethyl)-5-(thymidin-yl)tetrahydrofuran-2,2-diyl)bis(methylene)dimethanesulfonate (2.32 g, 3.98 mmol, 88% yield) as a white foam.

ESI-MS: 582 (M)$^-$ ((3S,4R)-5-(thymidin-yl)-3-((4-chlorobenzyl)oxy)-4-(hydroxymethyl)tetrahydrofuran-2,2-diyl)bis(methylene)dimethanesulfonate (20)

To a mixture of ((3S,4R)-3-((4-chlorobenzyl)oxy)-4-(hydroxymethyl)-5-(thymidin-yl)tetrahydrofuran-2,2-diyl)bis(methylene)dimethanesulfonate (1.0 g, 1.715 mmol) and pyridine (10 ml) was added TMS-Cl (0.219 ml, 1.715 mmol) at room temperature. After stirring for 1 hour, the reaction mixture was cooled to 0° C., and benzoyl chloride (0.199 ml, 1.715 mmol) was added dropwise by syringe. The ice-bath was then removed and the reaction mixture stirred at room temperature for 48 hours. The reaction was quenched by the addition of water (2 mL); after stirring for 15 minutes at room temperature, the mixture was diluted with EtOAc (50 mL) and washed with aqueous 5% HCl (2×25 mL), saturated NaHCO$_3$ (1×25 mL) and brine (1×25 mL). The organic phase was dried over Na$_2$SO$_4$, filtered and concentrated to dryness in vacuo. The residue was applied to a 3 g Biotage Samplet with minimal DCM, which was then fitted to a 25 g Biotage SNAP column. The desired product was eluted with 40-100% EtOAc/Hex gradient to give ((3S,4R)-5-(3-benzoyl-5-methyl-2,4-dioxo-3,4-dihydropyrimidin-1(2H)-yl)-3-((4-chlorobenzyl)oxy)-4-(hydroxymethyl)tetrahydrofuran-2,2-diyl)bis(methylene)dimethanesulfonate (0.87 g, 1.266 mmol, 73.8% yield) as a white foam.

N-Benzoyl protection of thymidine results in a diastereomeric mixture which gives rise to two C-5 methyl singlets and two C-6 proton singlets in a 3:2 ratio. For the α-anomer:

$^1$H NMR (400 MHz, Chloroform-d) δ 7.89 (s, 1H, diastereomer 1), 7.87 (d, J=1.3 Hz, 1H, diastereomer 2), 7.67-7.60 (m, 1H), 7.60-7.39 (m, 3H), 7.39-7.17 (m, 5H), 6.02 (d, J=8.6 Hz, 1H), 4.67-4.46 (m, 3H), 4.42-4.26 (m, 5H), 3.87-3.73 (m, 2H), 3.02 (s, 3H), 2.98 (s, 2H), 2.82 (p, J=6.5 Hz, 1H), 2.03 (s, 3H, diastereomer 1), 1.94 (s, 3H, diastereomer 2).

((3S,4R,5R)-4-(((tert-butoxy-(2,2,2-trifluoroethoxy)dicarbonyl)amino)methyl)-3-((4-chlorobenzyl)oxy)-5-(3-benzoyl-thymidin-yl)tetrahydrofuran-2,2-diyl)bis(methylene)dimethanesulfonate (21)

In a 20 mL scintillation vial fitted with a stir bar was weighed ((3S,4R)-5-(3-benzoyl-thymidin-yl)-3-((4-chlorobenzyl)ox y)-4-(hydroxymethyl)tetrahydrofuran-2,2-diyl)bis(methylene)dimethanesulfonate (0.25 g, 0.364 mmol), (2,2,2-trifluoroethyl)-tert-Butyl-iminodicarbonate (0.088 g, 0.364 mmol), and triphenylphosphine (0.095 g, 0.364 mmol). The vial was charged with THF (Volume: 4 ml) and DIAD, 1.0M Solution in THF (0.364 ml, 0.364 mmol) was added dropwise. After stirring overnight, the reaction mixture was concentrated to dryness in vacuo and applied to a 25 g Biotage SNAP column. Product was eluted with 40-100% EtOAc/Hexanes gradient to give ((3S,4R,5R)-4-(((tert-butoxy-(2,2,2-trifluoroethoxy)dicarbonyl)amino)methyl)-3-((4-chlorobenzyl)oxy)-5-(3-benzoyl-thymidin-yl)tetrahydrofuran-2,2-diyl)bis(methylene)dimethanesulfonate (0.228 g, 0.25 mmol, 68.7% yield) as a white foam.

1H NMR (400 MHz, Chloroform-1) δ 7.94 (d, J=7.6 Hz, 2H), 7.63 (t, J=7.4 Hz, 1H), 7.47 (t, J=7.8 Hz, 2H), 7.34 (d, J=8.4 Hz, 2H), 7.28 (d, J=8.4 Hz, 2H), 7.15 (s, 1H), 5.99 (d, J=9.2 Hz, 1H), 4.70 (d, J=11.0 Hz, 1H), 4.60 (d. J=10.9 Hz, 1H), 4.49 (qd, J=8.3, 3.4 Hz, 2H), 4.41-4.24 (m, 6H), 3.94 (d, J=5.6 Hz, 2H), 3.20-3.05 (m, 1H), 2.98 (s, 2H), 2.97 (s, 4H), 1.92 (s, 3H), 1.46 (s, 9H). ESI-MS: 971 (M+Acetate)$^-$ ((3S,4R,5R)-4-(((tert-butoxycarbonyl)amino)methyl)-3-((4-chlorobenzyl)oxy)-5-(thymidin-yl)tetrahydrofuran-2,2-diyl)bis(methylene)dimethanesulfonate (22)

In a 20 mL screw cap scintillation vial was ((3S,4R,5R)-4-(((tert-butoxy-(2,2,2-trifluoroethoxy)dicarbonyl)amino)methyl)-3-((4-chlorobenzyl)oxy)-5-(3-benzoyl-thymidin-yl)tetrahydrofuran-2,2-diyl)bis(methylene)dimethanesulfonate (125 mg, 0.137 mmol) weighed with a magnetic stir bar. The vial was charged with THF (Volume: 1.5 ml) and 2.0M LiOH in water (1.507 ml, 3.01 mmol), covered and allowed to stir overnight at room temperature The reaction mixture was diluted with EtOAc (7 mL) and washed with saturated sodium bicarbonate (1×5 mL) and brine (1×5 mL). The organic phase was dried over Na2SO4, Filtered and concentrated in vacuo to give ((3S,4R,5R)-4-(((tert-butoxycarbonyl)amino)methyl)-3-((4-chlorobenzyl)oxy)-5-(thymidin-yl)tetrahydrofuran-2,2-diyl)bis(methylene)dimethanesulfonate (80 mg, 0.117 mmol, 86% yield) as an off white foam that was sufficiently pure to be used crude for subsequent reactions.

1H NMR (400 MHz, Chloroform-d) δ 8.61 (s, 1H), 7.36 (d, J=8.4 Hz, 2H), 7.27 (d. J=8.4 Hz, 2H), 7.13 (s, 1H), 6.04 (d, J=9.3 Hz, 1H), 4.74-4.64 (m, 1H), 4.59 (d, J=11.3 Hz, 1H), 4.50 (d, J=11.3 Hz, 1H), 4.40-4.23 (m, 6H), 4.00-3.89 (m, 1H), 3.44 (dd, J=13.6, 6.7 Hz, 1H), 3.17 (ddd, J=14.3, 8.4, 5.8 Hz, 1H), 3.09 (s, 3H), 3.00 (s, 3H), 1.89 (s, 3H), 1.32 (s, 9H). ESI-MS: 681 (M)$^-$ (1R,5R,7R,8S)-tert-butyl 8-((4-chlorobenzyl)oxy)-7-(thymidin-yl)-5-(((methylsulfonyl)oxy)methyl)-6-oxa-3-azabicyclo[3.2.1]octane-3-carboxylate (23)

In a 10 mL conical reaction vial was ((3S,4R,5R)-4-(((tert-butoxycarbonyl)amino)methyl)-3-((4-chlorobenzyl)oxy)-5-(thymidin-yl)tetrahydrofuran-2,2-diyl)bis(methylene)dimethanesulfonate (60 mg, 0.076 mmol) dissolved in Tetrahydrofuran (7 ml). Sodium hydride, 60% Suspension in oil (12.21 mg, 0.305 mmol) was added to the vial at once, the vial was fitted with a stir bar and a teflon-lined septum screw-cap and the mixture was stirred at 55° C. overnight. The reaction was cooled to room temperature and quenched with a few drops of MeOH added with stirring. The mixture was diluted with EtOAc (10 mL) and washed with aqueous saturated sodium bicarbonate (2×10 mL) and brine (1×10 mL). The organic phase was dried over Na2SO4, filtered and concentrated to give a tan foam that was dissolved in a minimal amount of DCM and applied to a 1 g Biotage Samplet fitted to a 10 g Biotage SNAP column. Product was eluted with a 0-100% EtOAc/Hexanes gradient to give (1R,5R,7R,8S)-tert-butyl 8-((4-chlorobenzyl)oxy)-7-(thymidin-yl)-5-(((methylsulfonyl)oxy)methyl)-6-oxa-3-azabicyclo[3.2.1]octane-3-carboxylate (35 mg, 0.060 mmol, 78% yield) as a white foam.

The cyclization gives a mixture of N-diastereomers in a 3:2 mixture that was unresolvable by TLC/column chromatography. This presence of the minor diastereomer gave rise to several distinct signals that are denoted by a (*). 1H NMR (400 MHz, Chloroform-d) δ 8.63 (s, 1H), 8.59* (s), 7.62 (s, 1H), 7.58* (s), 7.40-7.27 (m, 2H), 7.23 (d, J=8.1 Hz, 3H), 5.80* (s), 5.79 (s, 1H), 4.66-4.44 (m, 2H), 4.44-4.27 (m, 2H), 4.09-3.92 (m, 2H), 3.79 (d, J=12.8 Hz, 1H), 3.61* (d, J=12.6 Hz), 3.36-3.10 (m, 2H), 3.08 (s, 3H), 2.81* (s), 2.70 (s, 1H), 1.94 (s, 3H), 1.46 (s, 9H), 1.44* (s). ESI-MS: 585 (M)$^-$ 1-((1R,5R,7R,8S)-8-((4-chlorobenzyl)oxy)-5-(hydroxymethyl)-6-oxa-3-azabicyclo[3.2.1]octan-7-yl)-thymidine (24)

In a 10 mL glass reaction vial was (1R,5R,7R,8S)-tert-butyl 8-((4-chlorobenzyl)oxy)-7-(thymidin-yl)-5-(((methylsulfonyl)oxy)methyl)-6-oxa-3-azabicyclo[3.2.1]octane-3-carboxylate (35 mg, 0.060 mmol) and sodium benzoate (17.21 mg, 0.119 mmol) dissolved in DMF (2 ml). The vial was fitted with a stir bar and sealed with a teflon lined screw-cap septum. The mixture was heated to 105° C. in an oil bath overnight. All components had effected solution. The vial was removed from the oil bath and 10 uL removed to asses reaction completeness via TLC. White crystals started forming immediately upon cooling. TLC revealed reaction was only 50% complete, so an additional portion of sodium benzoate (17.21 mg, 0.119 mmol) was added along with 1 mL DMF to allow for stirring. The mixture was heated to 105° C. for an additional 48 hours with periodic aliquots removed for TLC analysis. The thick precipitate never fully effected solution, even after heating to 105° C. for two days, however the reaction went to completion with no detectable decomposition.

The reaction mixture was cooled to room temperature, diluted with EtOAc (10 mL) and washed with water (2×10 mL), saturated bicarbonate solution (1×10 mL) and brine (1×10 mL). The organic phase was dried over Na$_2$SO$_4$, filtered and concentrated in vacuo. The residue was re-dissolved in MeOH (2 ml) and sodium methoxide (6.45 mg, 0.119 mmol) was added at once. The mixture was allowed to stir overnight. TLC revealed that the reaction was complete and the mixture was concentrated to dryness. The resultant residue was re-dissolved in 1 mL of 1:1 DCM/TFA and stirred for 30 minutes at room temperature. The mixture was concentrated to dryness and applied to a 4 g RediSep Rf silica column using a minimal amount of DCM. The product was eluted with a 0-100% EtOAc/Hex gradient containing 3% TEA. The product fractions were combined and concentrated to dryness. The resultant white powder was re-dissolved in DCM (3 mL) and washed with saturated bicarbonate solution (1×5 mL). The aqueous fraction was back extracted with 70/30 chloroform/isopropanol (2×5 mL). The organic phases were combined, dried over MgSO$_4$, filtered and concentrated to give 1-((1R,5R,7R,8S)-8-((4-chlorobenzyl)oxy)-5-(hydroxymethyl)-6-oxa-3-azabicyclo[3.2.1]octan-7-yl)-thymidine (17 mg, 0.042 mmol, 69.8% yield) as a white powder.

$^1$H NMR (400 MHz, Acetonitrile-d3) δ 8.05 (q, J=1.2 Hz, 1H), 7.36 (s, 4H), 5.94 (s, 1H), 4.52 (dd, J=38.6, 11.9 Hz, 2H), 4.14 (d. J=5.1 Hz, 1H), 3.58 (dd, J=33.9, 12.3 Hz, 2H), 3.09 (d, J=12.7 Hz, 1H), 2.89 (d, J=13.0 Hz, 1H), 2.75 (dd. J=13.0, 3.2 Hz, 1H), 2.57-2.50 (m, 1H), 2.34 (d, J=13.0 Hz, 1H), 1.98-1.90 (m, 2H), 1.81 (d. J=1.1 Hz, 3H). $^{13}$C NMR (101 MHz, CD$_3$CN) δ 165.01, 151.22, 138.07, 136.98, 133.72, 130.05, 129.23, 109.19, 87.42, 85.04, 73.06, 71.38, 61.04, 45.85, 43.60, 41.58, 12.71.

(1R,5R,7R,8S)-tert-butyl 8-((4-chlorobenzyl)oxy)-7-(thymidin-yl)-5-(hydroxymethyl)-6-oxa-3-azabicyclo[3.2.1]octane-3-carboxylate (25)

(1R,5R,7R,8S)-tert-butyl 8-((4-chlorobenzyl)oxy)-7-(thymidin-yl)-5-(((methylsulfonyl)oxy)methyl)-6-oxa-3-azabicyclo[3.2.1]octane-3-carboxylate (1.0 g, 1.47 mmol) and sodium benzoate (0.63 g, 4.40 mmol) were weighed into a 100 mL round bottomed flask with a stir-bar. The flask was charged with DMF (10 mL), septum sealed and heated to 100° C. for 40 hours. TLC (65% EtOAc/Hex) indicated that the reaction was complete. The mixture was diluted with saturated sodium bicarbonate (100 mL) and extracted with ethyl acetate (3×50 mL). The organic phases were combined and washed with brine, dried over Na$_2$SO$_4$, filtered and concentrated in vacuo to give a tan solid that was dissolved in a mixture of dioxane (20 mL) and 2M NaOH (3 mL). The mixture was warmed to 50° C. overnight. The reaction mixture was concentrated in vacuo to a solid and applied to a 50 g Biotage SNAP silica column and eluted using a gradient of 50-100% EtOAc in hexanes over 7 column volumes and holding at 100% EtOAc for 7 column volumes. The product containing fractions were combined and concentrated in vacuo to yield (1R,5R,7R,8S)-tert-butyl 8-(hydroxy)-7-(thymidin-yl)-5-(hydroxymethyl)-6-oxa-3-azabicyclo[3.2.1]octane-3-carboxylate (0.63 g, 1.24 mmol, 84.6%) as a white foam.
ESI-MS: 506 (M)⁻

(1R,5R,7R,8S)-8-Hydroxy-7-(thymidin-yl)-5-(hydroxymethyl)-3-(2,2,2-trifluoroacetyl)-6-oxa-3-azabicyclo[3.2.1]octane (26)

(1R,5R,7R,8S)-tert-butyl 8-(hydroxy)-7-(thymidin-yl)-5-(hydroxymethyl)-6-oxa-3-azabicyclo[3.2.1]octane-3-carboxylate (0.6 g, 1.18 mmol) was dissolved in ethanol (25 mL) and transferred to a 500 mL Parr hydrogenation vessel. Pearlman's Catalyst (0.35 g) and a single drop of glacial acetic acid was added at once and the mixture was shaken on a Parr hydrogenator under a hydrogen atmosphere (40 psi) for 4 hours. TLC indicated that the reaction was complete and spot-to-spot (5% methanol in DCM). The mixture was carefully filtered through a bed of celite that was previously washed with several volumes of methanol. The celite bed was washed with ethyl acetate (100 mL) and ethanol (100 mL). The filtrate was concentrated in vacuo to approximately 5 mL and transferred to a 20 mL glass scintillation vial. The material was taken to dryness in vacuo to give an off white powder that was used without further purification.

The glass scintillation vial was fitted with a micro stir bar and charged with dichloromethane (2 mL) and trifluoroacetic acid (2 mL). The vial was sealed and set to stir for 30 minutes. The micro stir bar was removed and the volatiles removed in vacuo. The resultant oil was co-evaporated with toluene (2×4 mL), methanol (1×4 mL) and DCM (2×4 mL) to give an off white powder/residue in the vial. The residue was re-dissolved in methanol (5 mL) with a micro stir bar in the scintillation vial. Ethyl trifluoroacetate (2.00 mL, 16.9 mmol) and TEA (0.410 mL, 3.54 mmol) were added, the vial was sealed and the mixture set to stir overnight. After 20 hours, TLC of the mixture showed that the starting material was completely consumed and a new product had been formed. The volatiles were removed in vacuo. The residue was co-evaporated with EtOAc (2×5 mL) and toluene (2×5 mL) to give (1R,5R,7R,8S)-8-Hydroxy-7-(thymidin-yl)-5-(hydroxymethyl)-3-(2,2,2-trifluoroacetyl)-6-oxa-3-azabicyclo[3.2.1]octane (0.30 g, 79.8%) for use directly in the next tritylation step. ¹H NMR analysis of the crude material indicated that a mixture of diastereomers in an approximately 55:45 ratio were formed (by integration of anomeric signals).

(1R,5R,7R,8S)-8-Hydroxy-7-(thymidin-yl)-5-((4,4'-dimethoxytrityloxy)methyl)-3-(2,2,2-trifluoroacetyl)-6-oxa-3-azabicyclo[3.2.1]octane (27)

5'-O-DMTr-aCBBN(tfa)
In a 50 mL round bottomed flask, (1R,5R,7R,8S)-8-Hydroxy-7-(thymidin-yl)-5-(hydroxymethyl)-3-(2,2,2-trifluoroacetyl)-6-oxa-3-azabicyclo[3.2.1]octane (0.28 g, 0.74 mmol) was co-evaporated with pyridine (2×10 mL). The flask was charged with anhydrous pyridine (7 mL) and DMTr-Cl was added, at once, the solution. The flask was sealed and the mixture stirred overnight at room temperature. TLC revealed that all starting material was consumed (95% EtOAc/Hex or 5% MeOH/DCM). The reaction was quenched by addition of methanol (0.5 mL) and stirring continued for 30 minutes, followed by addition of aqueous saturated NaHCO3 (30 mL). The aqueous phase was extracted with EtOAc (3×20 mL). The organic phases were combined and washed with brine (1×20 mL), dried over Na₂SO₄, filtered and concentrated in vacuo to give a tan foam. The solids were dissolved in a minimum amount of DCM and applied to a 50 g Biotage silica SNAP column previously treated with 60 mL of a 25% solution of TEA in hexanes and equilibrated with 200 mL of 30% EtOAc/Hex. The product was eluted off the column with a gradient of 30-100% EtOAc in Hexanes over 10 column volumes followed by 4 column volumes of 100% EtOAc. Fractions containing pure product were combined and concentrated to give DMTr-(N-tfa)-aminoCBBN as a white foam. Both ¹H and ¹⁹F NMR indicates two distinct diastereomers. Asterisks in the ¹H NMR tabulation denotes peaks where diastereomeric protons are resolved in an approximately 55:45 ratio.

¹H NMR (400 MHz, Chloroform-d) δ 7.72* (d, J=1.0 Hz, 1H), 7.68* (d, J=1.1 Hz, 1H), 7.49-7.38 (m, 4H), 7.35-7.20 (m, 14H), 6.93-6.78 (m, 8H), 5.73* (s, 1H), 5.68* (s, 1H), 4.55-4.36 (m, 3H), 4.05* (s, 2H), 4.01* (s, 2H), 3.94-3.84 (m, 1H), 3.79 (q, J=0.7 Hz, 13H), 3.64 (t, J=12.0 Hz, 1H), 3.57-3.38 (m, 4H), 3.38-3.15 (m, 4H), 2.70* (d, J=3.6 Hz, 1H), 2.65* (t, J=4.0 Hz, 1H), 1.47* (s, 3H), 1.41* (s, 3H), 1.28 (bs, 2H). ¹⁹F NMR (376 MHz, cdcl₃) δ −68.61, −68.90.
ESI MS: 680 (M)⁻

(1R,5R,7R,8S)-7-(thymidin-yl)-5-((4,4'-dimethoxytrityloxy)methyl)-3-(2,2,2-trifluoroacetyl)-6,8-oxa-3-azabicyclo[3.2.1]octane-8-O-(2-cyanoethyl)-N,N-diisopropylphosphoramidite (28)

5'-O-DMTr-aCBBN(tfa) Amidite
5'-O-DMTr-aCBBN(tfa) (0.32 g, 0.47 mmol) was weighed in a 100 mL round-bottomed flask fitted with a stir bar. The flask was charged with dichloromethane (7 mL) and set to stir. 2-Cyanoethyl N,N,N',N'-tetraisopropylphosphordiamidite (0.283 g, 0.94 mmol) was weighed in a syringe and added at once to the solution followed by 4,5-dicyanoimidazole (55.44 mg, 0.47 mmol). The flask was immediately septum sealed and allowed to stir overnight. In process TLC at 20 hours revealed that there was only a trace of starting material, with two new spots arising that were trityl positive and appeared to char similarly to starting nucleoside when treated with Hanessian's stain following development with 5% methanol/DCM w/UV visualization. Reaction was quenched by the addition of aqueous saturated NaHCO3 solution (50 mL). The aqueous phase was extracted with ethyl acetate (4×20 mL). The organic phases were combined and extracted with aqueous saturated NaHCO₃ solution (2×50 mL) and brine (1×20 mL). The organic phase was dried over Na₂SO₄, filtered and concentrated to give a colorless oil. The crude product was dissolved in a minimum amount of DCM and applied to a 50 g Biotage silica SNAP column previously treated with 60 mL of a 25% solution of TEA in hexanes and equilibrated with 150 mL of 30% ethyl acetate/hexanes. The product was eluted off the column with a gradient of 30-100% EtOAc in Hexanes over 10 column volumes followed by 4 column volumes of 100% EtOAc. Fractions containing pure product were combined and concentrated to give DMTr-(N-tfa)-aminoCBBN amidite as a white foam. ³¹P and ¹H NMR indicate the presence of four distinct products, as expected, each corresponding to a separate stereoisomer arising from the tfa protection of the cyclic amine and the phosphitylation reaction.

³¹P NMR (162 MHz, CD3CN) δ 150.03, 149.97, 147.46. Relative intensity of 1:1:2. ¹⁹F NMR (376 MHz, CD3CN) δ −69.30, −69.31, −69.47. −69.47.
ESI MS: 904.8 (M+Na⁺)⁺

Example 2

Production of 2'-C-Bridged Bicyclic Nucleoside Phosphoramidites and Conjugates

Figure 4A:
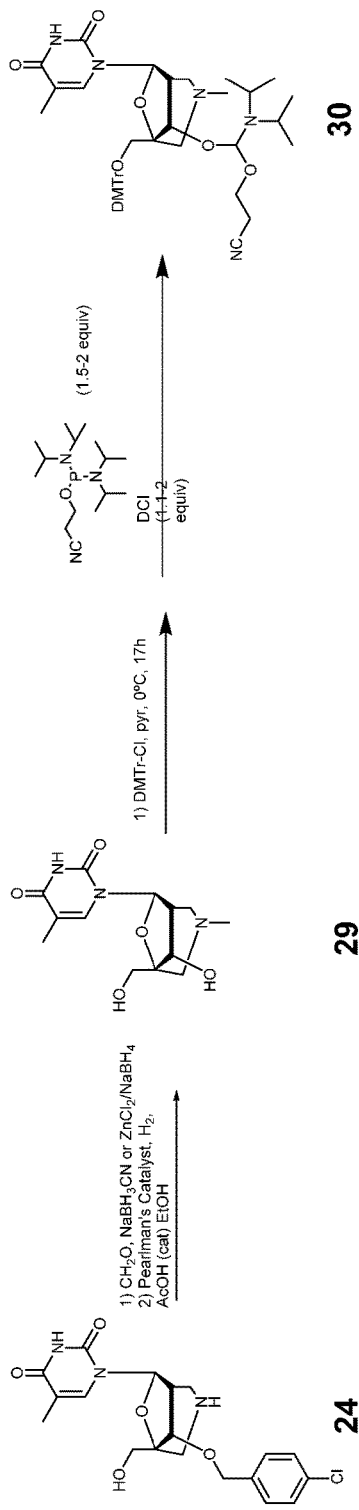
FIG. 4A illustrates the synthesis of an exemplary dimethoxytrityl (DMTr)-protected amine 2'-C-Bridged Bicyclic Nucleoside phosphoramidite.

Synthesis of Dimethoxytrityl (DMTr)-protected Amine 2'-C-bridged Bicyclic Nucleoside Phosphoramidite (30) as Illustrated in FIG. 4A Compound 30 was synthesized from compound 24 by subjecting compound 24 to reductive amination in the presence of formaldehyde and sodium cyanoborohydride (J. Org. Chem., 1972, 37, pp 1673-1674, Borch conditions) or similar reducing agents, such as ZnCl2/NaBH4. Following reductive methylation, the 3'-OH was unmasked by dissolving the product in ethanol and subjecting the mixture to catalytic hydrogenation using Pearlman's Catalyst in a hydrogen atmosphere (40 psi) and a trace of acetic acid. The crude reduction mixture can be directly tritylated in a cooled pyridine solution by dropwise addition of a pyridine solution of 4,4'-dimethoxytrityl chloride. The mixture was allowed to stir overnight to give the 5'-dimethoxytrityl-nuceoside which was purified by using silica gel column chromatography. The purified nucleoside was then subjected to phophitylation using 2-Cyanoethyl-N,N,N',N'-tetraisopropyl-phosphordiamidite (1.5-2 equiv) and 4,5-dicyanoimidazole (1.1-2 equiv.) as a coupling catalyst in dichloromethane. The reaction was allowed to stir at least 24 hours and as long as 48 hours until quenched with saturated sodium bicarbonate solution and subjected to column chromatography to give phosphoramidite 30. Compound 30 is suitable for use in automated solid phase oligonucleotide synthesis for incorporation into a synthetic oligonucleotide.

Figure 4B:
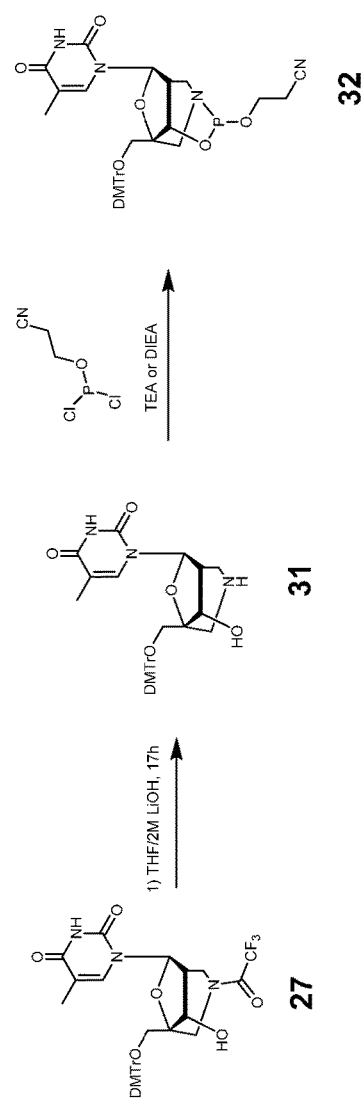
FIG. 4B illustrates the synthesis of an internal phosphoramidite derivative of a DMTr-protected amine 2'-C-Bridged Bicyclic Nucleoside.

Synthesis of an Internal Phosphoramidite Derivative of a DMTr-protected Amine 2'-C-bridged Bicyclic Nucleoside (32) as Illustrated in FIG. 4B Compound 32 was synthesized from compound 27 in two steps by first subjecting compound 27 to alkaline hydrolysis of the trifluoroacetamide protecting group using an aqueous LiOH/THF solution. The aqueous solution was diluted with saturated sodium bicarbonate and can be extracted with ethyl acetate. The crude nucleoside can then be subjected to phosphitylation with 2-cyanoethyl phosphorodichloridite pretreated with 4-10 equivalents of anhydrous TEA or DIEA. The resultant phosphoramidite was purified via silica gel column chromatography where the silica gel was pretreated with several column volumes of 3% TEA in Hexanes prior to eluting with the appropriate mobile phase. The phosphoramidite must also be stored with a trace of TEA to prevent decomposition. Compound 32 is suitable for use in automated solid phase oligonucleotide synthesis for incorporation into a synthetic oligonucleotide. Care must be taken to use a suitable capping reagent after the coupling and oxidation steps in automated solid phase oligonucleotide synthesis. Acetic anhydride will produce a final deprotected oligonucleotide bearing an acetamide on the bicyclic nitrogen. Other activated esters or anhydrides can be used to directly make a conjugate at that bicyclic nitrogen center before proceeding with the remainder of the automated solid phase oligonucleotide synthesis.

Synthesis of DMTr-protected Fatty Acid Conjugated Amine 2'-C-bridged Bicyclic Nucleoside (33) as Illustrated in FIG. 4C Compound 33 was directly synthesized from compound 31 by utilizing a transient protection of the 3'-OH with TMS-Cl in pyridine solution. After 4 hours of reaction, the mixture was cooled in an ice bath and stearoyl chloride was added dropwise with stirring. The reaction mixture was allowed to come to room temperature overnight. The reaction mixture was quenched by addition of saturated sodium bicarbonate solution, extracted with ethyl acetate and the organics were dried. The crude material was concentrated re-dissolved in THF followed by treatment with a solution of TBAF in THF (1.25 equiv). The reaction mixture was concentrated and directly subjected to silica gel column chromatography to give compound 33. Compound 33 is amenable to phosphoramidite synthesis as described for the conversion of compound 27 to 28.

Synthesis of DMTr-protected Sugar Conjugated Amine 2'-C-bridged Bicyclic Nucleoside as Illustrated in FIG. 4D Compound 34 was directly synthesized from compound 31 by utilizing the HBTU as the coupling reagent, 5-[(2S, 3S,4R,5R,6R)-4,5-Diacetoxy-6-(acetoxymethyl)-3-acetylaminotetrahydro-2H-pyran-2-yl]valeric acid (GalNAc-C5 acid, prepared via procedure described in WO 2009073809) and at least 1 equivalent of N-methylmorpholine in DMF solution. Upon completion of the reaction (4-17 hours), the mixture was diluted with saturated bicarbonate solution and extracted with ethyl acetate. The organics were dried, the crude material concentrated and the residue was directly subjected to silica gel column chromatography to give compound 33. Compound 33 is amenable to phosphoramidite synthesis as described for the conversion of compound 27 to 28.

Example 3

Synthesis of Oligonucleotides Bearing 2'-C-bridged Bicyclic Nucleotides

General Synthesis Methodology

Short strands of oligonucleotides bearing sugar and base modifications can be prepared once the modified nucleoside is synthesized and the free 5' and 3'-hydroxyl groups are masked with appropriate reactive groups to become a nucleotide monomer. For example, automated solid phase synthesis using phosphoramidite chemistry may be used (see McBride et al., Tetrahedron Letters 24:245-248 (1983) and Sinha et al., Tetrahedron Letters 24:5843-5846 (1983)). Phosphoramidite chemistry, together with related methods such as hydrogen phosphonate chemistry, has been extensively reviewed with respect to their uses in oligonucleotide chemistry (see, for example, Beaucage et al., Tetrahedron 48:2223-2311(1992)). During solid phase oligonucleotide synthesis, a series of nucleotide monomers are sequentially attached, via their phosphoramidite derivatives, in a predetermined order to either, depending on the direction of chain extension, the 5'-functional group or the 3'-functional group of the growing oligonucleotide strand.

The oligonucleotide strand is anchored to an insoluble moiety such as controlled pore glass or polystyrene resin beads. The method of attachment of each monomer is generally comprised of the following steps 1 through 5. Step 1 involves the protection of the reactive functionality. The common reactive functionality is the 5'-hydroxyl group of the terminal nucleoside. This functionality is usually protected with a 4,4'-dimethoxytrityl (DMT) moiety that can be removed via acid treatment. One of the features of the DMT moiety is that it forms a bright orange DMT cation during acid deprotection. This cation effectively serves as reporter group that can be monitored at a wavelength between 480 and 500 nm for the purpose of judging the completeness of the previous coupling step. Most commercially available automated synthesizers have the capability to monitor the released DMT cation. This data gives the operator an instant indication of whether or not the synthesis failed at any given step. Step 2 involves the coupling by addition of a phosphoramidite derivative and an activator. The phosphoramidite derivative is usually a nucleoside phosphoramidite. However, it may also be a phosphoramidite derivatized with a different organic moiety. Step 3 involves the capping of unreacted terminal functional groups. This step introduces an inert protective group that prevents further coupling to failure sequences. Step 4 involves oxidation of the newly formed phosphorous nucleotide backbone linkage from the trivalent phosphite to the stable pentavalent state. This oxidation step can be performed with either an oxygen-based oxidant that results in a phosphate nucleotide or a sulfurizing oxidant that results in a phosphorothioate nucleotide. Step 5 involves a repetition of the process after a washing step.

Truncated, 16 nucleotide sequence complementary to a nucleotide sequence of human miR-208a was synthesized in 1 μmol scale on a MerMade-12 automated oligonucleotide synthesis system (Bioautomation, Plano, Tex., USA). The synthesizer was operated using standard detrytilation, activator and capping solutions, known to those skilled in the art. Oligonucleotide chain elongation was affected using single couplings of 420 seconds for each deoxynucleotide amidite, double couplings lasting a total of 900 seconds for LNA amidites and triple couplings lasting a total of 1800 seconds for novel nucleoside amidites, such as the DMTr-aCBBN(tfa) amidite. Oxidation with either 0.025 M Iodine solution or 0.2 M PADS oxidation solution after each coupling cycle was performed to generate either phosphodiester or phosphorothioate internucleotide linkages, respectively. The unmodified anti-208a DNA sequence incorporates nine 2'-deoxythymidine residues which were selectively replaced with thymidine LNA (IT), thymidine oxoCBBN (bT), cytidine oxoCBBN (bC) or thymidine aminoCBBN (abT) nucleotides. Thymidine LNA amidite was purchased from commercial sources and matches reported spectroscopic data (see Singh, S. K.; Nielsen. P.; Koshkin, A. A.; Wengel, J. Chem. Commun. 1998, 455-6). The Thymidyl-2'-C,4'-C-Bridged Bicyclonucleoside (thymidine oxoCBBN, bT) and cytidyl-2'-C,4'-C-Bridged Bicyclonucleoside (cytidine oxoCBBN, bC) was synthesized according to a literature procedure and all spectroscopic data matched reported values (see U.S. Pat. No. 6,403,566, Wang, G., Girardet J., Gunic, E. Tetrahedron 55, 1999, 7707-7724). The balance of the nucleotides was comprised of 2'-deoxynucleotides or LNA nucleotides with bases corresponding to the natural anti-208a RNA sequence. Phosphorothioate internucleotide linkages are denoted with an "s" following the base (e.g., abTs or dGs), while no letter following a base indicates a phosphodiester internucleotide linkage (e.g., abT or dG)

Preparation of Compound M-11915:
dC.dT.dT.dT.dT.dT.dG.dC.abT.dC.dG.dT.dC.dT.dT.
dA Phosphoramidite Reagent (28) was used in the synthesis of a singly modified aminoCBBN oligonucleotide. The oligonucleotide was synthesized using a Bioautomation MerMade-12 automated oligonucleotide synthesis system. The synthesis was performed according to the manufacturer's recommendations in DMT-ON mode employing commercial synthesis reagents and 0.025 M iodine solution. The phosphoramidite reagents were added as a 0.1 M solution in acetonitrile during the appropriate coupling cycle as described previously. The cleavage of the oligonucleotide from the support was accomplished via heating of the CPG bound oligonucleotide with a solution of concentrated aqueous ammonium hydroxide at 55° C. for 17 hours. The resultant aqueous solution of oligonucleotide was further purified by loading the crude DMT-ON oligonucleotide solution on a Waters Sep-Pak® Vac C18 cartridge and eluting using a standard DMT-ON oligonucleotide desalting procedure known to those knowledgeable in the art. The characterization of product was performed by HPLC-MS mass spectrometry utilizing an XBridge OST C18 2.5 um column fitted to a Waters AllianceMD HPLC with a Waters Acuity SQ Detector utilizing standard methods known to those knowledgeable in the art: calcd 4845.2. found 4844.0 (M)⁻.

Preparation of Compound M-11916:
dC.dT.dT.dT.dT.abT.dG.dC.abT.dC.dG.dT.dC.dT.
dT.dA Phosphoramidite Reagent (28) was used in the synthesis of a double modified aminoCBBN oligonucleotide. The oligonucleotide was synthesized using a Bioautomation MerMade-12 automated oligonucleotide synthesis system. The synthesis was performed according to the manufacturer's recommendations in DMT-ON mode employing commercial synthesis reagents and 0.025 M iodine solution. The phosphoramidite reagents were added as a 0.1 M solution in acetonitrile during the appropriate coupling cycle as described previously. The cleavage of the oligonucleotide from the support was accomplished via heating of the CPG bound oligonucleotide with a solution of concentrated aqueous ammonium hydroxide at 55° C. for 17 hours. The resultant aqueous solution of oligonucleotide was further purified by loading the crude DMT-ON oligonucleotide solution on a Waters Sep-Pak® Vac C18 cartridge and eluting using a standard DMT-ON oligonucleotide desalting procedure known to those knowledgeable in the art. The characterization of product was performed by HPLC-MS mass spectrometry utilizing an XBridge OST C18 2.5 um column fitted to a Waters AllianceMD HPLC with a Waters Acuity SQ Detector utilizing standard methods known to those knowledgeable in the art: calcd 4886.2. found 4885.2 (M)⁻.

Preparation of Compound M-11917:
dC.dT.dT.dT.abT.abT.dG.dC.abT.dC.dG.dT.dC.dT.
dT.dA Phosphoramidite Reagent (28) was used in the synthesis of a triple modified aminoCBBN oligonucleotide. The oligonucleotide was synthesized using a Bioautomation MerMade-12 automated oligonucleotide synthesis system. The synthesis was performed according to the manufacturer's recommendations in DMT-ON mode employing commercial synthesis reagents and 0.025 M iodine solution. The phosphoramidite reagents were added as a 0.1 M solution in acetonitrile during the appropriate coupling cycle as previously described. The cleavage of the oligonucleotide from the support was accomplished via heating of the CPG bound oligonucleotide with a solution of concentrated aqueous ammonium hydroxide at 55° C. for 17 hours. The resultant aqueous solution of oligonucleotide was further purified by loading the crude DMT-ON oligonucleotide solution on a Waters Sep-Pak® Vac C18 cartridge and eluting using a standard DMT-ON oligonucleotide desalting procedure known to those knowledgeable in the art. The characterization of product was performed by HPLC-MS mass spectrometry utilizing an XBridge OST C18 2.5 um column fitted to a Waters AllianceMD HPLC with a Waters Acuity SQ Detector utilizing standard methods known to those knowledgeable in the art: calcd 4927.3. found 4926.1 (M)⁻.

Preparation of Compound M-11918:
dC.dT.dT.dT.abT.abT.dG.dC.dT.dC.dG.dT.dC.dT.
dT.dA Phosphoramidite Reagent (28) was used in the synthesis of a double modified aminoCBBN oligonucleotide. The oligonucleotide was synthesized using a Bioautomation MerMade-12 automated oligonucleotide synthesis system. The synthesis was performed according to the manufacturer's recommendations in DMT-ON mode employing commercial synthesis reagents and 0.025 M iodine solution. The phosphoramidite reagents were added as a 0.1 M solution in acetonitrile during the appropriate coupling cycle as previously described. The cleavage of the oligonucleotide from the support was accomplished via heating of the CPG bound oligonucleotide with a solution of concentrated aqueous ammonium hydroxide at 55° C. for 17 hours. The resultant aqueous solution of oligonucleotide was further purified by loading the crude DMT-ON oligonucleotide solution on a Waters Sep-Pak® Vac C18 cartridge and eluting using a standard DMT-ON oligonucleotide desalting procedure known to those knowledgeable in the art. The characterization of product was performed by HPLC-MS mass spectrometry utilizing an XBridge OST C18 2.5 um column fitted to a Waters AllianceMD HPLC with a Waters Acuity SQ Detector utilizing standard methods known to those knowledgeable in the art: calcd 4886.2. found 4885.0 (M)⁻.

Preparation of Compound M-11919:
lCs.dTs.dTs.dTs.abTs.abTs.dGs.lCs.dTs.lCs.lGs.dTs.
lCs.dTs.lTs.lA Phosphoramidite Reagent (28) was used in the synthesis of the chimeric DNA/LNA/aminoCBBN oligonucleotide. The oligonucleotide was synthesized using a Bioautomation MerMade-12 automated oligonucleotide synthesis system. The synthesis was performed according to the manufacturer's recommendations in DMT-ON mode employing commercial synthesis reagents, exchanging 0.2 M PADS in 1:1 Pyridine/ACN for the oxidizing solution. The phosphoramidite reagents were added as a 0.1 M solution in acetonitrile during the appropriate coupling cycle as previously described. The cleavage of the oligonucleotide from the support was accomplished via heating of the CPG bound oligonucleotide with a solution of concentrated aqueous ammonium hydroxide at 55° C. for 17 hours. The resultant aqueous solution of oligonucleotide was further purified by loading the crude DMT-ON oligonucleotide solution on a Waters Sep-Pak® Vac C18 cartridge and eluting using a standard DMT-ON oligonucleotide desalting procedure known to those knowledgeable in the art. The characterization of product was performed by HPLC-MS mass spectrometry utilizing an XBridge OST C18 2.5 um column fitted to a Waters AllianceMD HPLC with a Waters Acuity SQ Detector utilizing standard methods known to those knowledgeable in the art: calcd 5379.3. found 5378.3 (M)⁻.

Preparation of Compound M-11920: lCs.dTs.dTs.
.dTs.lTs.lTs.dGs.lCs.dTs.lCs.lGs.dTs.lCs. dTs.abT-
s.lA Phosphoramidite Reagent (28) was used in the synthesis of the chimeric DNA/LNA/aminoCBBN oligonucleotide. The oligonucleotide was synthesized using a Bioautomation MerMade-12 automated oligonucleotide synthesis system. The synthesis was performed according to the manufacturer's recommendations in DMT-ON mode employing commercial synthesis reagents, exchanging 0.2M PADS in 1:1 Pyridine/ACN for the oxidizing solution. The phosphoramidite reagents were added as a 0.1 M solution in acetonitrile during the appropriate coupling cycle described above in "General Synthetic Methodology of Truncated Nucleotides". The cleavage of the oligonucleotide from the support was accomplished via heating of the CPG bound oligonucleotide with a solution of concentrated aqueous ammonium hydroxide at 55° C. for 17 hours. The resultant aqueous solution of oligonucleotide was further purified by loading the crude DMT-ON oligonucleotide solution on a Waters Sep-Pak® Vac C18 cartridge and eluting using a standard DMT-ON oligonucleotide desalting procedure known to those knowledgeable in the art. The characterization of product was performed by HPLC-MS mass spectrometry utilizing an XBridge OST C18 2.5 um column fitted to a Waters AllianceMD HPLC with a Waters Acuity SQ Detector utilizing standard methods known to those knowledgeable in the art: calcd 5366.3. found 5365.3 (M)⁻.

Preparation of Compound M-10930
dC.dT.dT.dT.dT.dT.dG.dC.bT.dC.dG.dT.dC.dT.dT.
dA Thymidyl-2'-C,4'-C-Bridged Bicyclonucleoside Phosphoramidite (see, for example, U.S. Pat. No. 6,403,566, Wang, G., Girardet. J., Gunic, E. Tetrahedron 55, 1999, 7707-7724) was used in the synthesis of a singly modified oxoCBBN oligonucleotide. The oligonucleotide was synthesized using a Bioautomation MerMade-12 automated oligonucleotide synthesis system. The synthesis was performed according to the manufacturer's recommendations in DMT-ON mode employing commercial synthesis reagents, and 0.025 M iodine solution. All phosphoramidite reagents were added as a 0.1 M solution in acetonitrile during the appropriate coupling cycle as previously described. The cleavage of the oligonucleotide from the support was accomplished via heating of the CPG bound oligonucleotide with a solution of concentrated aqueous ammonium hydroxide at 55° C. for 17 hours. The resultant aqueous solution of oligonucleotide was further purified by loading the crude DMT-ON oligonucleotide solution on a Waters Sep-Pak® Vac C18 cartridge and eluting using a standard DMT-ON oligonucleotide desalting procedure known to those knowledgeable in the art. The characterization of product was performed by HPLC-MS mass spectrometry utilizing an XBridge OST C18 2.5 um column fitted to a Waters AllianceMD HPLC with a Waters Acuity SQ Detector utilizing standard methods known to those knowledgeable in the art: calcd 4846.1. found 4845.8 (M)⁻.

Preparation of Compound M-10924
bC.bT.bT.bT.bT.bT.dG.bC.bT.bC.dG.bT.bC.bT.bT.
dA Thymidyl-2'-C,4'-C-Bridged Bicyclonucleoside Phosphoramidite and N-Bz-Cytidyl-2'-C,4'-C-Bridged Bicyclonucleoside Phosphoramidite (see, for example, U.S. Pat. No. 6,403,566, Wang, G., Girardet, J., Gunic, E. Tetrahedron 55, 1999, 7707-7724) was used in the synthesis of a singly modified oxoCBBN oligonucleotide. The oligonucleotide was synthesized using a Bioautomation MerMade-12 automated oligonucleotide synthesis system. The synthesis was performed according to the manufacturer's recommendations in DMT-ON mode employing commercial synthesis reagents, and 0.025 M iodine solution. All phosphoramidite reagents were added as a 0.1 M solution in acetonitrile during the appropriate coupling cycle as previously described. The cleavage of the oligonucleotide from the support was accomplished via heating of the CPG bound oligonucleotide with a solution of concentrated aqueous ammonium hydroxide at 55° C. for 17 hours. The resultant aqueous solution of oligonucleotide was further purified by loading the crude DMT-ON oligonucleotide solution on a Waters Sep-Pak® Vac C18 cartridge and eluting using a standard DMT-ON oligonucleotide desalting procedure known to those knowledgeable in the art. The characterization of product was performed by HPLC-MS mass spectrometry utilizing an XBridge OST C18 2.5 um column fitted to a Waters AllianceMD HPLC with a Waters Acuity SQ Detector utilizing standard methods known to those knowledgeable in the art: calcd 5350.6. found 5350.2 (M)⁻.

Example 4

Functional Characterizations of Oligonucleotides Bearing 2'-C-bridged Bicyclic Nucleotides Determination of Melting Temperature (Tm)

Melting temperature (Tm) is a critical parameter when designing synthetic oligonucleotide sequences as drugs directed towards antisense and microRNA targets. There is generally no specific Tm threshold above or below which determines activity. However, it is recognized that Tm must be significantly elevated for antisense and microRNA inhibitor oligonucleotide drugs. Furthermore, chemical modifications of the nucleotide backbones of synthetic oligonucleotide drugs (e.g., phosphorothioates) are often times used to impart stability against biodegradation in vivo. Nevertheless, most nucleotide phosphate backbone modifications often times cause decreases in the Tm of an oligonucleotide drug duplexed with its target. Accordingly, sufficient increases in the Tm of a synthetic oligonucleotide drug against its target sequence, over that inherent in natural DNA or RNA, 2'-OMe RNA, and other similar nucleotide units, are required for the synthetic oligonucleotide drug to have sufficient specificity, target engagement and ultimately downstream regulation of cellular processes controlled by the target.

The melting temperature (Tm) of modified 16 nucleotide phosphodiester strands were determined and compared to the Tm of identical 16 nucleotide sequences having natural phosphodiester DNA nucleotides. Specifically, the relative aminoCBBN melting temperature (Tm) compared to the 2'-deoxynucleoside or oxoCBBN nucleoside with the same nucleobase was determined on a per incorporation basis by determining the difference between the melting temperature of the amino-modified 16 nucleotide length phosphodiester strand and that of the identical 16 nucleotide sequence utilizing either the 2'-deoxynucleoside or oxoCBBN phosphodiester DNA nucleotide. Tm differences of substitutions were compared only when they were placed in the same position of the sequence. Comparable values for amino-LNA and its oxo-LNA counterpart were obtained through literature references (see Singh, S. K., Kumar, R., Wengel J. J. Org. Chem., Vol. 63, No. 26, 1998).

For example, the modified anti-208a oligonucleotides were annealed to the complementary sequence, twenty-two nucleotides in length, comprised of RNA nucleosides and a phosphate backbone. The complementary sequence was identical to the endogenous mature miRNA. Thermal denaturation temperatures (Tm) were measured as a maximum of the first derivative plot of melting curvex (A260 vs. Temp). The duplexes were constituted at 1 µM in a 0.9% NaCl buffer. Temperature was ramped from 25° C. to 95° C. at 1° C./min and OD's at 260 nm were read once per 30 seconds. Tm values are averages of at least two measurements.

Duplex melting temperatures for various modifications of a 16 nucleotide sequence, complementary to a nucleotide sequence of mature human miR-208a were measured using a Varian Cary 1E UV-Vis Spectrophotometer. Anti-miRNA 208a oligonucleotide sequences tested included a fully DNA phosphodiester (compound M-10931), four DNA phosphodiester oligonucleotides with 1, 2 or 3 aminoCBBN thymidine residues in place of dT residues (compounds M-1915, M-1916, M-1917, and M-11918), mixed 9 LNA/7 DNA phosphorothioate oligonucleotide (compound M-10101), and 2 mixed LNA/DNA/aminoCBBN phosphorothioate oligonucleotides where LNA thymidines of the parent compound, compound M-10101, were replaced with either 1 or 2 aminoCBBN residues (compounds M-11919 and M-11920). Duplexes were constituted at 1 µM in 0.9% NaCl. Temperature was ramped from 25° C. to 95° C. at 1° C./min and OD's at 260 nm were read once per 30 seconds.

Phosphodiester oligonucleotides with aminoCBBN modifications uniformly had higher melting temperature, therefore higher affinity, towards the complimentary sequence than their fully DNA counterpart (see Table 3). Affinity enhancements were on the order of 5-9° C./modification over DNA. These increases in affinity are as good as or better than literature values for LNA and aminoLNA.

TABLE 3 aminoCBBN, Phosphate Backbone Tm Studies, RNA Complement

| Oligo # | Oligo Name | Sequence | Tm | $\Delta T_m$, $DNA$ | $\Delta T_m$/ mod |
|---|---|---|---|---|---|
| 10931 | 208a_DNA_PO | dC;dT;dT;dT;dT;dT;dG;dC;dT; dC;dG;dT;dC;dT;dT;dA | 53.1 | 0 | NA |

TABLE 3-continued aminoCBBN, Phosphate Backbone Tm Studies, RNA Complement

| Oligo # | Oligo Name | Sequence | Tm | ΔT$_m$, DNA | ΔT$_m$/mod |
|---|---|---|---|---|---|
| 10924 | 208a_CBBN_C_T_DNA_16_3_PO | bC;bT;bT;bT;bT;bT;dG;bC;bT; bC;dG;bT;bC;bT;bT;dA | 89.8 | 36.7 | 2.8 |
| 10930 | 208a_1CBBN_DNA_PO | dC;dT;dT;dT;dT;dT;dG;dC;bT; dC;dG;dT;dC;dT;dT;dA | 58.3 | 5.3 | 5.3 |
| 11915 | 208a_1aminoCBBN_DNA_PO | dC;dT;dT;dT;dT;dT;dG;dC;abT; dc;dG;dT;dC;dT;dT;dA | 62.0 | 8.9 | 8.9 |
| 11916 | 208a_2aminoCBBN_DNA_PO | dC;dT;dT;dT;dT;abT;dG;dC;abT; dC;dG;dT;dC;dT;dT;dA | 64.6 | 11.5 | 5.8 |
| 11917 | 208a_3aminoCBBN_DNA_PO | dC;dT;dT;dT;abT;abT;dG;dC;abT; dC;dG;dT;dC;dT;dT;dA | 67.5 | 14.4 | 4.8 |
| 11918 | 208a_2aminoCBBN_DNA_PO_isomer | dC;dT;dT;dT;abT;abT;dG;dC;dT; dC;dG;dT;dC;dT;dT;dA | 63.6 | 10.5 | 5.2 |

TABLE 4

Description of Notations

| deoxy A | dA | oxoCBBN A | bA |
|---|---|---|---|
| deoxy G | dG | oxoCBBN C | bG |
| deoxy C | dC | oxoCBBN C | bC |
| deoxy T | dT | OxoCBBN T | bT |
| Ina A | IA | aminoCBBN A | abA |
| InaG | IG | aminoCBBN G | abG |
| Ina C | IC | aminoCBBN C | abC |
| Ina T | IT | aminoCBBN T | abT |
| deoxy A P = S | dAs | | |
| deoxy G P = S | dGs | | |
| deoxy C P = S | dCs | | |
| deoxy T P = S | dTs | | |
| Ina A P = S | IAs | | |
| InaG P = S | IGs | | |
| Ina C P = S | ICs | | |
| Ina T P = S | ITs | | |

Comparison of the aminoLNA-T to its oxo-analogue, LNA-T, reveals that aminoLNA-T is less stabilizing toward its complement than LNA-T. Similarly, aminoENA-T appears to have very little duplex stabilizing effect over that of its oxo-analogue. Surprisingly, comparison of the aminoCBBN-T to its oxoCBBN-T analogue shows that the aminoCBBN modification is significantly more stabilizing than oxoCBBN-T by 2-4° C./modification (see Tables 5 and FIG. 5). Without wishing to be bound by theory, it is postulated that the 2'-O of LNA, a proton acceptor, has a more stabilizing effect towards duplex hydration and stability than when it is replaced by a proton donor at the 2'-position as in the case of aminoLNA. Conversely, aminoCBBN appears to have a much more positive effect on duplex hydration and stability than its oxoCBBN analogue and offers Tm enhancements not seen in any other 2'4'-Carbon-Bridged Bicyclic Nucleotides. (see FIG. 5).

TABLE 5 aminoCBBN, PS Backbone 10101-like Tm Studies, RNA Complement

| oligo # | Oligo Name | Sequence | T$_m$ | ΔT$_m$, parent | ΔT$_m$/mod |
|---|---|---|---|---|---|
| 10101 | 208a_10101 | ICs;dTs;dTs;dTs;ITs;ITs;dGs;ICs;dTs; ICs;IGs;dTs;ICs;dTs;ITs;IA | 86.7 | NA | NA |
| 11919 | 208a_10101_1aminoCBBN_PS | ICs;dTs;dTs;dTs;ITs;ITs;dGs;ICs;dTs; ICs;IGs;dTs;ICs;dTs;abTs;IA | 80.04 | −6.66 | −6.66 |
| 11920 | 208a_10101_2minoCBBN_PS | ICs;dTs;dTs;dTs;abTs;abTs;dGs;ICs; dTs;ICs;IGs;dTs;ICs;dTs;IT;IA | 85.125 | −1.575 | −0.7875 | amino-Nucleoside, Phosphate Backbone Tm Studies, RNA Complement

| | | | | | |
|---|---|---|---|---|---|
| | DNA_9mer_PO_3LNA-T | dG;IT;dG;dA;IT;dA;IT;dG;dC | 50 | NA | NA |
| | DNA_9mer_PO_3aminoLNA-T | dG;aIT;dG;dA;aIT;dA;aIT;dG;dC | 47 | −1 | −1 |
| 10930 | 208a_1CBBN_DNA_PO | dC;dT;dT;dT;dT;dT;dG;dC;bT;dC;dG; dT;dC;dT;dT;dA | 58.3 | NA | NA |
| 11915 | 208a_1aminoCBBN_DNA_PO | dC;dT;dT;dT;dT;dT;dG;dC;abT;dC; dG;dT;dC;dT;dT;dA | 62.0 | +3.7 | +3.7 |

Cell Culture Activity of Anti-208a Oligonucleotides

A HeLa cell line stably expressing miR-208a was generated. Specifically, a miRNA expression vector (Cell Bio-Labs, Inc.) expressing miR-208a was transfected into HeLa cells. Cells were then selected using a puromycin selection screen and clones which had detectable miR-208a expression as measured by qPCR were isolated (Ct value=~30).

The cells were plated in a black-walled 96 well plate with 10,000 cells per well. After twenty-four hours following plating, the cells were transfected with a dual-luciferase plasmid containing the miR-208a binding site in the 3' UTR of the renilla gene and various miR-208a inhibitors (compounds M-11919, M-11920, and M-10101). Compound M-10591 was a non-targeting control. The cells were incubated for 24 hours at 37° C. and then both firefly (as a transfection normalization) and renilla levels were measured by luminescence using the Dual-Luciferase Reporter Assay System (Promega). Data was normalized to cells treated with only the miR-208a dual luciferase plasmid (psi check 208a). The psi check 2 cells were treated with a dual luciferase plasmid that does not include a miR-208a binding site.

Figure 6:
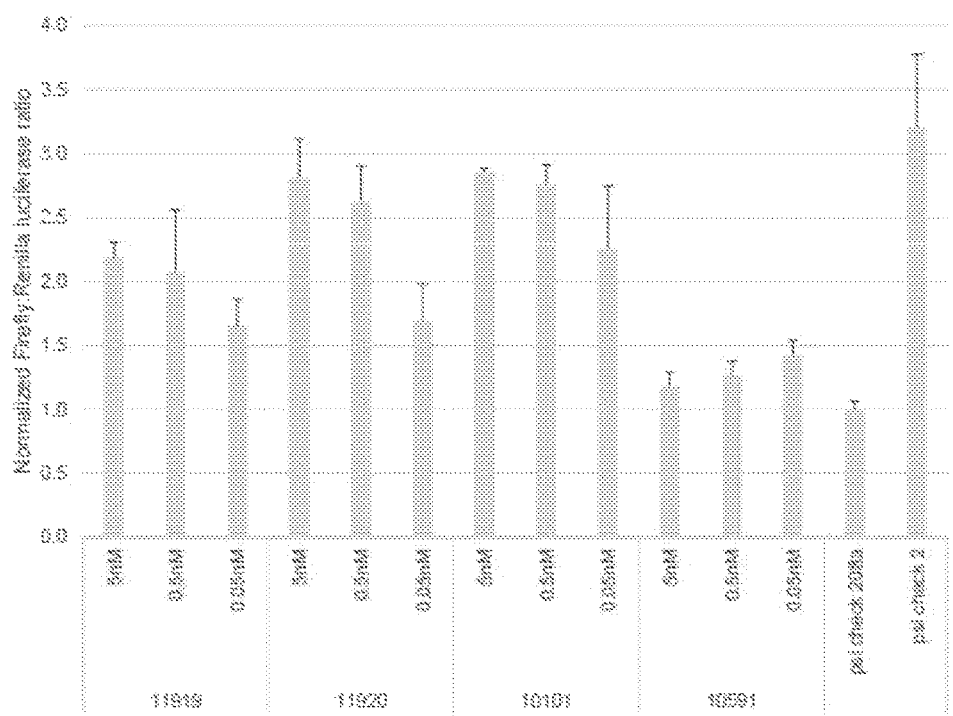
FIG. 6 depicts the efficacy of various miR-208a inhibitors on miR-208a expression as measured in a dual-luciferase reporter assay. The activities of compounds M-10591. M-10101, M-11919, and M-11920 are measured. Compound M-10591 is a non-targeting control. Compound M-10101, a mixed 9 LNA/7 DNA phosphorothioate oligonucleotide, is an optimized miR208a inhibitor. The M10101 compound is described in U.S. Pat. No. 8,642,751, which is herein incorporated by reference in its entirety. Compounds M-10919 and M-11920 are mixed LNA/DNA/aminoCBBN phosphorothioate oligonucleotides where LNA thymidines of the parent compound (M-10101) are replaced with either 1 or 2 aminoCBBN residues, respectively. As shown, compound M-11920, in which multiple LNA residues are replaced with aminoCBBN residues, retains all activity of the optimized M-10101 compound.

Results demonstate that compound M-11920 has comparable activity as compound M-10101, which is an optimized miR208a inhibitor that includes only LNA/DNA bases (see FIG. 6). Accordingly, multiple replacements of LNA residues with aminoCBBN residues result in full retention of miR208a inhibition activity. Compound M-11919 has slightly less activity compared to the other two inhibitors (see FIG. 6). The activity of compound M-11919 correlates with the Tm data which shows that compound M-11919 has less affinity for the miR-208a RNA than the M-11920 compound.

I claim:
1. An oligonucleotide comprising at least one 2'-C-Bridged Bicyclic Nucleotide, wherein said 2'-C-Bridged Bicyclic Nucleotide has the structure of Formula I:

Formula I wherein
X is independently selected from N or S;
W$_1$ and W$_2$ are each independently selected from H, an alcohol protecting group, phosphate ester, phosphorothioate ester, di- or tri-phosphate, phosphoramidite, or one or more nucleotide(s) on the 5' or 3' side;
W$_3$ is independently selected from null, H, O, an amine protecting group, phosphoramidite, phosphoramidate ester, phosphordiamidate ester, methyl, alkyl, cycloalkyl, carboxamide, a sugar, a fatty acid, other molecular conjugate, —C$_{1-4}$(O)R, or —COOR, wherein R is aryl, linear or cyclic alkyl or alkenyl, sugar, fatty acid, or other molecular conjugate such as a drug conjugate; and
B is a nucleobase.
2. The oligonucleotide of claim 1, wherein X is N.
3. The oligonucleotide of claim 1, wherein X is S.
4. The oligonucleotide of claim 1, wherein the alcohol protecting group is selected from 4,4'-dimethoxytrityl, acetyl, silyl, or acid labile ether.
5. The oligonucleotide of claim 1, wherein the amine protecting group is selected from carbobenzyloxy (Cbz), p-methoxybenzyl carbonyl (Moz or MeOZ), tert-butyloxycarbonyl (BOC), 9-fluorenylmethyloxycarbonyl (FMOC), acetyl (Ac), benzoyl (Bz), benzyl (Bn), or trifluoroacetyl (tfa).
6. The oligonucleotide of claim 1, wherein the nucleobase is a purine base.
7. The oligonucleotide of claim 1, wherein the nucleobase is a pyrimidine base.
8. The oligonucleotide of claim 1, having from 5 to 9 2'-C-Bridged Bicyclic Nucleotides.
9. The oligonucleotide of claim 1, wherein at least 25% of nucleotides are 2'-C-Bridged Bicyclic Nucleotides.
10. The oligonucleotide of claim 1, wherein at least 50% of nucleotides are 2'-C-Bridged Bicyclic Nucleotides.
11. The oligonucleotide of claim 1, wherein at least 75% of nucleotides are 2'-C-Bridged Bicyclic Nucleotides.
12. The oligonucleotide of claim 1, wherein said oligonucleotide is from about 5 to 50 nucleotides in length.
13. The oligonucleotide of claim 1, wherein said oligonucleotide is from about 10 to 25 nucleotides in length.
14. The oligonucleotide of claim 1, wherein said oligonucleotide is less than 10 nucleotides or less than 8 nucleotides in length.
15. The oligonucleotide of claim 1, wherein said oligonucleotide comprises at least one nucleotide selected from 2' deoxy, 2' -O-methyl, 2'-fluoro, or a 2' to 4' methoxy bridge structure.
16. The oligonucleotide of claim 1 comprising one or more phosphorothioate linkages.
17. The oligonucleotide of claim 16, wherein said oligonucleotide is fully phosphorothioate-linked.
18. The oligonucleotide of claim 16, comprising one to three phosphate linkages.
19. The oligonucleotide of claim 1, wherein said 2'-C-Bridged Bicyclic Nucleotides are phosphorothioate linked.
20. The oligonucleotide of claim 1 comprising one or more phosphorodiamidate linkages.
21. The oligonucleotide of claim 1, wherein said oligonucleotide is fully linked by phosphorodiamidate linkages.
22. The oligonucleotide of claim 1, comprising one to three phosphorodiamidate linkages.
23. The oligonucleotide of claim 1, wherein said 2'-C-Bridged Bicyclic Nucleotides are phosphorodiamidate-linked.
24. The oligonucleotide of claim 20, wherein said phosphorodiamidate linkage is depicted as wherein
R$_1$, R$_2$, and R$_3$ are each independently selected from H, alkyl, alkenyl, oxo, aryl, benzyl, halogen, —OH, —NH2, alkoxy, an alcohol protecting group, or an amino protecting group;and
B is a nucleobase.
25. The oligonucleotide of claim 1 comprising at least one purine and/or pyrimidine base modification.
26. The oligonucleotide of claim 25, wherein said base modification is a carboxamido.
27. The oligonucleotide of claim 25, wherein said base modification is a carboxamido moiety at the C-8 position for the purine or the C-5 position for the pyrimidine.
28. The oligonucleotide of claim 1 comprising one or more morpholino nucleotides.
29. The oligonucleotide of claim 1 comprising a nucleotide sequence that is substantially complementary to a nucleotide sequence of a human microRNA.
30. The oligonucleotide of claim 29, wherein the nucleotide sequence is substantially complementary to a nucleotide sequence of a human microRNA selected from the group consisting of SEQ ID NOs:1-62 and SEQ ID NO:63.
31. The oligonucleotide of claim 29, wherein the nucleotide sequence is completely complementary to a nucleotide sequence of a human microRNA selected from the group consisting of SEQ ID NOs:1-62 and SEQ ID NO:63.
32. The oligonucleotide of claim 29, wherein the human microRNA is selected from the group consisting of miR-208a, miR-208b, miR-499, miR-15, miR-16, miR-195, miR- 29, miR-126, miR-206, miR-1, miR-143, miR-133, miR-451, miR-378, miR-92, miR-34a, miR-145, and miR-33.

33. The oligonucleotide of claim 29, wherein the nucleotide sequence is substantially complementary to a human miR-15a, miR-15b, miR-208a, miR-208b, miR-378, miR-451 and/or miR-499 sequence.

34. The oligonucleotide of claim 29, wherein the nucleotide sequence is completely complementary to a human miR-208a, miR-208b, miR-378, miR-451and/or miR-499 sequence.

35. A 2'-C-Bridged Bicyclic Nucleoside or Nucleotide having the structure of Formula I:

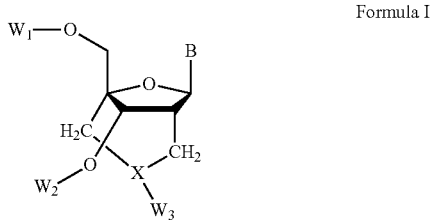

Formula I wherein
X is N;
$W_1$ and $W_2$ are each independently selected from H, an alcohol protecting group, phosphate ester, phosphorothioate ester, di- or tri-phosphate, or phosphoramidite;
$W_3$ is independently selected from H, an amine protecting group, phosphoramidite, phosphoramidate ester, phosphordiamidate ester, methyl, alkyl, cycloalkyl, carboxamide, a sugar, a fatty acid, other molecular conjugate, —$C_{1-4}$(O)R, or —COOR, wherein R is aryl, linear or cyclic alkyl or alkenyl, sugar, fatty acid, or other molecular conjugate such as a drug conjugate; and
B is a nucleobase.

36. A 2'-C-Bridged Bicyclic Nucleoside or Nucleotide having the structure of Formula I:

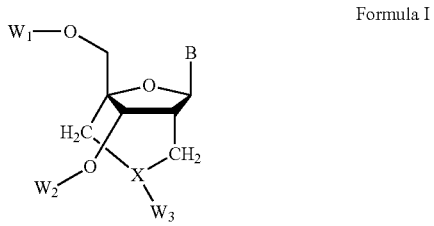

Formula I wherein
X is S;
$W_1$ and $W_2$ is each independently selected from H, an alcohol protecting group, phosphate ester, phosphorothioate ester, di- or tri-phosphate, or phosphoramidite;
$W_3$ is independently selected from null, O, a fatty acid, or other molecular conjugate; and
B is a nucleobase.

37. A pharmaceutical composition, comprising: an effective amount of the oligonucleotide of claim 1, or a pharmaceutically-acceptable salt thereof, and a pharmaceutically-acceptable carrier or diluent.

38. The pharmaceutical composition of claim 37, wherein the pharmaceutically-acceptable carrier comprises a colloidal dispersion system, macromolecular complex, nanocapsule, microsphere, bead, oil-in-water emulsion, micelle, mixed micelle, or liposome.

39. The pharmaceutical composition of claim 37, wherein said pharmaceutical composition is an aqueous formulation.

40. A method of reducing or inhibiting microRNA activity in a cell, comprising: contacting a cell with the oligonucleotide of claim 1.

41. The method of claim 40, wherein the microRNA selected from the group consisting of SEQ ID NOs:1-63, miR-15, miR-16, miR-195, miR-29, miR-126, miR-206, miR-1, miR-143, miR-133, miR-92, miR-34a, miR-145, and miR-33, miR-208a, miR-208b, miR-378, miR-451 and miR-499.

42. The method of claim 40, wherein the cell is a mammalian cell.

43. The method of claim 42, wherein the cell is a heart cell.

44. The method of claim 42, wherein the cell is in vivo or ex vivo.

45. A method of treating a heart condition in a subject comprising: administering to the subject the pharmaceutical composition of claim 37, wherein the heart condition is selected from the group consisting of cardiac hypertrophy, myocardial infarction, heart failure, vascular damage, and pathologic cardiac fibrosis.

46. The method of claim 45, wherein said pharmaceutical composition is administered by parenteral administration or by direct injection into heart tissue.

47. The method of claim 46, wherein said parenteral administration is intravenous, subcutaneous, intraperitoneal, or intramuscular.

48. The method of claim 45, wherein said pharmaceutical composition is administered by oral, transdermal, sustained release, controlled release, delayed release, suppository, catheter, or sublingual administration.

* * * * *